(12) United States Patent
Karanewsky et al.

(10) Patent No.: US 6,242,422 B1
(45) Date of Patent: Jun. 5, 2001

(54) (SUBSTITUTED)ACYL DIPEPTIDYL INHIBITORS OF THE ICE/CED-3 FAMILY OF CYSTEINE PROTEASES

(75) Inventors: Donald S. Karanewsky, Escondido, CA (US); Vincent J. Kalish, Annapolis, MD (US); Edward D. Robinson; Brett R. Ullman, both of San diego, CA (US)

(73) Assignee: Idun Pharmacueticals, Inc., San Diego, CA (US)

( * ) Notice: Subject to any disclaimer, the term of this patent is extended or adjusted under 35 U.S.C. 154(b) by 0 days.

(21) Appl. No.: 09/177,546

(22) Filed: Oct. 22, 1998

(51) Int. Cl.$^7$ .................... A61K 31/40; A61K 31/405; C07D 209/14; C07D 209/42
(52) U.S. Cl. ............. 514/19; 514/397; 514/414; 514/415; 514/419; 514/385; 548/492; 548/493; 548/312.1; 548/364.7
(58) Field of Search ............ 514/19, 397, 414, 514/415, 419, 383; 548/492, 493, 312.1, 364.7

(56) References Cited

U.S. PATENT DOCUMENTS

| 5,417,457 | 2/1998 | Zimmerman et al. | 514/231.5 |
|---|---|---|---|
| 5,656,627 | 8/1997 | Bemis et al. | 514/221 |
| 5,919,790 | 7/1999 | Allen et al. | 514/278 |

FOREIGN PATENT DOCUMENTS

| 0 623 592 A1 | 11/1994 | (EP). |
|---|---|---|
| 0 623 606 A2 | 11/1994 | (EP). |
| 0 644 197 A1 | 3/1995 | (EP). |
| 0 761 680 A2 | 3/1997 | (EP). |
| 2 292 149 | 2/1996 | (GB). |
| WO 93/09135 | 5/1993 | (WO). |
| WO 95/05192 | 2/1995 | (WO). |
| WO 96/30395 | 10/1996 | (WO). |
| WO 97/22618 | 6/1997 | (WO). |
| WO 99/47545 | 9/1999 | (WO). |
| WO 99/66945 | 12/1999 | (WO). |

OTHER PUBLICATIONS

Dolle et al., "Pyridazinodiazepines as a High–Affinity, $P_2$–$P_3$ Peptidomimetic Class of Interleukin–1β–Converting Enzyme Inhibitor," *J. Med. Chem.* 40(13):1941–1945, 1997.

Semple et al., "Peptidomimetic Aminomethylene Ketone Inhibitors of Interleukin–1β–Converting Enzyme (ICE)," *Bioorganic & Medicinal Chemistry Letters* 8:959–964, 1998.

*Primary Examiner*—Christopher S. F. Low
*Assistant Examiner*—Stephen Tu
(74) *Attorney, Agent, or Firm*—Seed Intellectual Property Law Group PLLC

(57) ABSTRACT

This invention is directed to novel (substituted)acyl dipeptidyl ICE/ced-3 family inhibitor compounds. The invention is also directed to pharmaceutical compositions containing these compounds, as well as the use of such compositions in the treatment of patients suffering inflammatory, autoimmune and neurodegenerative diseases, for the prevention of ischemic injury, and for the preservation of organs that are to undergo a transplantation procedure.

36 Claims, No Drawings

(SUBSTITUTED)ACYL DIPEPTIDYL INHIBITORS OF THE ICE/CED-3 FAMILY OF CYSTEINE PROTEASES

TECHNICAL FIELD

The present invention relates to novel classes of compounds which are inhibitors of interleukin-1β converting enzyme and related proteases ("ICE/ced-3 family of cysteine proteases"), as well as to pharmaceutical compositions comprising these compounds and to methods of using such pharmaceutical compositions.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al., *Immunology Today,* 7:45–56 (1986). As such, it is involved in the pathogenesis of chronic and acute inflammatory and autoimmune diseases. IL-1 is predominantly produced by peripheral blood monocytes as part of the inflammatory response. Mosely, B. S. et al., *Proc. Nat. Acad. Sci.,* 84:4572–4576 (1987); Lonnemann, G. et al., *Eur. J. Immunol.,* 19:1531–1536 (1989).

IL-1β is synthesized as a biologically inactive precursor, proIL-1β. ProIL-1β is cleaved by a cysteine protease called interleukin-1β converting enzyme ("ICE") between Asp-116 and Ala-117 to produce the biologically active C-terminal fragment found in human serum and synovial fluid. Sleath, P. R. et al., *J. Biol. Chem.,* 265:14526–14528 (1992); A. D. Howard et al., *J. Immunol.,* 147:2964–2969 (1991).

ICE is a cysteine protease localized primarily in monocytes. In addition to promoting the pro-inflammatory and immunoregulatory properties of IL-1β, ICE, and particularly its homologues, also appear to be involved in the regulation of cell death or apoptosis. Yuan, J. et al., *Cell,* 75:641–652 (1993); Miura, M. et al., *Cell,* 75:653–660 (1993); Nett-Giordalisi, M. A. et al., *J. Cell Biochem.,* 17B:117 (1993). In particular, ICE or ICE/ced-3 homologues are thought to be associated with the regulation of apoptosis in neurogenerative diseases, such as Alzheimer's and Parkinson's disease. Marx, J. and M. Baringa, *Science,* 259:760–762 (1993); Gagliardini, V. et al., *Science,* 263:826–828 (1994).

Thus, disease states in which inhibitors of the ICE/ced-3 family of cysteine proteases may be useful as therapeutic agents include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, ischemic diseases such as the myocardial infarction, stroke and ischemic kidney disease; immune-based diseases, such as hypersensitivity; auto-immune diseases, such as multiple sclerosis; bone diseases; and certain neurodegenerative diseases, such as Alzheimer's and Parkinson's disease. Such inhibitors are also useful for the repopulation of hematopoietic cells following chemo- and radiation therapy and for prolonging organ viability for use in transplantation.

ICE/ced-3 inhibitors represent a class of compounds useful for the control of the above-listed disease states. Peptide and peptidyl inhibitors of ICE have been described. However, such inhibitors have been typically characterized by undesirable pharmacologic properties, such as poor oral absorption, poor stability and rapid metabolism. Plattner, J. J. and D. W. Norbeck, in *Drug Discovery Technologies,* C. R. Clark and W. H. Moos, Eds. (Ellis Horwood, Chichester, England, 1990), pp. 92–126. These undesirable properties have hampered their development into effective drugs.

Accordingly, the need exists for compounds that can effectively inhibit the action of the ICE/ced-3 family of proteases, for use as agents for preventing unwanted apoptosis and for treating chronic and acute forms of IL-1 mediated diseases, such as inflammatory, autoimmune or neurodegenerative diseases. The present invention satisfies this need and provides further related advantages.

SUMMARY OF THE INVENTION

In general, the compounds of this invention incorporate an aryl or heteroaryl substituted acyl group as a dipeptide mimetic. The resulting compounds exhibit improved properties relative to their peptidic counterparts, for example, such as improved cell penetration or improved absorption and metabolic stability resulting in enhanced bioavailability.

One aspect of the instant invention is the compounds of the Formula I:

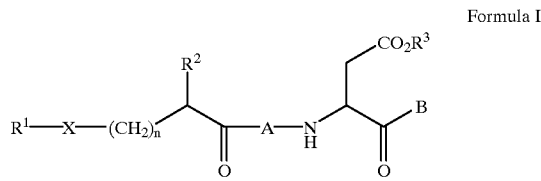

Formula I wherein A, B, X, n, $R^1$, $R^2$ and $R^3$ are as defined below, as well as pharmacuetically acceptable salts thereof.

A further aspect of the instant invention is a pharmaceutical composition comprising a compound of the above Formula I and a pharmaceutically-acceptable carrier therefor.

Another aspect of this invention involves a method for treating an autoimmune disease comprising administering an effective amount of a pharmaceutical composition discussed above to a patient in need of such treatment.

Yet another aspect of the instant invention is a method for treating an inflammatory disease comprising administering an effective amount of a pharmaceutical composition discussed above to a patient in need of such treatment.

A further aspect of the instant invention is a method for treating a neurodegenerative disease comprising administering an effective amount of a pharmaceutical composition discussed above to a patient in need of such treatment.

Another aspect of the instant invention is a method of preventing ischemic injury to a patient suffering from a disease associated with ischemic injury comprising administering an effective amount of the pharmaceutical composition discussed above to a patient in need of such treatment.

A further aspect of the instant invention is a method for expanding of hematopoietic cell populations and/or enhancing their survival by contacting the cells with an effective amount of the pharmaceutical composition discussed above. Cell populations included in the method of the invention include (but are not limited to) granulocytes, monocytes, erthrocytes, lymphocytes and platelets for use in cell transfusions.

An alternate aspect of the instant invention is a method of prolonging the viability of an organ that has been removed from the donor for the purpose of a future transplantation procedure, which comprises applying an effective amount of the pharmaceutical composition discussed above to the organ, thereby prolonging the viability of the organ as compared to an untreated organ. The organ may be an intact organ, or isolated cells derived from an organ (e.g., isolated pancreatic islet cells, isolated dopaminergic neurons, blood or hematopoietic cells).

These and other aspects of this invention will be evident upon reference to the following detailed description.

DETAILED DESCRIPTION OF THE INVENTION

As mentioned above, one aspect of the instant invention is the compounds of the Formula I:

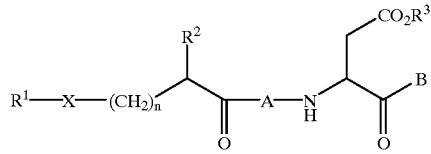

Formula I wherein:

n is 0, 1 or 2;

X is $CH_2$, C=O, O, S or NH;

A is a natural or unnatural amino acid of Formula IIa–i:

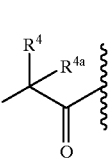

IIa

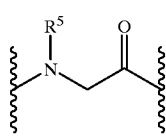

IIb

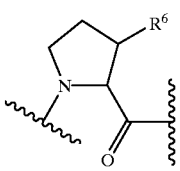

IIc

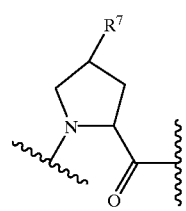

IId

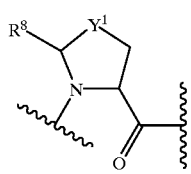

IIe

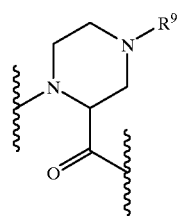

IIf

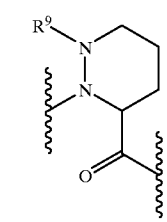

IIg

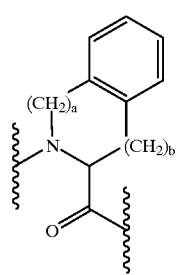

IIh

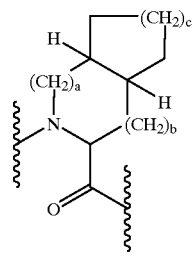

IIi

B is a hydrogen atom, a deuterium atom, $C_{1-10}$ straight chain or branched alkyl, cycloalkyl, phenyl, substituted phenyl, naphthyl, substituted naphthyl, 2-benzoxazolyl, substituted 2-oxazolyl, $(CH_2)_m$ycloalkyl, $(CH_2)_m$phenyl, $(CH_2)_m$(substituted phenyl), $(CH_2)_m$(1 or 2-naphthyl), $(CH_2)_m$heteroaryl, halomethyl, $CO_2R^{13}$, $CONR^{14}R^{15}$, $CH_2ZR^{16}$, $CH_2OCO$(aryl), $CH_2OCO$(heteroaryl), or $CH_2OPO(R^{17})R^{18}$, where Z is an oxygen or a sulfur atom, or B is a group of the Formula IIIa–c:

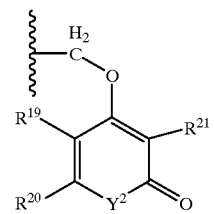

IIIa

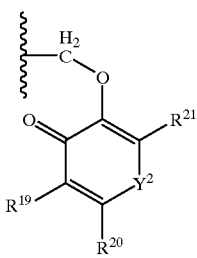

IIIb

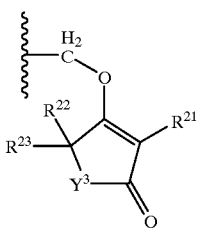

IIIc $R^1$ is phenyl, substituted phenyl, naphthyl, substituted naphthyl, heteroaryl, or substituted heteroaryl;

$R^2$ is hydrogen, alkyl, cycloalkyl, phenyl, substituted phenyl, $(CH_2)_mNH_2$, $(CH_2)_mNHCOR^{10}$, $(CH_2)_mN(C=NH)NH_2$, $(CH_2)_pCO_2R^3$, $(CH_2)_pOR^{11}$, $(CH_2)_pSR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

$R^3$ is hydrogen, alkyl, cycloalkyl, (cycloalkyl)alkyl, phenylalkyl, or substituted phenylalkyl; and wherein $R^4$ is alkyl, cycloalkyl, phenyl, substituted phenyl, $(CH_2)_mNH_2$, $(CH_2)_mNHCOR^{10}$, $(CH_2)_mN(C=NH)NH_2$, $(CH_2)_pCO_2R^3$, $(CH_2)_pOR^{11}$, $(CH_2)_pSR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

$R^{4a}$ is hydrogen or methyl, or $R^4$ and $R^{4a}$ taken together are —$(CH_2)_d$— where d is an interger from 2 to 6;

$R^5$ is phenyl, substituted phenyl, $(CH_2)_p$phenyl, $(CH_2)_p$(substituted phenyl), cycloalkyl, or benzofused cycloalkyl;

$R^6$ is hydrogen, alkyl, cycloalkyl, phenyl, substituted phenyl, $(CH_2)_m$cycloalkyl, $(CH_2)_m$phenyl, $(CH_2)_m$(substituted phenyl), or $(CH_2)_m$(1 or 2-naphthyl);

$R^7$ is hydrogen, fluorine, oxo (i.e., =O), alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{11}$, $SR^{12}$, or $NHCOR^{10}$;

$R^8$ is hydrogen, oxo, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^9$ is alkyl, cycloalkyl, $(CH_2)_m$cycloalkyl, $(CH_2)_m$phenyl, $(CH_2)_m$(substituted phenyl), $(CH_2)_m$(1 or 2-naphthyl), or $COR^{10}$;

$R^{10}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{13}$, or $NR^{14}R^{15}$;

$R^{11}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^{12}$ is alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^{13}$ is alkyl, cycloalkyl, $(CH_2)_m$cycloalkyl, $(CH_2)_m$phenyl, $(CH_2)_m$(substituted phenyl), or $(CH_2)_m$(1 or 2-naphthyl);

$R^{14}$ is hydrogen, alkyl, cycloalkyl, phenyl, substituted phenyl, naphthyl, substituted naphthyl, $(CH_2)_m$cycloalkyl, $(CH_2)_m$phenyl, $(CH_2)_m$(substituted phenyl), or $(CH_2)_m$(1 or 2-naphthyl);

$R^{15}$ is hydrogen or alkyl; or $R^{14}$ and $R^{15}$ taken together form a five, six or seven membered carbocyclic or heterocyclic ring, such as morpholine or N-substituted piperazine;

$R^{16}$ is phenyl, substituted phenyl, naphthyl, substituted naphthyl, heteroaryl, $(CH_2)_m$phenyl, $(CH_2)_m$(substituted phenyl), $(CH_2)_m$(1 or 2-naphthyl), or $(CH_2)_m$heteroaryl;

$R^{17}$ and $R^{18}$ are independently alkyl, cycloalkyl, phenyl, substituted phenyl, naphthyl, or phenylalkyl, substituted phenylalkyl, or (cycloalkyl)alkyl;

$R^{19}$ and $R^{20}$ are independently hydrogen, alkyl, phenyl, substituted phenyl, $(CH_2)_m$phenyl, or $(CH_2)_m$(substituted phenyl), or $R^{19}$ and $R^{20}$ taken together are —$(CH=CH)_2$—;

$R^{21}$ is hydrogen, alkyl, phenyl, substituted phenyl, $(CH_2)_m$phenyl, $(CH_2)_m$(substituted phenyl);

$R^{22}$, $R^{23}$ and $R^{24}$ are independently hydrogen or alkyl;

$Y^1$ is $CH_2$, $(CH_2)_2$, $(CH_2)_3$, or S;

$Y^2$ is O or $NR^{24}$;

$Y^3$ is $CH_2$, O, or $NR^{24}$;

a is 0 or 1 and b is 1 or 2, provided that when a is 1 then b is 1;

c is 1 or 2, provided that when c is 1 then a is 0 and b is 1;

m is 1, 2,3or 4; and p is 1 or 2;

or a pharmaceutically acceptable salt thereof.

As used herein, the term "alkyl" means a straight or branched $C_1$ to $C_8$ carbon chain such as methyl, ethyl, tert-butyl, iso-propyl, n-octyl, and the like. The term "lower alkyl" means a straight or branched $C_1$ to $C_6$ carbon chain, such as methyl, ethyl, iso-propyl, and the like.

The term "cycloalkyl" means a mono-, bi-, or tricyclic ring that is either fully saturated or partially unsaturated. Examples of such a ring include cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted with one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more, and preferably one or two, substituents chosen from halogen, hydroxy, protected hydroxy, cyano, nitro, trifluoromethyl, alkyl, alkoxy, acyl, acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N-(lower alkyl)carboxamide, protected N-(lower alkyl)carboxamide, N,N-di(lower alkyl)carboxamide, N-((lower alkyl)sulfonyl) amino, N-(phenylsulfonyl)amino or by a substituted or unsubstituted phenyl group, such that in the latter case a biphenyl or naphthyl group results.

Examples of the term "substituted phenyl" includes a mono- or di(halo)phenyl group such as 2-, 3- or 4-chlorophenyl, 2,6-dichlorophenyl, 2,5-dichlorophenyl, 3,4-dichlorophenyl, 2-,3- or 4-bromophenyl, 3,4-dibromophenyl, 3-chloro-4-fluorophenyl, 2-, 3- or 4-fluorophenyl and the like; a mono or di(hydroxy)phenyl group such as 2-, 3-, or 4-hydroxyphenyl, 2,4-dihydroxyphenyl, the protected-hydroxy derivatives thereof and the like; a nitrophenyl group such as 2-, 3-, or 4-nitrophenyl; a cyanophenyl group, for example, 2-,3- or 4-cyanophenyl; a mono- or di(alkyl)phenyl group such as 2-, 3-, or 4-methylphenyl, 2,4-dimethylphenyl, 2-, 3- or 4-(isopropyl)phenyl, 2-, 3-, or 4-ethylphenyl, 2-, 3- or 4-(n-propyl)phenyl and the like; a mono or di(alkoxy)phenyl group, for example, 2,6-dimethoxyphenyl, 2-, 3- or 4-(isopropoxy)phenyl, 2-, 3- or 4-(t-butoxy)phenyl, 3-ethoxy-4-methoxyphenyl and the like; 2-, 3- or 4-trifluoromethylphenyl; a mono- or dicarboxyphenyl or (protected carboxy)phenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl)phenyl or (protected aminomethyl)phenyl such as 2-, 3- or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "phenylalkyl" means one of the above phenyl groups attached to one of the above-described alkyl groups, and the term "substituted phenylalkyl means that either the phenyl or the alkyl, or both, are substituted with one or more of the above-identified substituents. Examples of such groups include 2-phenyl-1-chloroethyl, 2-(4'-methoxyphenyl)ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl, and the like.

The term "substituted naphthyl" means a naphthyl group substituted with one or more of the above-identified substituents, and the term "(1 or 2 naphyl)alkyl" means a naphthyl attached to one of the above-described alkyl groups at the 1 or 2 position.

The terms "halo" and "halogen" refer to the fluoro, chloro, bromo or iodo groups. These terms may also be used to describe one or more halogens, which are the same or different. Preferred halogens in the context of this invention are chloro and fluoro.

The term "aryl" refers to aromatic five and six membered carbocyclic rings. Six membered rings are preferred.

The term "heteroaryl" denotes optionally substituted aromatic five-membered or six-membered heterocyclic rings that have 1 to 4 heteroatoms, such as oxygen, sulfur and/or nitrogen atoms, in particular nitrogen, either alone or in conjunction with sulfur or oxygen ring atoms.

The following ring systems are representative examples of the heterocyclic radicals denoted by the term "heteroaryl" (whether substitued or unsubstituted): thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzothiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, lower alkyl, substituted alkyl, cycloalkyl, substituted cycloalkyl, (cycloalkyl)alkyl, substituted (cycloalkyl)alkyl, phenyl, substituted phenyl, phenylalkyl, and substituted phenylalkyl groups.

Substituents for the heteroaryl group are as defined above, or as set forth below. As used in conjunction with the above substituents for heteroaryl rings, "trihalomethyl" can be trifluoromethyl, trichloromethyl, tribromomethyl or triiodomethyl, "lower alkoxy" means a $C_1$ to $C_4$ alkoxy group, similarly, "lower alkylthio" means a $C_1$ to $C_4$ alkylthio group. The term "substituted lower alkyl" means the above-defined lower alkyl group substituted from one to three times by a hydroxy, protected hydroxy, amino, protected amino, cyano, halo, trifluoromethyl, mono-substituted amino, di-substituted amino, lower alkoxy, lower alkylthio, carboxy, protected carboxy, or a carboxy, amino, and/or hydroxy salt.

As used in conjunction with the substituents for the heteroaryl rings, the terms "substituted (cycloalkyl)alkyl" and "substituted cycloalkyl" are as defined above substituted with the same groups as listed for a "substituted alkyl" group. The term "(monosubstituted)amino" refers to an amino group with one substituent chosen from the group consisting of phenyl, substituted phenyl, alkyl, substituted alkyl, $C_1$ to $C_7$ acyl, $C_2$ to $C_7$ alkenyl, $C_2$ to $C_7$ substituted alkenyl, $C_2$ to $C_7$ alkynyl, $C_7$ to $C_{16}$ alkyl $C_7$ to $C_{16}$ substituted alkylaryl and heteroaryl group. The (monosubstituted)amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_6$ substituted alkylaryl and heteroaryl. The two substituents can be the same or different. The term "heteroaryl(alkyl)" denotes an alkyl group as defined above, substituted at any position by a heteroaryl group, as above defined.

Furthermore, the above optionally substituted five-membered or six-membered heterocyclic rings can optionally be fused to a aromatic 5-membered or 6-membered aryl or heteroaryl ring system. For example, the rings can be optionally fused to an aromatic 5-membered or 6-membered ring system such as a pyridine or a triazole system, and preferably to a benzene ring.

The term "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); and ammonium ion; and the organic cations (for example, dibenzylammonium, benzylammonium, 2-hydroxyethylammonium, bis(2-hydroxyethyl)ammonium, phenylethylbenzylammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and includes organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in C. B. Reese and E. Haslam, "Protective Groups in Organic Chemistry," J. G. W. McOmie, Ed., Plenum Press, New York, N.Y., 1973, Chapter 5, respectively, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl, and the like.

Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tert-butyl group. The related term "protected hydroxy" denotes a hydroxy group bonded to one of the above hydroxy-protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom.

Examples of such amino-protecting groups include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl) isopropoxycarbonyl, 1,1-diphenylethyl-1-oxycarbonyl, 1,1-diphenylpropyl-1-oxycarbonyl, 2-(3,5-dimethoxyphenyl) propyl-2-oxycarbonyl ("Ddz"), 2-(p-toluyl)propyl-2-oxycarbonyl, cyclopentanyloxycarbonyl, 1-methylcyclopentanyl-oxycarbonyl, cyclohexanyloxycarbonyl, 1-methyl-cyclohexanyloxycarbonyl, 2-methylcyclohexanyl-oxycarbonyl, 2-(4-toluylsulfonyl)ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, α-2,4,5,-tetramethylbenzyl-oxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl and the like; the benzoylmethylsulfonyl group, the 2,2,5,7,8-pentamethylchroman-6-sulfonyl group ("PMC"), the dithiasuccinoyl ("Dts") group, the 2-(nitro) phenyl-sulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised Ed., Springer-Verlag, New York, N.Y., 1984 and 1993, and J. M. Stewart and J. D. Young, "Solid Phase Peptide Synthesis,"

2nd Ed., Pierce Chemical Co., Rockford, Ill., 1984, E. Atherton and R. C. Shephard, "Solid Phase Peptide Synthesis—A Practical Approach" IRL Press, Oxford, England (1989), each of which is incorporated herein by reference. The related term "protected amino" defines an amino group substituted with an amino-protecting group discussed above.

The terms "natural and unnatural amino acid" refers to both the naturally occurring amino acids and other non-proteinogenic α-amino acids commonly utilized by those in the peptide chemistry arts when preparing synthetic analogues of naturally occurring peptides, including D and L forms. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of unnatural alpha-amino acids include hydroxylysine, citrulline, kynurenine, (4-aminophenyl) alanine, 3-(2'-naphthyl)alanine, 3-(1'-naphthyl)alanine, methionine sulfone, (t-butyl)alanine, (t-butyl)glycine, 4-hydroxyphenyl-glycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxy-kynurenine, 3-aminotyrosine, trifluoromethylalanine, 2-thienylalanine, (2-(4-pyridyl) ethyl)cysteine, 3,4-dimethoxy-phenylalanine, 3-(2'-thiazolyl)alanine, ibotenic acid, 1-amino-1-cyclopentane-carboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, norleucine, norvaline, alloisoleucine, homoarginine, thioproline, dehydro-proline, hydroxyproline, homoproline, indoline-2-carboxylic acid, 1,2,3,4-tetrahydroisoquinoline-3-carboxylic acid, 1,2,3,4-tetrahydroquinoline-2-carboxylic acid, α-amino-n-butyric acid, cyclohexylalanine, 2-amino-3-phenylbutyric acid, phenylalanine substituted at the ortho, meta, or para position of the phenyl moiety with one or two of the following groups: a ($C_1$ to $C_4$)alkyl, a ($C_1$ to $C_4$)alkoxy, a halogen or a nitro group, or substituted once with a methylenedioxy group; β-2- and 3-thienylalanine; β-2- and 3-flranylalanine; β-2-, 3- and 4-pyridylalanine; β-(benzothienyl-2- and 3-yl)alanine; β-(1- and 2-naphthyl) alanine; O-alkylated derivatives of serine, threonine or tyrosine; S-alkylated cysteine, S-alkylated homocysteine, the O-sulfate, O-phosphate and O-carboxylate esters of tyrosine; 3-(sulfo)tyrosine, 3-(carboxy)tyrosine, 3-(phospho)tyrosine, the 4-methane-sulfonic acid ester of tyrosine, 4-methanephosphonic acid ester of tyrosine, 3,5-diiodotyrosine, 3-nitrotyrosine, ε-alkyllysine, and delta-alkyl ornithine. Any of these α-amino acids may be substituted with a methyl group at the alpha position, a halogen at any position of the aromatic residue on the α-amino side chain, or an appropriate protective group at the O, N, or S atoms of the side chain residues. Appropriate protective groups are discussed above.

Depending on the choice of solvent and other conditions known to the practitioner skilled in the art, compounds of this invention may also take the ketal or acetal form, which forms are included in the instant invention. In particular, compounds of Formula I in which $R^3$ is a hydrogen atom (i.e., Formula Ia) may exist in the cyclic ketal or acetal form Formula Ia' shown below:

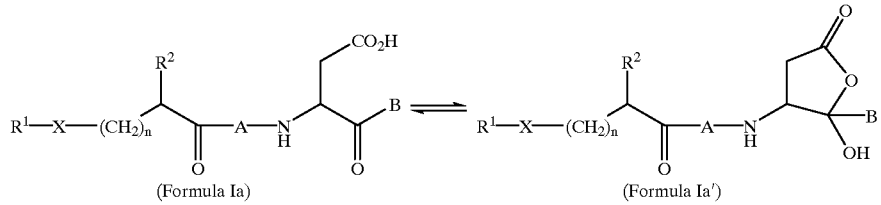

(Formula Ia)  (Formula Ia')

In addition, it should be understood that the equilibrium forms of the compounds of this invention may include tautomeric forms. All such forms of these compounds are expressly included in the present invention.

The compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of exertion. In addition, the compounds may be altered to pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups, especially where they occur in the group donated as "A" in Formula I or the modified aspartic acid residue attached to the group denoted as "A".

Compounds of this invention with respect to the groups $R^1$, $R^2$, and X in Formula I, include those wherein:

$R^1$ is substituted phenyl (such as 2-substituted phenyl), naphthyl, or substituted naphthyl;

$R^2$ is hydrogen, lower alkyl, $(CH_2)_pCO_2R^3$, $(CH_2)_m$ phenyl, $(CH_2)_m$(substituted phenyl), $(CH_2)_m$(1 or 2-naphthyl), or $(CH_2)_m$tetrazolyl, where p is 1 or 2, m is 1 or 2;

$R^3$ is hydrogen or alkyl;

X is O or NH; and n is 0 or 1.

Compounds of this invention with respect to the group "A" in Formula I, include those of Formula IIa wherein:

$R^4$ is lower alkyl, cycloalkyl, phenyl, substituted phenyl, $(CH_2)_mNH_2$, $(CH_2)_pOR^{11}$, $(CH_2)_pSR^{12}$, $(CH_2)_m$ cycloalkyl, $(CH_2)_m$phenyl, $(CH_2)_m$(substituted phenyl), or $(CH_2)_m$(1 or 2-naphthyl);

$R^{11}$ is hydrogen, lower alkyl, cycloalkyl, phenyl, substituted phenyl, naphthyl, $(CH_2)_m$cycloalkyl, $(CH_2)_m$ phenyl, $(CH_2)_m$(substituted phenyl), or $(CH_2)_m$(1 or 2-naphthyl);

$R^1$ is lower alkyl, cycloalkyl, phenyl, substituted phenyl, naphthyl, $(CH_2)_m$cycloalkyl, $(CH_2)_m$phenyl, $(CH_2)_m$ (substituted phenyl), or $(CH_2)_m$(1 or 2-naphthyl); and m is 1,2,3,4 and p is 1 or 2.

Compounds of this invention with respect to the group "A" in Formula I, also include those of Formula IIb wherein:

$R^5$ is phenyl, substituted phenyl, $(CH_2)_p$phenyl, $(CH_2)_p$ (substituted phenyl), cycloalkyl, or 2-indanyl; and p is 1 or 2.

Another group of compounds with respect to the group "A" in Formula I, include those of Formula IId wherein:

$R^7$ is hydrogen, fluorine, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{11}$, or $SR^{12}$;

$R^{11}$ and $R^{12}$ are independently cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl); and m is 1,2,3 or 4.

A forth group of compounds with respect to the group "A" in Formula I, include those of Formula IIe wherein:

$R^8$ is hydrogen, oxo, cycloalkyl, phenyl, substituted phenyl, or naphthyl; and $Y^1$ is $CH_2$, $(CH_2)_2$, $(CH_2)_3$, or S.

Another group of compounds with respect to the group "A" in Formula I, include those of Formula IIh wherein:

a is 0 and b is 1 or 2.

Compounds of this invention with respect to the group "B" in Formula I, include those wherein:

B is hydrogen, 2-benzoxazolyl, substituted 2-oxazolyl, $CH_2ZR^{16}$, $CH_2OCO(aryl)$, or $CH_2OPO(R^{17})R^{18}$, where Z is O or S;

$R^{16}$ is phenyl, substituted phenyl, naphthyl, substituted naphthyl, heteroaryl, $(CH_2)_m$phenyl, $(CH_2)_m$ (substituted phenyl), $(CH_2)_m$(1 or 2-naphthyl), or $(CH_2)_m$heteroaryl;

$R^{17}$ and $R^{18}$ are independently alkyl, cycloalkyl, phenyl, substituted phenyl, naphthyl, phenylalkyl, substituted phenylalkyl and (cycloalkyl)alkyl.

Another group of compounds with respect to the group "B" in Formula I, include those of Formula IIIa–c wherein:

$Y^2$ is O or $NR^{24}$;

$Y^3$ is $CH_2$, O, or $NR^{24}$;

$R^{19}$ and $R^{20}$ are independently hydrogen, alkyl, phenyl, or $R^{19}$ and $R^{20}$ taken together are $—(CH=CH)_2—$;

$R^{21}$ is hydrogen, alkyl, phenyl, substituted phenyl, $(CH_2)_m$ phenyl, or $(CH_2)_m$(substituted phenyl);

$R^{22}$, $R^{23}$ and $R^{24}$ are independently hydrogen or alkyl.

The compounds of Formula I may be synthesized using conventional techniques as discussed below. Advantageously, these compounds are conveniently synthesized from readily available starting materials.

One synthetic route for synthesizing the instant compounds is set forth in the following Scheme 1:

SCHEME 1

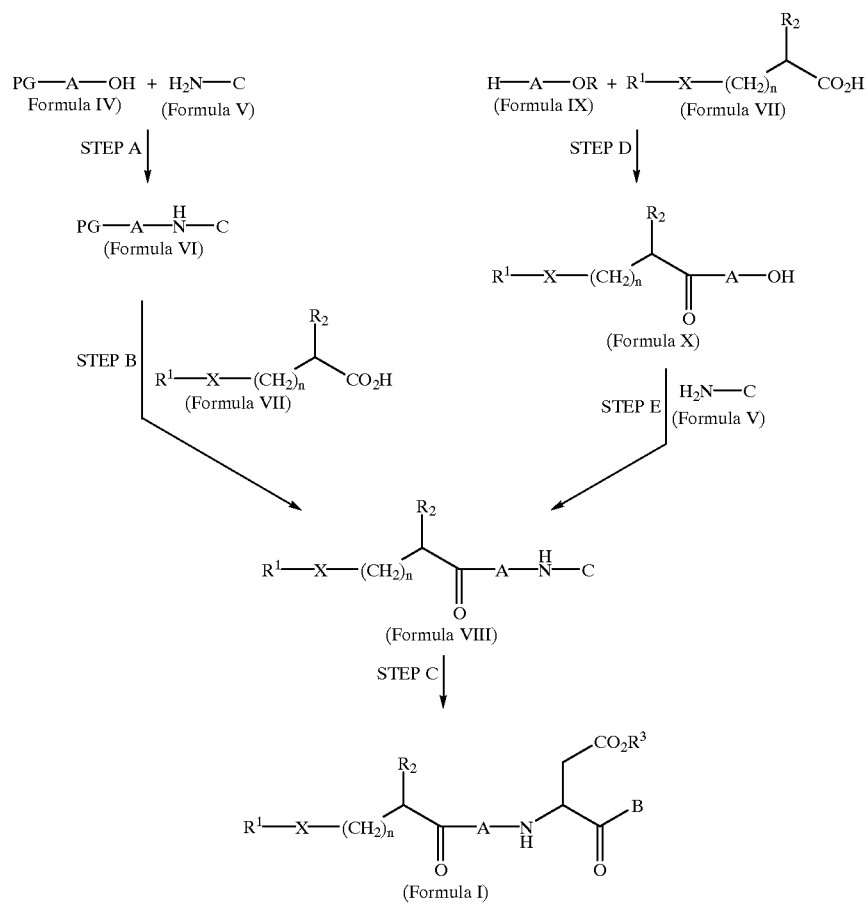

In the above Scheme 1, Formula (V), that is H$_2$N—C, is a modified aspartic acid residue of Formulas Va through Vd:

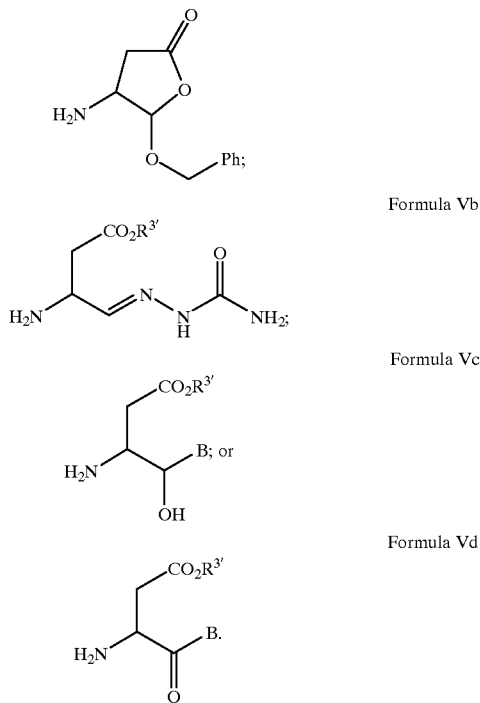

In the above Scheme 1, "PG" stands for an amino protecting group and "A" stands for a natural or unnatural amino acid of formula IIa through IIi, as discussed above. In Formula Vb through Vd, R$^{3'}$ is a carboxyl protecting group as described in the definition of R$^3$ in Formula I with the exception that R$^{3'}$ cannot be a hydrogen atom.

The modified aspartic acids of Formula Va–d can be prepared by methods well known in the art. See, for example, European Patent Application 519,748; PCT Patent Application No. PCT/EP92/02472; PCT Patent Application No. PCT/US91/06595; PCT Patent Application No. PCT/US91/02339; European Patent Application No. 623,592; World Patent Application No. WO 93/09135; PCT Patent Application No. PCT/US94/08868; European Patent Application No. 623,606; European Patent Application No. 618,223; European Patent Application No. 533,226; European Patent Application No. 528,487; European Patent Application No. 618,233; PCT Patent Application No. PCT/EP92/02472; World Patent Application No. WO 93/09135; PCT Patent Application No. PCT/US93/03589; and PCT Patent Application No. PCT/US93/00481, all of which are herein incorporated by reference.

The coupling reactions carried out under Step A are performed in the presence of a standard peptide coupling agent such as the combination of the combination of dicyclohexylcarbodiimide(DCC) and 1-hydroxybenzotriazole(HOBt), as well as the BOP (benzotriazolyloxy-tris-(dimethylamino)phosphonium hexafluorophosphate) reagent, pyBOP (benzotriazolyloxy-tris(N-pyrolidinyl)phosphoniumhexafluorophosphate), HBTU (O-benzotriazolyly-tetramethylisouronium-hexafluorophosphate), and EEDQ (1-ethyloxycarbonyl-2-ethyloxy-1,2-dihydroquinoline) reagents, the combination of 1-ethyl(3,3'-dimethyl-1'-aminopropyl)carbodiimide (EDAC) and HOBt, and the like, as discussed in J. Jones, "Amino Acid and Peptide Synthesis," Steven G. Davis ed., Oxford University Press, Oxford, pp. 25–41 (1992); M. Bodanzky, "Principles of Peptide Synthesis," Hafner et al. ed., Springer-Verlag, Berlin Heidelberg, pp. 9–52 and pp. 202–251 (1984); M. Bodanzky, "Peptide Chemistry, A Practical Textbook," Springer-Verlag, Berlin Heidelberg, pp. 55–73 and pp. 129–180; and Stewart and Young, "Solid Phase Peptide Synthesis," Pierce Chemical Company, (1984), all of which are herein incorporated by reference. The amino protecting group is then removed and the resulting amine is coupled to the (substituted) carboxylic acid of Formula VII (Step B). Again, this coupling reaction uses the standard peptide coupling reactions mentioned above.

Alternatively, the (substituted)carboxylic acid of Formula VII can be coupled to an amino ester of Formula IX (Step D). Again, this coupling reaction uses the standard peptide coupling reactions mentioned above. In Formula IX, the group R is a carboxyl protecting group such as methyl, allyl, benzyl or tert-butyl. After removal of the carboxyl protecting group under standard conditions well known in the art, the resulting carboxylic acid is coupled to amine V using the standard peptide coupling methods described above (Step E).

In the case where the coupling reaction depicted by either Step A or Step E was carried out with the amino alcohol of Formula Vc, the alcohol moiety must be oxidized to the corresponding carbonyl compound prior to removal of the protecting groups. Preferred methods for the oxidation reaction include Swern oxidation (oxalyl chloride-dimethyl sulfoxide, methylene chloride at −78° C. followed by triethylamine); and Dess-Martin oxidation (Dess-Martin periodinane, t-butanol, and methylene chloride.) The protecting groups contained in substructures of the Formula Va–d, VII and A are removed by methods well known in the art. These reactions and removal of some or all of the protecting groups are involved in Step C in the above Scheme 1.

An alternative synthetic route for synthesizing the instant compounds is set forth in the following Scheme 2:

SCHEME 2

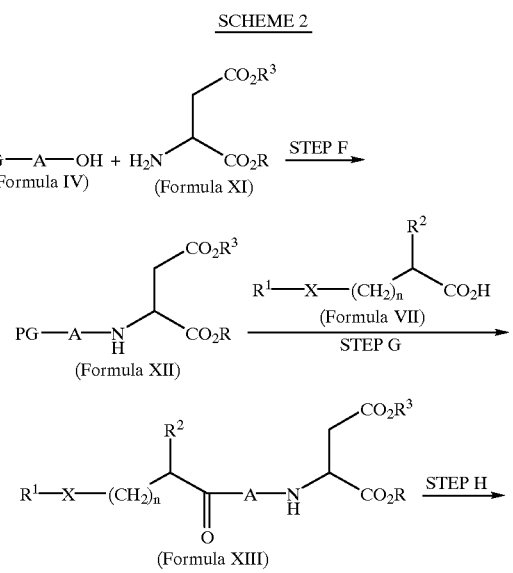

-continued

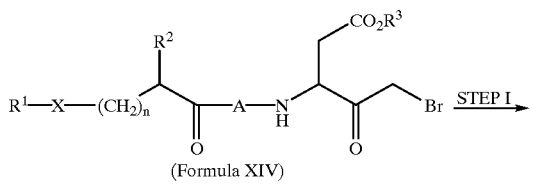

(Formula XIV)

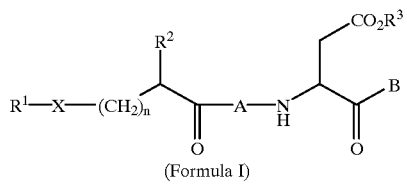

(Formula I)

In the above Scheme 2, "PG" stands for an amino protecting group and "A" stands for a natural or unnatural amino acid of formula IIa through IIi, as discussed above. The group R is a carboxyl protecting group such as trimethylsilyl, methyl, allyl, benzyl or tert-butyl.

The coupling reactions carried out under Step F and Step G are performed in the presence of a standard peptide coupling agent as discussed above. In Step G, the amino protecting group must be removed prior to the coupling step. In Step H the alpha-carboxy protecting group R of the compound of Formula XIII is selectively removed and the resulting mono-carboxylic acid treated sequentially with diazomethane and hydrobromic acid to give the alpha-bromoketone of Formula XIV.

In Step I, the bromoketone of Formula XIV is treated with either $R^{16}Z$—H, (aryl)—$CO_2H$, (heteroaryl)—$CO_2H$, or $R^{17}(R^{18})PO_2H$ in the presence of an inorganic base such as potassium carbonate or potassium fluoride in an inert solvent such as dimethyl formamide to give the corresponding compound of Formula I in which B is $CH_2ZR^{16}$, $CH_2OCO$(aryl), $CH_2OCO$(heteroaryl), or $CH_2OPO(R^{17})R^{18}$, respectively. Compounds of Formula I in which B is a fragment of Formula III may also be prepared in a similar fashion. The protecting groups contained in substructures of the Formula VII, XI and A are removed by methods well known in the art. These reactions and removal of some or all of the protecting groups are involved in Step I in the above Scheme 2.

An alternative method for the prepartion of compounds of the instant invention of Formula I in which $R^3$ and B are both hydrogen (i.e., Formula Ib) is set forth below in Scheme 3:

SCHEME 3

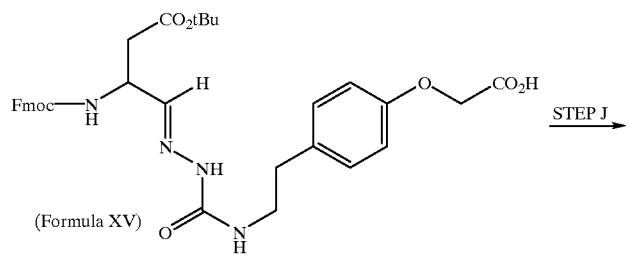

(Formula XV)

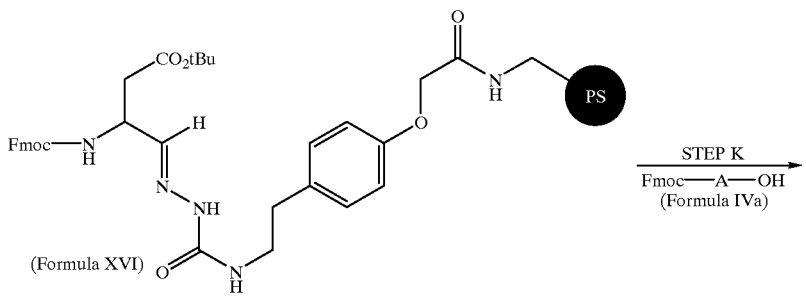

(Formula XVI)

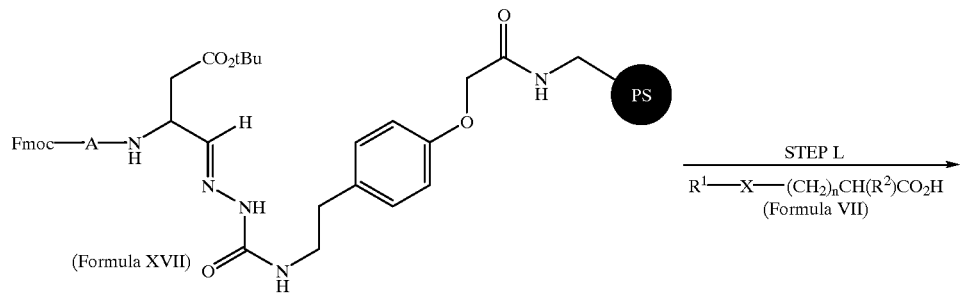

(Formula XVII)

-continued

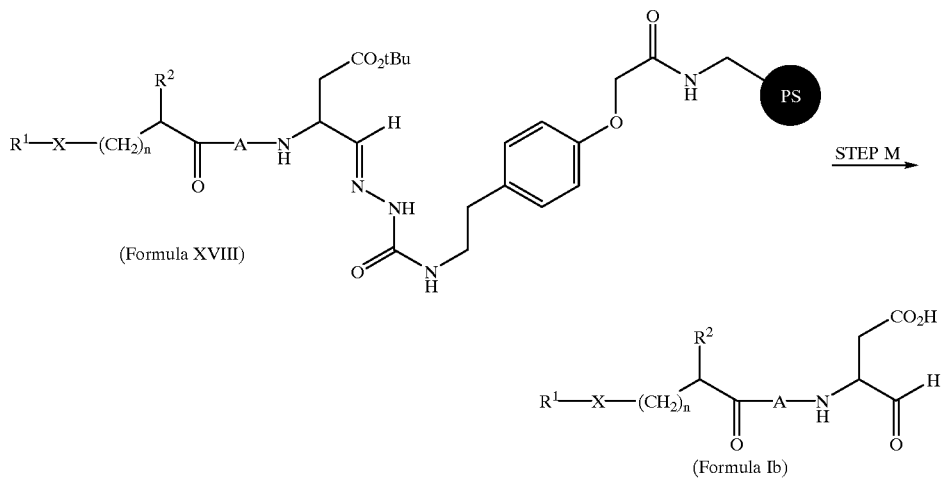

(Formula XVIII)

STEP M →

(Formula Ib)

In Scheme 3, Fmoc is the amino protecting group 9-fluorenylmethoxycarbonyl and the shaded circle labeled "PS" represents polystryene resin.

The coupling of the acid of Formula XV to a primary amine on solid support, preferably aminomethyl polystyrene, is carried out using standard peptide coupling agents, preferably using benzotriazolyloxy-tris(N-pyrolidinyl)phosphoniumhexafluorophosphate (pyBOP) in a inert solvent such as dimethylformamide or N-methyl pyrrolidone (Step J). After removal of the Fmoc protecting group of XVI by treatment with pyrrolidine-dimethylformamide, the resulting amine is coupled to Fmoc-amino acid of Formula IVa using standard peptide coupling conditions as discussed above (Step K).

In Step L the Fmoc protecting group of the compound of Formula XVII is removed again by treatment with with pyrrolidine-dimethylformamide and the resulting amine coupled to the (substituted)carboxylic acid of Formula VII again using standard peptide coupling conditions as discussed above. The tert-butyl ester of the compound of Formula XVIII is removed by treatment with trfluoroacetic acid-methylene chloride in the presence of a trapping agent such as anisole and the resulting acid cleaved from the solid support by treatment with 37% aqueous formaldehyde/acetic acid/tetrahydrofuran/trifluoroacetic acid, preferably in a ratio of 1/1/5/0.025, to give the aspartyl aldehyde of Formula Ib (Step M).

Pharmaceutical compositions of this invention comprise any of the compounds of the present invention, and pharmaceutically acceptable salts thereof, with any pharmaceutically acceptable carrier, adjuvant or vehicle (hereinafter collectively referred to as "pharmaceutically-acceptable carriers"). Pharmaceutically acceptable carriers, adjuvants and vehicles that may be used in the pharmaceutical compositions of this invention include, but are not limited to, ion exchange, alumina, aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene-polyoxypropylene-block polymers, polyethylene glycol and wool fat, and the like.

The pharmaceutical compositions of this invention may be administered orally, parenterally, by inhalation spray, topically, rectally, nasally, buccally, vaginally or by an implanted reservoir. Oral and parenteral administration are preferred. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, and aqueous suspensions and solutions. In the case of tablets for oral use, carrier which are commonly used include lactose and corn starch. Lubricating agents, such as magnesium stearate, are also typically added. For oral administration in capsule form useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable nonirritating excipient which is solid at room temperature but liquid at the rectal temperature. Such materials include, but are not limited to, cocoa butter, beeswax and polyethylene glycols.

Topical administration of the pharmaceutical compositions of this invention is especially useful when the desired treatment involves areas or organs readily accessible to topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-applied transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds of this invention may be used in combination with either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexons and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical compositions according to this invention may be comprised of a combination of a compound of Formula I and another therapeutic or prophylactic agent mentioned above.

The disease states which may be treated or prevented by the instant pharmaceutical compositions include, but are not limited to, inflammatory diseases, autoimmune diseases and neurodegenerative diseases, and for inhibiting unwanted apoptosis involved in ischemic injury, such as ischemic injury to the heart (e.g., myocardial infarction), brain (e.g., stroke), and kidney (e.g., ischemic kidney disease). As a consequence of their ability to inhibit apoptosis, the present pharmaceutical compositions are also useful for the repopulation of hematopoietic cells of a patient following chemotherapy. Methods of administering an effective amount of the above-described pharmaceutical compositions to mammals, also referred to herein as patients, in need of such treatment (that is, those suffering from inflammatory diseases, autoimmune diseases, neurodegenerative diseases and for the repopulation of hematopoietic cells in cancer patients who have undergone chemotherapy) are another aspect of the instant invention. Finally, as a further consequence of their ability to inhibit apoptosis, the instant pharmaceutical compositions may be used in a method to prolong the viability of organs to be used in transplantations.

Inflammatory disease which may be treated or prevented include, for example, septic shock, septicemia, and adult respiratory distress syndrome. Target autoimmune diseases include, for example, rheumatoid, arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, thrombocytopenia, chronic active hepatitis, myasthenia gravis and multiple sclerosis. Target neurodegenerative diseases include, for example, amyotrophic lateral sclerosis, Alzheimer's disease, Parkinson's disease, and primary lateral sclerosis. The pharmaceutical compositions of this invention may also be used to promote wound healing. Target diseases associated with harmful, apoptosis, in other words, those associated with ischemic injury, includes myocardial infarction, stroke, and ischemic kidney disease. The pharmaceutical compositions of this invention may also be used to treat infectious diseases, especially those involved with viral infections.

The term "effective amount" refers to dosage levels of the order of from about 0.05 milligrams to about 140 milligrams per kilogram of body weight per day for use in the treatment of the above-indicated conditions (typically about 2.5 milligrams to about 7 grams per patient per day). For example, inflammation may be effectively treated by the administration of from about 0.01 to 50 milligrams of the compound per kilogram of body weight per day (about 0.5 milligrams to about 3.5 grams per patient per day).

The amount of the compounds of Formula I that may be combined with the carrier materials to produce a single dosage form will vary depending upon the host treated and the particular mode of administration. For example, a formulation intended for the oral administration of humans may contain from 0.5 milligrams to 5 grams of a compound of Formula I combined with an appropriate and convenient amount of a pharmaceutically-acceptable carrier which may vary from about 5 to about 95 percent of the total composition. Dosage unit forms will generally contain between from about 1 milligram to about 500 milligrams of an active compound of Formula I.

It will be understood, however, that the specific "effective amount" for any particular patient will depend upon a variety of factors including the activity of the specific compound employed, the age, body weight, general health, sex, diet, time of administration, route of administration, rate of excretion, drug combination and the severity of the particular disease undergoing prevention or therapy.

Although this invention focuses on the use of the compounds disclosed herein for preventing and treating IL-1-mediated diseases, the compounds of this invention can also be used as inhibitory agents for other cysteine proteases.

The compounds of this invention are also useful as commercial reagents which effectively bind to the ICE/ced-3 family of cysteine protease or other cysteine proteases. As commercial reagents, the compounds of this invention, and their derivatives, may be used to block proteolysis of a target peptide or may be derivatized to bind to a stable resin as a tethered substrate for affinity chromatography applications. These and other uses which characterize commercial cystine protease inhibitors will be evident to those of ordinary skill in the art.

In order that this invention be more fully understood, the following examples are set forth. These examples are for the purpose of illustration only and are not to be construed as limiting the scope of the invention in any way.

In the following Examples, proton NMR spectra were obtained at 300 MHz; chemical shifts are quoted downfield from internal tetramethylsilane.

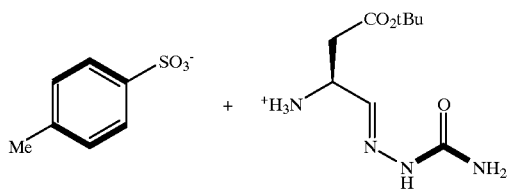

Part A

N-(Benzyloxycarbonyl)-L-(N'-Methyl-N'-Methoxy) aspartamide β-(tert-Butyl)Ester To a solution of N-(benzyloxycarbonyl)-L-aspartic acid-β-(tert-butyl)ester (14.65 g, 45.3 mmol, Bachem) in $CH_2Cl_2$ (150 mL) at 0° C. (ice bath) under a nitrogen atmosphere was added 1-hydroxybenzotriazole hydrate (7.29 g, 47.6 mmol, Aldrich) followed by 1-ethyl-3-(3',3'-dimethyl-1'-aminopropyl)carbodiimide hydrochloride (9.55 g, 49.8 mmol, Sigma). After stirring at 0° C. for 15 min., N,O-dimethylhydroxylamine hydrochloride (5.10 g, 52.3 mmol, Aldrich) and N-methylmorpholine (5.8 mL, 53 mmol, Aldrich) were added. The mixture was allowed to warm to room temperature over 3 hours then stirred at room temperature for 16 hours. The solution was concentrated under vacuum and the residue partitioned between ethyl acetate-5% $KHSO_4$ (200 mL each). The organic phase was washed in turn with 5% $KHSO_4$, saturated sodium bicarbonate and saturated sodium chloride solutions; dried over anhydrous sodium sulfate and evaporated to an oil. The oil was crystallized from hexane to give the title product (16.10 g, 97% yield) as a fluffy white crystalline solid. TLC (ethyl acetate), single spot (UV and PMA): Rf=0.37.

A similar procedure to the one above, starting with 29.3 g of N-(benzyloxycarbonyl)-L-aspartic acid-β-(tert-butyl) ester (2-fold scale up) gave 31.18 g (94% yield) of the title product.

Part B

(3S)-(Benzyloxycarbonyl)Amino-4-Oxobutanoic Acid tert-Butyl Ester Semicarbazone To a solution of N-(benzyloxycarbonyl)-L-(N'-methyl-N'-methoxy)aspartamide-β-(tert-butyl)ester (15.50 g, 42.3 mmol) in anhydrous ether (400 mL) at 0° C. (ice bath) under a nitrogen atmosphere was added dropwise to a 1.0 M solution of $LiAlH_4$ in ether (22.0 mL, 22.0 mmol, Aldrich) at such a rate as to keep the reaction solution temperature between 0–5° C. (addition time 15–20 min). After the addition of the lithium aluminum hydride reagent was complete, the mixture was stirred at 0–5° C. for 1 hr, then quenched by the dropwise addition of 0.3 N $KHSO_4$ solution (100 mL). The resultant mixture was transferred to a separatory funnel adding sufficient 5% $KHSO_4$ solution (75 mL) to dissolve the solids. The organic phase was separated and the combined aqueous washes back-extracted with ether (100 mL). The combined ether extracts were washed with saturated NaCl solution, dried over anhydrous sodium sulfate and concentrated in vacuo with minimal heating. TLC (ethyl acetate): streaky spot (UV and PMA) Rf=0.48. TLC (methanol/methylene chloride, 1:9) major spot (UV and PMA): Rf=0.75.

The crude aldehyde was immediately taken up in aqueous ethanol (45 mL water/105 mL alcohol), placed in an ice bath and treated with sodium acetate (3.82 g, 46.6 mmol) and semicarbazide hydrochloride (5.20 g, 46.6 mmol, Aldrich). The mixture was stirred at 0° C. (ice bath) under a nitrogen atmosphere for 3 hrs, allowed to warm to room temperature, and stirred overnight (16 hrs). Most of the ethanol was removed under vacuum and the residue partitioned between ethyl acetate and water (100 mL each). The organic phase was washed sequentially with 5% $KHSO_4$, saturated sodium bicarbonate and saturated sodium chloride solutions; dried over anhydrous sodium sulfate and evaporated to dryness. The crude product of this reaction was combined with that of two similar procedures starting with 15.40 g and 4.625 g of N-(benzyloxycarbonyl)-L-(N'-methyl-N'-methoxy) aspartamide-β-(tert-butyl ester) (total: 35.525 g, 97 mmol) and these combined products were purified by flash chromotagraphy on silica gel eluting with acetone/methylene chloride (3:7) then methanol-acetone-methylene chloride (0.5:3:7) to give pure title product (27.73 g, 78.5%) as a colorless foam. TLC (MeOH—$CH_2Cl_2$, 1:9): single spot (UV and PMA), Rf=0.51.

Part C

(3S)-Amino-4-Oxobutanoic Acid tert-Butyl Ester Semicarbazone, p-Toluenesulfonate Salt To a solution of (3S)-(benzyloxycarbonyl)amino-4-oxobutanoic acid tert-butyl ester semicarbazone (13.84 g, 38.0 mmol) in absolute ethanol (250 mL) was added 10% Pd/C (1.50 g, Aldrich) and the resulting mixture stirred under an atmosphere of hydrogen (balloon) until TLC (methanol/methylene chloride, 1:9) indicated complete consumption of the starting material (60 min). Note: It is important to follow this reaction closely since the product can be over-reduced. The mixture was filtered though Celite and evaporated to an oil. The oil was chased with methylene chloride (2×75 mL) then with methylene chloride/toluene (1:1, 75 mL) to give the crude amine as a white crystalline solid. TLC (EtOAc-pyridine-AcOH—$H_2O$; 60:20:5:10) single spot (UV and PMA) Rf=0.24. Note: In this TLC system, any over-reduced product will show up immediately below the desired product, Rf=0.18 (PMA only).

The crude amine was taken up in $CH_3CN$ (60 mL) and treated with a solution of p-toluenesulfonic acid monohydrate (7.22 g, 38.0 mmol) in acetonitrile (60 mL). The crystalline precipitate was collected, washed with acetonitrile and ether, and air-dried to give the title compound (13.95 g, 92% yield) as a white, crystalline solid.

The optical purity of this material was checked by conversion to the corresponding Mosher amide [1.05 equiv (R)-(−)-α-methoxy-α-(trifluoromethyl)phenylacetyl chloride, 2.1 equivalents of i-$Pr_2NEt$ in $CH_2Cl_2$, room temperature, 30 min]. The desired product has a doublet at 7.13 ppm (1H, d, J=2.4 Hz, C<u>H</u>=N) while the corresponding signal for its diastereomer is at 7.07 ppm. The optical purity of the title compound obtained from the above procedure is typically >95:5.

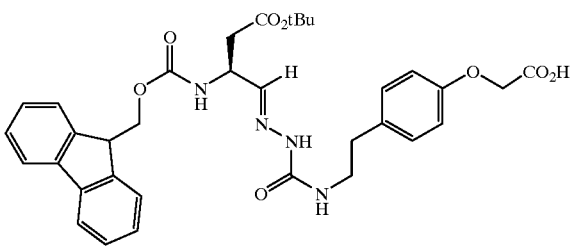

Part A

4-[2'-(N-t-Butoxycarbonyl)Aminoethyl] Phenoxyacetic Acid, Methyl Ester

To a suspension 4-hydroxy-phenethylamine (7.00 g, 51.1 mmol, Aldrich) in dry dimethylformamide (50 mL) at room temperature under nitrogen was added di-tert-butyl dicarbonate (11.0 g, 50.5 mmol). After stirring at room temperature for 1 hr, the resulting clear solution was treated with methyl bromoacetate (7.5 mL, 79 mmol) and cesium carbonate (17.5 g, 53.7 mmol). After stirring at room temperature for 16 hrs, TLC ($Et_2O$-toluene; 2:8) shows some unalkylated material remained (Rf=0.43) and a second portion of methyl bromoacetate (2.0 mL, 21 mmol) and cesium carbonate (4.5 g, 14 mmol) were added. After stirring for an additional 24 hrs, the mixture was partitioned between EtOAc-water (250 mL each), organic phase washed succesively with water (3x), 5% potassium bisulfate and saturated NaCl solutions, dried over anhydrous $Na_2SO_4$ and evaporated to dryness. Trituration of the residue with hexane gave 15.87 g of a tan solid. Filtration of the crude product through a pad of silica gel eluting with EtOAc-hexane (2:8) and crystallization from hexane gave the title compound (14.75, 93%) as a white granular, crystalline solid. TLC ($Et_2O$-toluene; 2:8) Rf=0.53.

Part B

4-(2'-Aminoethyl)Phenoxyacetic Acid, Methyl Ester, Hydrochloride

To a solution 4-[2'-(N-t-butoxycarbonyl)aminoethyl] phenoxyacetic acid, methyl ester (18.31 g, 59.3 mmol) in dioxane (55 mL) at room temperature was added 4.0 N HCl in dioxane (55 mL). After stirring at room temperature for 16 hrs, the mixture was diluted with $Et_2O$, the precipatate collected, washed throughly with $Et_2O$ and dried in vacuo to give the title compound (14.55 g, 94%) was a fluffy white, crystalline solid.

Part C

1-tert-Butoxycarbonyl-Semicarbazidyl-4-[2'-(4-Ethyl-Phenoxyacetic Acid)]Methyl Ester A solution of t-butyl carbazate (6.60 g, 50 mmol) in dimethylformamide (50 mL) was added dropwise to a solution carbonyldiimidazole (8.10 g, 50 mmol) in dimethylformamide (80 mL) over 40 min at room temperature under nitrogen. After stirring at room temperature for an additional 30 min, 4-(2'-aminoethyl)phenoxyacetic acid, methyl ester, hydrochloride (12.3 g, 50 mmol) was added as a solid in one portion followed by a triethylamine (8.0 mL, 58 mmol) added dropwise over 30 min. After stirring at room temperature for 18 hrs, the mixture was partitioned between EtOAc-water (300 mL each). The organic phase was washed succesively with water (3x), 5% potassium bisulfate, saturated sodium bicarbonate, and saturated NaCl solutions, dried over anhydrous $Na_2SO_4$ and evaporated to dryness. Crystallization of the residue from EtOAc-hexane gave the title compound (15.50, 84%) as an off-white crystalline solid. TLC (MeOH—$CH_2Cl_2$; 1:9) Rf=0.45.

Part D

1-tert-Butoxycarbonyl-Semicarbazidyl-4-[2'-(4-Ethyl-Phenoxyacetic Acid)]

A solution of 1-tert-butoxycarbonyl-semicarbazidyl-4-[2'-(4-ethyl-phenoxyacetic acid)]methyl ester (14.68 g, 40 mmol) in dioxane (50 mL) at room temperature under nitrogen was added 1.0 N LiOH solution (50 mL). After stirring at room temperature for 1 hr, the mixture was acidified with conc. HCl and extracted with EtOAc (100 mL). The organic phase was washed with saturated NaCl solution, dried over anhydrous $Na_2SO_4$ and evaporated to a white solid. Recrystallization of the crude product from THF-EtOAc-hexane gave the title compound (13.44, 95%) as a white crystalline solid. TLC (AcOH—MeOH—$CH_2Cl_2$; 1:1:8) Rf=0.31.

Part E

Semicarbazidyl-4-[2'-(4-Ethyl-Phenoxyacetic Acid)] Hydrochloride

To a solution of 1-tert-butoxycarbonyl-semicarbazidyl-4-[2'-(4-ethyl-phenoxyacetic acid)] (13.43 g, 38.0 mmol) in dioxane (80 ml)-anisole (15 mL) at room temperature was added 4.0 N HCl in dioxane (35 mL). After stirring at room temperature for 18 hrs, additional 4.0 N HCl in dioxane (15 mL) was added. After an additional 6 hrs, the precipatate was collected, washed throughly with dioxane then $Et_2O$ and dried in vacuo to give the title compound (11.67 g, 100%) was a white, crystalline solid.

Part F

N-(9-Fluorenylmethoxycarbonyl)-L-(N'-Methyl-N'-Methoxy)aspartamide β-(tert-Butyl)Ester To a solution of N-(9-fluorenylmethoxycarbonyl)-L-aspartic acid-β-(tert-butyl)ester (16.48 g, 40 mmol) in $CH_2Cl_2$ (80 ml)-tetrahydrofuran (20 mL) at 0° C. (ice bath) under a nitrogen atmosphere was added 1-hydroxybenzotriazole hydrate (7.12 g, 46.5 mmol) followed by 1-ethyl-3-(3',3'-dimethyl-1'-aminopropyl) carbodiimide hydrochloride (9.20 g, 48 mmol). After stirring at 0° C. for 15 min., N,O-dimethylhydroxylamine hydrochloride (4.68 g, 48 mmol) and N-methylmorpholine (5.2 mL, 47 mmol) were added. The mixture was allowed to warm to room temperature over 2 hours then stirred at room temperature for 16 hours. The solution was concentrated under vacuum and the residue partitioned between ethyl acetate-5% $KHSO_4$ (200 mL each). The organic phase was washed succesively with 5% $KHSO_4$, saturated sodium bicarbonate and saturated sodium chloride solutions; dried over anhydrous sodium sulfate and evaporated to an oil. Purification of the crude product by flash chromatography on silica gel eluting with EtOAc-hexane (30:70 then 35:65) gave the title product (17.75 g, 98% yield) as a colorless foam. TLC (EtOAc-hexane; 1:1) Rf=0.35.

Part G

(3S)-3-(9-Fluorenylmethoxycabonyl)Amino-4-Oxobutanoic Acid tert-Butyl Ester Semicarbazonyl-4-[2'-(4-Ethyl-Phenoxyacetic Acid)]

To a solution of N-(9-fluorenylmethoxycarbonyl)-L-(N'-methyl-N'-methoxy)aspartamide-β-(tert-butyl)ester (13.20 g, 29 mmol) in anhydrous ether (250 mL) at 0° C (ice bath) under a nitrogen atmosphere was added dropwise to a 1.0 M solution of LiAlH$_4$ in ether (14.5 mL, 14.5 mmol) at such a rate as to keep the reaction solution temperature between 0–5° C. (addition time 15–20 min). After the addition of the lithium aluminum hydride reagent was complete, the mixture was stirred at 0–5° C. for 1 hr, then quenched by the dropwise addition of 0.3 N KHSO$_4$ solution (100 mL). After adding sufficient 0.3 N KHSO$_4$ solution to dissolve most of the inorganic salts, the mixture was transferred to a seperatory funnel. The organic phase was separated and the aqueous phase back-extracted with ether (100 mL). The combined ether extracts were washed with saturated NaCl solution, dried over anhydrous sodium sulfate and concentrated in vacuo with minimal heating. TLC (EtOAc-hexane): Rf=0.40.

The crude aldehyde was immediately taken up in ethanol (105 mL)-water-(45 mL)-tetrahydrofuran(75 mL), placed in an ice bath and treated with sodium acetate (3.20 g, 39 mmol) and semicarbazidyl-4-[2'-(4-ethyl-phenoxyacetic acid)]hydrochloride (8.65 g, 30 mmol). The mixture was stirred at 0° C. (ice bath) under a nitrogen atmosphere for 3 hrs, allowed to warm to room temperature, and stirred overnight (16 hrs). The mixture was concentrated on a rotovap, diluted with water and resulting precipitate collected by suction. The material was dried in vacuo to give 18.36 g of crude product as a white solid. The crude product of this reaction was combined with that of a smaller scale reaction (6.34 g) starting with 4.55 g (10 mmol) of N-(9-fluorenylmethoxycarbonyl)-L-(N'-methyl-N'-methoxy) aspartamide-β-(tert-butyl ester) and partitioned between ethyl acetate-tetrahydrofuran(1:1) and 5% KHSO$_4$. The organic phase was washed with 5% KHSO$_4$ and saturated sodium chloride solutions, dried over anhydrous sodium sulfate and evaporated to dryness. The residue was purified by filtration through a pad of silica gel eluting with terahydrofuran/methylene chloride (1:1). The combined product-containing fractions were evaporated to dryness and recrystallized from tetrahydrofuran-Et$_2$O to give pure title product (17.01 g, 69%) as a white solid. TLC (AcOH—MeOH—CH$_2$Cl$_2$, 1:1:40): Rf=0.19.

Preparation 3

Assay for Inhibition of ICE/ced-3 Protease Family Activity

A. Determination of IC$_{50}$ Values

Fluorescence enzyme assays detecting the activity of the compounds of Formula 1 utilizing the recombinant ICE and CPP32 enzymes are performed essentially according to Thomberry et al. (*Nature*, 356:768:774 (1992)) and Nicholson et al. (*Nature*, 376:37–43 (1995)) respectively, (herein incorporated by reference) in 96 well microtiter plates. The substrate is Acetyl-Tyr-Val-Ala-Asp-amino-4-methylcoumarin (AMC) for the ICE assay and Acetyl-Asp-Glu-Val-Asp-amino-4-methylcoumarin for the CPP32, Mch2, Mch3 and Mch5 assays. Enzyme reactions are run in ICE buffer (25 mM HEPES, 1 mM EDTA, 0.1% CHAPS, 10% sucrose, pH 7.5) containing 2 mM DTT at room temperature in duplicate. The assays are performed by mixing the following components:

- 50 μL ICE, Mch2, Mch5, CPP32 (18.8, 38, 8.1 and 0.153 nM concentrations, respectively) or Mch3 (1 unit) enzyme in ICE buffer containing either 8.0 (ICE, Mch2, Mch3, CPP32) or 20 (Mch5) mM DTT;
- 50 μL compound of Formula 1 or ICE buffer (control); and
- 100 μL of 20 μM substrate.

The enzyme and the compound of Formula I to be assayed are allowed to preincubate in the microtitre plate wells for 30 minutes at room temperature prior to the addition of substrate to initiate the reaction. Fluorescent AMC product formation is monitored for one hour at room temperature by measuring the fluorescence emission at 460 nm using an excitation wavelength of 360 nm. The fluorescence change in duplicate (control) wells are averaged and the mean values are plotted as a function of inhibitor concentration to determine the inhibitor concentration producing 50% inhibition (IC$_{50}$). The results of this assay are set forth below in Table 1 and in Table 3 (for Table 3, see Examples 11 through 52).

The reference compound for this assay was Cbz-ValAlaAsp-H and the values are denoted in Table 1 as "Reference".

TABLE 1

| Ex. No. | mICE IC$_{50}$(μM) | CPP32 IC$_{50}$(μM) | MCH-2 IC$_{50}$(μM) | MCH-3 IC$_{50}$(μM) | MCH-5 IC$_{50}$(μM) |
|---|---|---|---|---|---|
| 1 | 0.535 | 0.141 | 0.995 | 1.56 | 0.680 |
| 2 | 0.336 | 0.355 | >10 | 2.10 | 1.20 |
| 3 | 2.55 | 0.021 | 0.015 | 0.587 | 0.012 |
| 4 | 4.86 | 0.0038 | 0.0035 | 0.130 | 0.031 |
| 5 | 2.96 | 0.401 | 3.61 | 10.9 | 0.733 |
| 6 | 0.385 | 0.054 | 1.43 | 1.65 | 0.048 |
| 7 | 1.89 | 0.731 | 1.90 | 17.0 | 0.200 |
| 8 | 0.033 | 0.013 | 0.037 | 1.32 | 0.0076 |
| 9 | 0.087 | 0.512 | 0.310 | 7.24 | 0.017 |
| 10 | 6.34 | 0.241 | 13.1 | 2.32 | 6.34 |
| 179 | 0.204 | 14.0 | 3.53 | >50 | 1.55 |
| 186 | 0.298 | 25.3 | >50 | >50 | 39.8 |
| 188 | 0.127 | 0.207 | 1.01 | 11.0 | 0.615 |
| reference | 0.064 | 47.0 | >10 | >10 | 2.96 |

B. Determination of the Dissociation Constant Ki and Irreversible Rate Constant k$_3$ for Irreversible Inhibitors For the irreversible inhibition of a ICE/ced-3 Family Protease enzyme with a competitive irreversible inhibitor; using the model represented by the following formulas:

$$E + I \xrightleftharpoons{K_i} EI \xrightarrow{k_3} E\text{-}I$$

$$E + S \xrightleftharpoons{K_s} ES \xrightarrow{k_s} E + S$$

The product formation at time t may be expressed as:

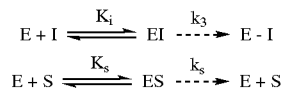

Equation 1 where E, I, EI and E-I denote the active enzyme, inhibitor, non-covalent enzyme-inhibitor complex and covalent enzyme-inhibitor adduct, respectively. The K$_i$ value is the overall dissociation constant of the reversible binding steps, and k$_3$ is the irreversible rate constant. The [S] and K$_S$ values are the substate concentration and dissociation constant of the substrate bound to the enzyme, respectively. [E]$^T$ is the total enzyme concentration.

The above equations were used to determine the K$_i$ and k$_3$ values of a given inhibitor bound to a ICE/ced-3 family protease. Thus, a continuous assay was run for sixty minutes at various concentrations of the inhibitor and the substrate. The assay was formulated essentially the same as described above for generating the data in Table 1, except that the reaction was initiated by adding the enzyme to the substrate-inhibitor mixture. The $K_i$ and $k_3$ values were obtained by simulating the product AMC formation as a function of time according to Equation 1. The results of this second assay are set forth below in Table 2.

The reference compound for this assay was Cbz-ValAlaAsp-$CH_2F$ and the values are denoted in Table 2 as "Reference". The $K_i$ values in Table 2 are in micromolar ($\mu M$). The $k_3/K_i$ values are in moles$^{-1}$ seconds$^{-1}$ ($M^{-1}s^{-1}$).

TABLE 2

| Ex. No. | mICE Ki | mICE k₃/Ki | CPP32 Ki | CPP32 k₃/Ki | MCH-2 Ki | MCH-2 k₃/Ki | MCH-5 Ki | MCH-5 k₃/Ki |
|---|---|---|---|---|---|---|---|---|
| 53 | 0.053 | 129,000 | 0.079 | 207,000 | 0.038 | 36,800 | 0.040 | 71,700 |
| 54 | 1.09 | 8,280 | 0.209 | 59,300 | 0.057 | 64,400 | 0.059 | 32,300 |
| 55 | 0.246 | 33,200 | 0.186 | 41,300 | 0.039 | 59,400 | 0.056 | 20,400 |
| 56 | 0.324 | 15,400 | 0.138 | 105,000 | 0.053 | 50,000 | 0.085 | 12,800 |
| 57 | 0.120 | 37,400 | 0.042 | 177,000 | 0.030 | 91,000 | 0.066 | 15,900 |
| 59 | 0.184 | 46,300 | 0.942 | 14,400 | 0.071 | 10,100 | 0.090 | 17,600 |
| 60 | 0.373 | 33,500 | 0.758 | 8,440 | ND | ND | 0.467 | 5,780 |
| 61 | 0.148 | 93,200 | 0.360 | 28,300 | ND | ND | 0.217 | 10,100 |
| 62 | 0.253 | 45,400 | 0.052 | 169,000 | 0.042 | 44,000 | 0.048 | 18,200 |
| 63 | 0.079 | 52,100 | 0.012 | 725,000 | 0.012 | 56,900 | 0.012 | 17,000 |
| 64 | 0.262 | 3,630 | 0.062 | 19,200 | 0.153 | 2,400 | 0.235 | 4,260 |
| 65 | 0.305 | 6,020 | 0.102 | 26,800 | 0.336 | 0 | 0.354 | 230 |
| 66 | 0.442 | 2,700 | 0.121 | 17,800 | 0.344 | 48 | 0.406 | 460 |
| 67 | 0.218 | 9,120 | 0.033 | 8,560 | 0.203 | 0 | 0.255 | 700 |
| 68 | 0.355 | 14,800 | 0.110 | 28,800 | 0.383 | 1,610 | 0.821 | 200 |
| 69 | 0.615 | 8,400 | 0.092 | 21,700 | 0.951 | 0 | 1.30 | 630 |
| 70 | 0.399 | 12,100 | 0.104 | 49,000 | 0.357 | 1,330 | 0.760 | 480 |
| 71 | 0.193 | 53,900 | 0.039 | 200,000 | 0.038 | 9,980 | 0.120 | 9,100 |
| 72 | 0.718 | 1,620 | 0.090 | 6,460 | 1.16 | 90 | 1.04 | 120 |
| 73 | 0.592 | 2,170 | 0.106 | 9,240 | 0.862 | 110 | 1.03 | 150 |
| 74 | 0.280 | 11,900 | 0.135 | 35,800 | 1.25 | 250 | 1.08 | 770 |
| 75 | 0.147 | 14,700 | 0.061 | 60,100 | 0.221 | 1,510 | 0.794 | 1,470 |
| 76 | 0.090 | 47,100 | 0.063 | 188,000 | 0.058 | 81,700 | 0.081 | 17,000 |
| 77 | 0.262 | 11,500 | 0.123 | 24,400 | 0.526 | 630 | 1.50 | 670 |
| 78 | 0.137 | 20,700 | 0.038 | 114,000 | 0.081 | 5,140 | 0.202 | 9,080 |
| 79 | 0.091 | 77,500 | 0.042 | 268,000 | 0.006 | 78,900 | 0.034 | 30,200 |
| 80 | 0.926 | 14,700 | 0.099 | 56,600 | 0.023 | 13,600 | 0.146 | 8,040 |
| 103 | 0.063 | 143,000 | 0.038 | 351,000 | 0.038 | 39,700 | 0.025 | 59,300 |
| 104 | 0.133 | 50,600 | 0.054 | 151,000 | 0.037 | 50,200 | 0.059 | 15,500 |
| 105 | 0.413 | 18,000 | 0.341 | 44,900 | 0.233 | 6,090 | 0.160 | 3,700 |
| 106 | 0.167 | 42,500 | 0.048 | 155,000 | 0.080 | 52,900 | 0.134 | 10,500 |
| 107 | 0.066 | 106,000 | 0.014 | 424,000 | 0.021 | 187,000 | 0.048 | 27,800 |
| 108 | 0.147 | 37,900 | 0.041 | 140,000 | 0.037 | 60,400 | 0.105 | 9,890 |
| 109 | 0.453 | 15,500 | 0.136 | 48,300 | 0.119 | 16,800 | 0.219 | 4,070 |
| 110 | 0.059 | 64,900 | 0.035 | 272,000 | 0.015 | 150,000 | 0.043 | 18,800 |
| 111 | 0.308 | 6,500 | 0.220 | 21,900 | 2.16 | 230 | 2.87 | 170 |
| 115 | 0.324 | 8,740 | 0.046 | 127,000 | 0.054 | 0 | 4.67 | 0 |
| 121 | 0.242 | 24,800 | 0.047 | 114,000 | 0.120 | 5,150 | 0.276 | 3,200 |
| 128 | 0.213 | 5,480 | 0.254 | 5,240 | 2.41 | 83 | 4.48 | 0 |
| 143 | 0.205 | 28,300 | 0.050 | 121,000 | 0.028 | 8,500 | 0.037 | 14,500 |
| 144 | 0.126 | 42,500 | 0.054 | 144,000 | 0.070 | 5,800 | 0.155 | 6,340 |
| 150 | 0.263 | 43,700 | 0.016 | 698,000 | 0.009 | 400,000 | 0.127 | 9,340 |
| 151 | 0.349 | 29,600 | 0.032 | 257,000 | 0.023 | 88,100 | 0.270 | 5,900 |
| 152 | 0.191 | 29,300 | 0.029 | 241,000 | 0.011 | 191,000 | 0.066 | 16,600 |
| 155 | 0.168 | 59,800 | 0.047 | 206,000 | 0.015 | 166,000 | 0.136 | 7,910 |
| 156 | 0.438 | 20,200 | 0.148 | 49,700 | 0.052 | 14,900 | 0.293 | 3,990 |
| 157 | 0.225 | 39,300 | 0.257 | 53,300 | 0.022 | 72,000 | 0.072 | 11,600 |
| 158 | 0.168 | 34,300 | 0.109 | 98,200 | 0.022 | 103,000 | 0.264 | 1,610 |
| 159 | 1.37 | 4,580 | 1.18 | 11,700 | 0.113 | 15,000 | 10.7 | 86 |
| 160 | 1.18 | 11,400 | 0.132 | 33,000 | 0.093 | 36,600 | 0.351 | 3,680 |
| 161 | 0.098 | 86,400 | 0.019 | 319,000 | 0.030 | 149,000 | 0.105 | 15,200 |
| 162 | 0.319 | 22,200 | 0.044 | 246,000 | 0.029 | 104,000 | 0.128 | 5,290 |
| 163 | 0.415 | 37,800 | 0.023 | 308,000 | 0.012 | 110,000 | 0.252 | 7,960 |
| 164 | 0.467 | 24,000 | 0.063 | 137,000 | 0.023 | 91,700 | 0.223 | 6,190 |
| 165 | 0.396 | 25,500 | 0.020 | 335,000 | 0.008 | 116,000 | 0.089 | 13,100 |
| 166 | 0.042 | 149,000 | 0.028 | 317,000 | 0.011 | 146,000 | 0.028 | 80,000 |
| 167 | 0.501 | 21,300 | 0.089 | 56,200 | 0.042 | 52,500 | 0.126 | 13,600 |
| 174 | 0.779 | 6,320 | 1.15 | 8,210 | 0.222 | 7,720 | 1.19 | 1,260 |
| 175 | 2.34 | 4,000 | 1.10 | 10,900 | 0.149 | 20,600 | 0.377 | 4,090 |
| 176 | 0.480 | 11,100 | 3.08 | 4,330 | 1.26 | 1,330 | 1.16 | 684 |
| 177 | 0.225 | 45,600 | 0.086 | 89,700 | 0.047 | 21,100 | 0.439 | 4,370 |
| refer. | 0.015 | 214,000 | 0.820 | 12,200 | 0.594 | 2,950 | 0.018 | 83,300 |

The following are examples of compounds of the invention.

EXAMPLE 1

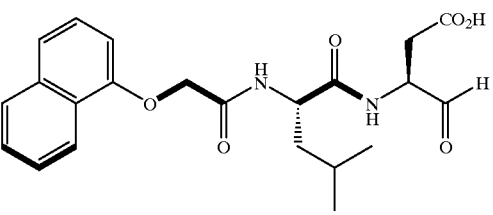

Part A (3S)-3-[(N-Benzyloxycarbonyl)Leucinyl]Amino-4-Oxobutanoic Acid tert-Butyl Ester Semicarbazone To a solution of (N-benzyloxycarbonyl)leucine N-hydroxysuccinimde ester (1.81 g, 5.0 mmol) in $CH_2Cl_2$ (30 mL) at room temperature under nitrogen was added (3S)-amino-4-oxobutanoic acid tert-butyl ester semicarbazone, p-toluenesulfonate salt (2.58 g, 6.4 mmol) followed by diisopropyl ethylamine (1.2 mL, 6.9 mmol). After stirring at room temperature for 16 hrs, the mixture was concentrated and the residue partitioned between EtOAc-5% $KHSO_4$. The organic phase was washed with 5% $KHSO_4$, saturated $NaHCO_3$ and saturated NaCl solutions, dried over anhydrous $Na_2SO_4$ and evaporated to give the title compound (2.798 g) as a pale yellow foam. TLC (MeOH—$CH_2Cl_2$; 1:9) Rf=0.52.

Part B (3S)-3-(Leucinyl)Amino-4-Oxobutanoic Acid tert-Butyl Ester Semicarbazone

To a solution of crude (3S)-[(N-benzyloxycarbonyl)leucinyl]amino-4-oxobutanoic acid tert-butyl ester semicarbazone (2.798 g, ca 5.0 mmol) in absolute EtOH (40 mL) was added 10% Pd—C (0.40 g) and resulting mixture stirred under a hydrogen atmosphere (balloon) for 1.5 hrs. The mixture was filtered through Celite washing the filter cake with $CH_2Cl_2$ and the combined filtrates evaporated to dryness. The residue was chased with $CH_2Cl_2$ (2×20 mL) to give the title product (2.113 g) as a colorless foam. TLC (MeOH—$CH_2Cl_2$; 1:9) Rf=0.23.

Part C (3S)-3-[N-((1-Naphthyloxy)Acetyl)Leucinyl]Amino-4-Oxobutanoic Acid tert-Butyl Ester Semicarbazone To a solution of (1-naphthyloxy)acetic acid (0.150 g, 0.74 mmol) and (3S)-3-(leucinyl)amino-4-oxobutanoic acid tert-butyl ester semicarbazone (0.360 g, ca 0.83 mmol) in N-methylpyrrolidone(2.0 mL)-$CH_2Cl_2$(2.0 mL) at 0° C. (ice bath) under nitrogen was added hydroxybenzotriazole hydrate (0.130 g) followed by 1-ethyl-3-(3',3'-dimethyl-1'-aminopropyl)carbodiimide hydrochloride (0.195 g, 1.02 mmol). After stirring at 0° C. for 1 hrs and at room temperature for 5 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The crude product was purified by flash chromatography eluting with MeOH—$CH_2Cl_2$ (2:100 then 5:100) to give the title compound (0.366 g, 94%) as a colorless foam, TLC(MeOH—$CH_2Cl_2$; 5:95) Rf=0.20.

Part D (3S)-3-[N-((1-Naphthyloxy)Acetyl)Leucinyl]Amino-4-Oxobutanoic Acid Semicarbazone To a solution of (3S)-3-[N-((1-naphthyloxy)acetyl)leucinyl]amino-4-oxobutanoic acid tert-butyl ester semicarbazone (0.366 g, 0.69 mmol) in $CH_2Cl_2$(2.0 mL)-anisole(0.5 mL) at room temperature under nitrogen was added trifluoroacetic acid (2.0 mL). The resulting solution was stirred at room temperature for 3 hrs, evaporated to dryness and chased with toluene-$CH_2Cl_2$ (1:1). The residue was triturated with $Et_2O$ to give the title compound (0.354 g, 100%) as an off-white solid. TLC(AcOH—MeOH—$CH_2Cl_2$; 1:1:20) Rf=0.25. TLC(EtOAc-pyridine-AcOH—$H_2O$; 60:20:5:10) R=0.48.

Part E

(3S)-3-[N-((1-Naphthyloxy)Acetyl)Leucinyl]Amino-4-Oxobutanoic Acid

A solution of (3S)-3-[N-((1-naphthyloxy)acetyl)leucinyl] amino-4-oxobutanoic acid semicarbazone (0.320 g, 0.68 mmol) in 37% aqueous formaldehyde(1.0 mL)-acetic acid (1.0 mL)-methanol(3.0 mL) was stirred at room temperature under nitrogen for 3.5 hrs. The resulting solution was diluted with water and extracted with EtOAc. The extract was washed with water and saturated NaCl solution, dried over anhydrous $Na_2SO_4$ and evaporated to dryness. The residue was taken up in EtOAc, filtered through Celite and evaporated to dryness. The product was taken up in a small amount of dioxane, diluted with water, frozen and lyophilized to give the title compound (0.222 g, 79%) as a fluffy white solid. TLC(EtOAc-pyridine-AcOH—$H_2O$; 60:20:5:10) Rf=0.65.

EXAMPLE 2

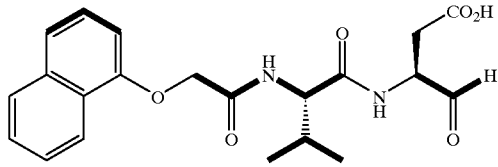

Part A

(3S)-3-[(N-Benzyloxycarbonyl)Valinyl]Amino-4-Oxobutanoic Acid tert-Butyl Ester Semicarbazone To a solution of (N-benzyloxycarbonyl)valine (2.035 g, 8.10 mmol) in $CH_2Cl_2$(80 mL) at 0° C. (ice bath) under nitrogen was added hydroxybenzotriazole hydrate (1.15 g) followed by 1-ethyl-3-(3',3'-dimethyl-1'-aminopropyl) carbodiimide hydrochloride (2.33 g, 12.2 mmol). After stirring at 0° C. for 10 min, (3S)-amino-4-oxobutanoic acid tert-butyl ester semicarbazone, p-toluenesulfonate salt (3.26 g, 8.10 mmol) followed by N-methylmorpholine (0.89 mL, 8.10 mmol) was added. After stirring at 0° C. for 2 hrs and at room temperature for 20 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The crude product was purified by flash chromatography eluting with MeOH—$CH_2Cl_2$ (2:100 then 5:100) to give the title compound (3.50 g, 93%) as a colorless foam. TLC(MeOH—$CH_2Cl_2$; 1:9) Rf=0.59.

Part B

(3S)-3-[N-((1-Naphthyloxy)Acetyl)Valinyl]Amino-4-Oxobutanoic Acid

Starting with (3S)-3-[(N-benzyloxycarbonyl)valinyl]-amino-4-oxobutanoic acid tert-butyl ester semicarbazone and follwing the general method described in Example 1, Parts B through E, the title compound was also prepared. TLC(AcOH—MeOH—$CH_2Cl_2$; 1:1:20) Rf=0.20. MS(ES) for $C_{21}H_{24}N_2O_6$ (MW 400.61): positive 401(M+H); negative 399(M−H).

EXAMPLE 3

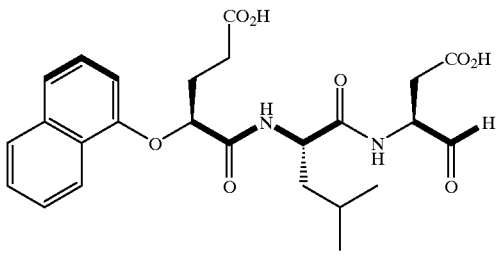

Part A

(2R)-2-Bromo-4-Carbobenzyloxy-Butyric Acid Methyl Ester

To a solution of D-glutamic acid γ-benzyl ester (5.00 g, 21 mmol) and KBr (7.5 g, 63 mmol) in 2.5N $H_2SO_4$ (35 mL) at 0° C. (ice bath) was added $NaNO_2$ (2.45 g, 35.5 mmol) in small portions over 1.5 hrs keeping the internal temperature below 5° C. The resulting mixture was stirred at 0° C. for 1 hr and at room temperature for 45 min. The mixture was extracted with $Et_2O$, extract washed with water and saturated NaCl solution, dried over anhydrous $Na_2SO_4$ and evaporated to dryness. The residue was taken up in $CH_2Cl_2$, re-dried over $Na_2SO_4$ and evaporated to dryness to give crude (2R)-2-bromo-4-carbobenzyloxy-butyric acid (5.52 g) as a colorless oil.

A portion of the crude acid (3.05 g) was taken up in $Et_2O$ (35 mL) and treated with excess diazomethane (prepared from 3.2 g of 1-methyl-3-nitro-1-nitrosoguanidine, 10 mL 40% KOH/35 ml $Et_2O$ at 0° C.) in portions at 0° C. (ice bath). When TLC indicated consumption of the acid material, the excess diazomethane was discharged with a few drops of acetic acid and the mixture was evaporated to a colorless oil. The crude product was purified by flash chromatography on silica gel eluting with $Et_2O$-hexane(1:9) to give the title compound (1.87 g, 51% overall) as a colorless liquid. TLC($Et_2O$-hexane; 35:65) Rf=0.50.

Part B

(2S)-2-(1-Naphthyloxy)-4-Carbobenzyloxy-Butyric Acid Methyl Ester

To a solution of (2R)-2-bromo-4-carbobenzyloxy-butyric acid methyl ester (1.00 g, 3.17 mmol) and 1-naphthol (0.500 g, 3.47 mmol) in dimethylformamide (4.0 mL) at room temperature under nitrogen was added powdered anhydrous $K_2CO_3$ (0.560 g, 4.7 mmol). After stirring at room temperature for 3.5 hrs, the mixture was partitioned between EtOAc-water. The organic phase was washed with water, 5% $KHSO_4$ and saturated NaCl solutions, dried over anhydrous $Na_2SO_4$ and evaporated to a yellow oil. The crude product was purified by flash chromatography on silica gel eluting with $Et_2O$-hexane(1:4) to give the title compound (1.105 g, 92%) as a pale yellow oil. TLC($Et_2O$-hexane; 3:7; 2 developments) Rf=0.33 (bromide Rf=0.52; 1-naphthol Rf=0.41).

Part C

(2S)-2-(1-Naphthyloxy)-4-Carbo(tert-Butoxy)-Butyric Acid Methyl Ester

A solution of (2S)-2-(1-naphthyloxy)-4-carbobenzyloxy-butyric acid methyl ester (1.09 g, 2.88 mmol) in MeOH (10 mL) was treated with 10% Pd—C (0.13 g) and stirred under a hydrogen atmosphere (balloon) for 1.5 hrs. The mixture was filtered through Celite washing the filter cake with $CH_2Cl_2$ and the combined filtrates evaporated to dryness. The residue was chased with toluene (10 mL) and $CH_2Cl_2$ (2×20 mL) to give the monoacid (0.889 g) as a colorless, viscous oil. TLC(MeOH—$CH_2Cl_2$; 5:95) Rf=0.25.

A solution of the crude acid (0.889 g, ca 2.88 mmol) in dry tetrahydrofuran (18 mL) at room temperature under nitrogen was treated with triethylamine (0.64 mL, 4.6 mmol) and 2,4,6-trichlorobenzoyl chloride (0.605 mL, 3.87 mmol). After stirring at room temperature for 18 hrs, the mixture was diluted with $Et_2O$, filtered through sinctered glass and evaporated to dryness. The crude mixed anhydride was taken up in $CH_2Cl_2$ (12 mL) and tert-butanol (3.5 mL), and treated with 4-dimethylaminopyridine (0.445 g, 3.65 mmol). After stirring at room temperature under nitrogen for 3.5 hrs, the mixture was concentrated and partitioned between EtOAc-5% $KHSO_4$. The organic phase was washed with 5% $KHSO_4$, saturated $NaHCO_3$ and saturated NaCl solutions, dried over anhydrous $Na_2SO_4$ and evaporated to an oil. The crude product was purified by flash chromatography eluting with $Et_2O$-hexane (1:9) to give the title compound (0.817 g, 82% overall) as a colorless, viscous oil. TLC($Et_2O$-hexane; 3:7) Rf=0.30.

Part D (3S,2'S)-3-[N-((2'-(1-Naphthyloxy)-4'-Carboxy) Butyryl)Leucinyl]Amino-4-Oxobutanoic Acid Semicarbazone Di-tert-Butyl Ester To a solution of (2S)-2-(1-naphthyloxy)-4-carbo(tert-butoxy)-butyric acid methyl ester (0.136 g, 0.395 mmol) in dioxane(1.5 mL)-water(0.5 mL) at 0° C. (ice bath) under nitrogen, was added 1.0N LiOH solution (0.52 mL, 0.52 mmol). After stirring at 0° C. for 30 min and at room temperature for 1.25 hrs, the mixture was acidified with 1.0N HCl and extracted with EtOAc. The extract was washed with saturated NaCl solution, dried over anhydrous $Na_2SO_4$ and evaporated to a colorless, viscous oil (0.143 g, theory: 0.130 g). TLC(MeOH—$CH_2Cl_2$; 1:9) Rf=0.26.

To a solution of the crude acid (0.143 g, ca 0.395 mmol) and (3S)-3-(leucinyl)amino-4-oxobutanoic acid tert-butyl ester semicarbazone (see Example 1, Part B, 0.184 g, ca 0.41 mmol) in N-methylpyrrolidone(1.0 mL)-$CH_2Cl_2$(1.0 mL) at 0° C. (ice bath) under nitrogen was added hydroxybenzotriazole hydrate (0.077 g) followed by 1-ethyl-3-(3',3'-dimethyl-1'-aminopropyl)carbodiimide hydrochloride (0.120 g, 0.626 mmol). After stirring at 0° C. for 1.5 hrs and at room temperature for 3.5 hrs, the mixture was partitioned between EtOAc-water. The organic phase was washed with water, 5% KHSO4, saturated $NaHCO_3$ and saturated NaCl solutions, dried over anhydrous $Na_2SO_4$ and evaporated to give the title compound (0.270 g, 100%) as an off-white foam. TLC(MeOH—$CH_2Cl_2$; 1:9) Rf=0.45. $^1$H-NMR(300 MHz, $CDCl_3$) reveals that the product is a 82:18 mixture of 2'S (d, 0.91 ppm, 6.3 Hz; d, 0.95 ppm, 6.0 Hz) and 2'R (d, 0.56 ppm, 6.3 Hz; d, 0.67 ppm, 6.3 Hz) diastereomers due to racemization which occurred at some point in the synthesis.

Part E (3S,2'S)-3-[N-((2'-(1-Naphthyloxy)-4'-Carboxy) Butyryl)Leucinyl]Amino-4-Oxobutanoic Acid Semicarbazone To a solution of (3S,2'S)-3-[N-((2'-(1-naphthyloxy)-4'-carboxy)butyryl)leucinyl]amino-4-oxobutanoic acid semi-carbazone di-tert-butyl ester (0.270 g, ca 0.395 mmol) in $CH_2Cl_2$(2.0 mL)-anisole(0.5 mL) at room temperature under nitrogen was added trifluoroacetic acid (2.5 mL). The resulting solution was stirred at room temperature for 4.5 hrs, evaporated to dryness and chased with $CH_2Cl_2$ and toluene-$CH_2Cl_2$ (1:1). The residue was triturated with EtOAc to give the title compound (0.171 g, 80%) as an off-white solid. Evaporation of the mother liquor and trituration of the residue with $Et_2O$ gave an additional 0.035 g of the title compound (total: 0.206 g, 96%). TLC(EtOAc-pyridine-AcOH—$H_2O$; 60:20:5:10) Rf=0.33. $^1$H-NMR(300 MHz, $CD_3OD$) of the 1st crop of material indicates that the product is a 82:18 mixture of 2'S (d, 0.88 ppm, 6.3 Hz; d, 0.95 ppm, 6.0 Hz) and 2'R (d, 0.62 ppm, 6.6 Hz; d, 0.68 ppm, 6.3 Hz) diastereomers.

Part F (3S,2'S)-3-[N-((2'-(1-Naphthyloxy)-4'-Carboxy) Butyryl)Leucinyl]Amino-4-Oxobutanoic Acid A suspension of (3S,2'S)-3-[N-((2'-(1-naphthyloxy)-4'-carboxy)butyryl)leucinyl]amino-4-oxobutanoic acid semi-carbazone (0.159 g, 0.29 mmol) in 37% aqueous formaldehyde(1.0 mL)-acetic acid(1.0 mL)-methanol(3.0 mL) was stirred at room temperature under nitrogen for 18 hrs. The resulting clear solution was diluted with water and extracted with EtOAc. The extract was washed with water and saturated NaCl solution, dried over anhydrous $Na_2SO_4$ and evaporated to dryness. The residue was taken up in tetrahydrofuran, filtered through Celite and evaporated to dryness. The product was taken up in a small amount of tetrahydrofuran and preciptated with $Et_2O$-hexane to give the title compound (0.121 g, 85%) as a white solid. TLC (EtOAc-pyridine-AcOH—$H_2O$; 60:20:5:10) Rf=0.62. $^1$H-NMR(300 MHz, $CD_3OD$) indicates that the product is a 78:22 mixture of 2'S (d, 0.88 ppm, 5.7 Hz; d, 0.95 ppm, 6.0 Hz) and 2'R (d, 0.57 ppm, 6.6 Hz; 2d's, 0.659 ppm, 6.6 Hz and 0.663 ppm, 6.6 Hz) diastereomers.

EXAMPLE 4

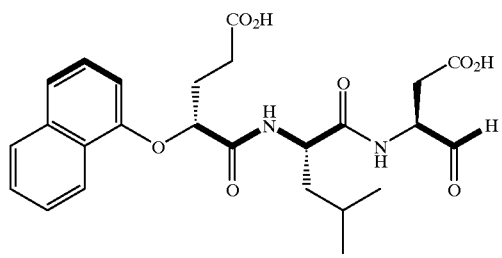

Starting with L-glutamic acid γ-benzyl ester following the method set forth in Example 3, Parts A through F, the title compound was similarly prepared. $^1$H-NMR(300 MHz, $CD_3OD$) indicates that the product is a 67:33 mixture of 2'R (d, 0.57 ppm, 6.6 Hz; 2d's, 0.659 ppm, 6.6 Hz and 0.663 ppm, 6.6 Hz) and 2'S (d, 0.88 ppm, 5.7 Hz; d, 0.95 ppm, 6.0 Hz) diastereomers.

EXAMPLE 5

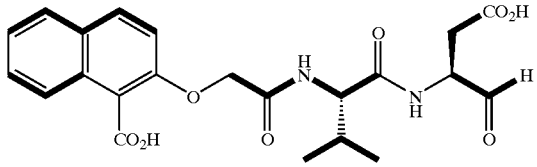

Part A (1-Carbomethoxy-2-Naphthyloxy)Acetic Acid

To a solution of 1-carbomethoxy-2-naphthol (0.382 g, 1.90 mmol) in dimethylformamide (9.4 mL) at room temperature under nitrogen was added tert-butyl bromoacetate (0.28 mL, 1.90 mmol) and powdered anhydrous potassium carbonate (0.783 g, 5.7 mmol). After stirring at room temperature for 18 hrs, the mixture was partitioned between EtOAc-water. The organic phase was washed with water (2x) and saturated NaCl solution, dried over anhydrous sodium sulfate and evaporated to an oil. TLC(EtOAc-hexane; 1:10) Rf=0.18.

The crude product (ca 1.90 mmol) was taken up in $CH_2Cl_2$ (20 mL) and treated with anisole (0.1 mL) and trifluoroacetic acid-water (9:1, 3.0 mL) at room temperature under nitrogen. After stirring at room temperature for 16 hrs, the mixture was concentrated and chased with toluene. Trituration of the residue with $Et_2O$-hexane gave the title compound (0.455 g, 92%) as a white solid.

Part B (3S)-3-[N-((1'-Carbomethoxy-2'-Naphthyloxy) Acetyl)Valinyl]Amino-4-Oxobutanoic Acid tert-Butyl Ester Semicarbazone To a solution of (1-carbomethoxy-2-naphthyloxy)acetic acid (0.260 g, 1.0 mmol) in $CH_2Cl_2$(10 mL) at 0° C. (ice bath) under nitrogen was added hydroxybenzotriazole hydrate (0.184 g) followed by 1-ethyl-3-(3',3'-dimethyl-1'-aminopropyl)carbodiimide hydrochloride (0.288 g, 1.50 mmol). After stirring for 15 min, the mixture was treated with (3S)-N-(valinyl)amino-4-oxobutanoic acid tert-butyl ester semicarbazone (0.329 g, 1.0 mmol, prepared by a method analogous to that described for N-(leucinyl)amino-4-oxobutanoic acid tert-butyl ester semicarbazone, see Example 1, Part B and Example 2, Part A) and N-methylmorpholine (0.13 mL, 1.2 mmol). After stirring at 0° C. for 2 hrs and at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to give the title compound (0.571 g, 99%) as a viscous oil. TLC(MeOH—$CH_2Cl_2$; 1:9) Rf=0.63.

Part C (3S)-3-[N-((1'-Carboxy-2'-Naphthyloxy)Acetyl) Valinyl]Amino-4-Oxobutanoic Acid tert-Butyl Ester Semicarbazone To a solution of (3S)-3-[N-((1'-carbomethoxy-2'-naphthyloxy)acetyl)valinyl]amino-4-oxobutanoic acid tert-butyl ester semicarbazone (0.571 g, 1.0 mmol) in dioxane-water (3.0 mL, 3:1, v:v) at romm temperature was added 1.0 N LiOH solution (1.1 mL, 1.1 mmol). After stirring at room temperature for 4 hrs, the mixtuure was partitioned between EtOAc-5% $KHSO_4$. The organic phase was washed with saturated NaCl solution, dried over anhydrous $Na_2SO_4$ and evaporated to dryness. Trituration with $Et_2O$-hexane gave the title compound (0.461 g, 83%) as a white solid. TLC (MeOH—$CH_2Cl_2$; 1:9) Rf=0.09.

Part D (3S)-3-[N-((1'-Carboxy-2'-Naphthyloxy)Acetyl) Valinyl]Amino-4-Oxobutanoic Acid Semicarbazone To a solution of (3S)-3-[N-((1'-carboxy-2'-naphthyloxy) acetyl)valinyl]amino-4-oxobutanoic acid tert-butyl ester semicarbazone (0.279 g, 0.50 mmol) in $CH_2Cl_2$(5.0 mL)-anisole(0.1 mL) at room temperature under nitrogen was added trifluoroacetic acid (0.85 mL). The resulting clear solution was stirred at room temperature for 16 hr, evaporated to dryness and chased with toluene-$CH_2Cl_2$ (1:1). The residue was triturated with $Et_2O$ to give the title compound (0.241 g, 96%) as an off-white solid.

Part E (3S)-3-[N-((1'-Carboxy-2'-Naphthyloxy)Acetyl) Valinyl]Amino-4-Oxobutanoic Acid A solution of (3S)-3-[N-((1'-carboxy-2'-naphthyloxy) acetyl)valinyl]amino-4-oxobutanoic acid semicarbazone (0.100 g, 0.20 mmol) in MeOH-acetic acid-37% aqueous formaldhyde (4.0 mL, 3:1:1, v:v:v), was stirred at room temperature under nitrogen for 16 hrs. The mixture was concentrated, diluted with water, frozen and lyophilized. The residue was taken up in methanol, filtered and evaporated to dryness. The residue was triturated with $Et_2O$ to give the title compound (0.070 g, 79%) as an off-white solid. MS(ES) for $C_{22}H_{24}N_2O_8$ (MW 444.44): positive 445(M+H); negative 443(M−H).

EXAMPLE 6

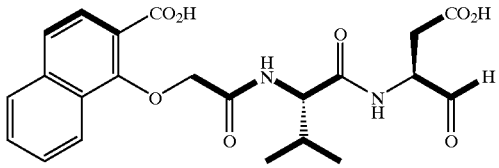

Starting with 2-carbomethoxy-1-naphthol and following the general methods described in Example 5, Parts A through E, the title compound was also prepared. MS(ES) for $C_{22}H_{24}N_2O_8$ (MW 444.44): positive 445(M+H); negative 443(M−H).

EXAMPLE 7

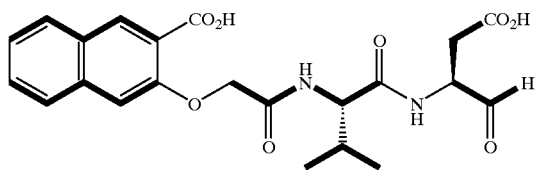

Starting with 3-carbomethoxy-2-naphthol and following the general methods described in Example 5, Parts A through E, the title compound was also prepared. MS(ES) for $C_{22}H_{24}N_2O_8$ (MW 444.44): positive 445(M+H), 483(M+K); negative 443(M−H).

EXAMPLE 8

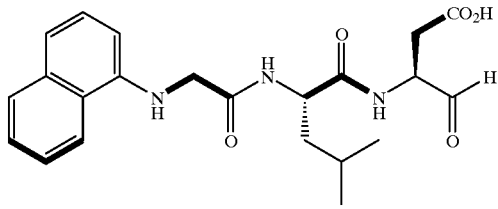

Part A

(1-Naphthylamino)Acetic Acid

To a solution of 1-aminonaphthalene (1.43 g, 10 mmol) and triethylamine (1.5 mL, 10.8 mmol) in dimethylformamide (5.0 mL) at room temperature under nitrogen was added methyl bromoacetate (1.5 mL, 15.8 mmol). After stirring at room temperature for 60 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to a purple oil (1.55 g). TLC($Et_2$O-hexane; 2:3) major spot(UV and PMA) Rf=0.41 (1-aminonaphthalene Rf=0.33).

The crude methyl ester (1.55 g) was taken up in dioxane (10 mL) and treated with 1.0N LiOH (12 mL, 12 mmol). After stirring at room temperature for 1 hr, the mixture was washed with $Et_2O$, the $Et_2O$ washes discarded, and the aqueous phase acidified with 1.0N HCl (15 mL). The resulting preciptate was collected by suction, washed with water and air-dried to give 1.35 g of crude product as a tan solid. Recrystallization fron EtOAc-hexane gave the title compound (1.03 g, 51% overall) as an off-white crystalline solid. TLC(MeOH—$CH_2Cl_2$; 1:9) Rf=0.16.

Part B

(3S)-3-[N-((1-Naphthylamino)Acetyl)Leucinyl] Amino-4-Oxobutanoic Acid tert-Butyl Ester Semicarbazone To a solution of (1-naphthylamino)acetic acid (0.076 g, 0.38 mmol) and (3S)-3-(leucinyl)amino-4-oxobutanoic acid tert-butyl ester semicarbazone (see Example 1, Part B, 0.180 g, ca 0.41 mmol) in N-methylpyrrolidone(1.0 mL)-$CH_2Cl_2$ (1.0 mL) at 0° C. (ice bath) under nitrogen was added hydroxybenzotriazole hydrate (0.075 g) followed by 1-ethyl-3-(3',3'-dimethyl-1'-aminopropyl)carbodiimide hydrochloride (0.100 g, 0.52 mmol). After stirring at 0° C. for 3 hrs and at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The crude product was purified by flash chromatography eluting with MeOH—$CH_2Cl_2$ (1:30 then 1:15) to give the title compound (0.201 g, 100%) as a pale yellow foam. TLC(MeOH—$CH_2Cl_2$; 5:95) Rf=0.29.

Part C

(3S)-3-[N-((1-Naphthylamino)Acetyl)Leucinyl] Amino-4-Oxobutanoic Acid Semicarbazone To a solution of (3S)-3-[N-((1-naphthylamino)acetyl) leucinyl]amino-4-oxobutanoic acid tert-butyl ester semicarbazone (0.201 g, 0.38 mmol) in $CH_2Cl_2$(2.0 mL)-anisole(0.5 mL) at room temperature under nitrogen was added trifluoroacetic acid (2.0 mL). The resulting solution was stirred at room temperature for 5 hrs, evaporated to dryness and chased with $CH_2Cl_2$ and toluene-$CH_2Cl_2$ (1:1). The resulting solid was triturated with $CH_2Cl_2$—$Et_2O$ to give the title compound (0.176 g, 98%) as a pale gray solid. TLC(EtOAc-pyridine-AcOH—$H_2O$; 60:20:5:10) Rf=0.45.

Part D

(3S)-3-[N-((1-Naphthylamino)Acetyl)Leucinyl] Amino-4-Oxobutanoic Acid

A solution of (3S)-3-[N-((1-naphthyloxy)acetyl)leucinyl] amino-4-oxobutanoic acid semicarbazone (0.167 g, 0.36 mmol) in 37% aqueous formaldehyde(1.0 mL)-acetic acid (1.0 mL)-methanol(3.0 mL) was stirred at room temperature under nitrogen for 4 hrs. The resulting solution was diluted with water, the resulting white preciptate collected by suction and washed with water. The solid was air-dried, triturated with $Et_2O$ and then dried in vacuo to give the title compound (0.110 g, 75%) as a light gray solid. TLC(EtOAc-pyridine-AcOH—$H_2O$; 60:20:5:10) Rf=0.54 (streaky spot). TLC(AcOH—MeOH—$CH_2Cl_2$; 1:1:8) Rf=0.25 (streaky spot).

EXAMPLE 9

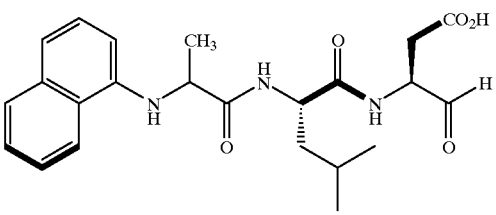

Part A

2-(1-Naphthylamino)Propionic Acid

To a solution of 1-aminonaphthalene (1.43 g, 10 mmol) and triethylamine (1.5 mL, 10.8 mmol) in dimethylformamide (3.0 mL) at room temperature under nitrogen was added ethyl 2-bromopropionate (1.4 mL, 10.8 mmol). After stirring at 60° C. (bath temperature) 18 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to a brown oil. Purification of the crude product by flash chromatography on silica gel eluting with $Et_2O$-hexane (5:95) to give ethyl 2-(1-naphthylamino)propionate (1.726 g, 73%) as a white crystalline solid after trituration with cold hexane. TLC($Et_2O$-hexane; 2:3) Rf=0.43.

The ethyl ester (1.644 g, 6.76 mmol) was taken up in dioxane (10 mL) and treated with 1.0N LiOH (10 mL, 10 mmol). After stirring at room temperature for 1.5 hrs, the mixture was acidified with 1.0N HCl (12 mL). The resulting preciptate was collected by suction, washed with water and dried in vacuo to give the title compound (1.387 g, 95%) as a white crystalline solid. TLC(MeOH—$CH_2Cl_2$; 1:9) Rf=0.38.

Part B

(3S,2'RS)-3-[N-(2'-(1-Naphthylamino)Propionyl) Leucinyl]Amino-4-Oxobutanoic Acid tert-Butyl Ester Semicarbazone To a solution of 2-(1-naphthylamino)propionic acid (0.081 g, 0.38 mmol) and (3S)-3-(leucinyl)amino-4-oxobutanoic acid tert-butyl ester semicarbazone (see Example 1, Part B, 0.180 g, ca 0.41 mmol) in N-methylpyrrolidone(1.0 mL)-CH$_2$Cl$_2$(1.0 mL) at 0° C. (ice bath) under nitrogen was added hydroxybenzotriazole hydrate (0.075 g) followed by 1-ethyl-3-(3',3'-dimethyl-1'-aminopropyl)carbodiimide hydrochloride (0.100 g, 0.52 mmol). After stirring at 0° C. for 2 hrs and at room temperature for 6 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to dryness. The crude product was purified by flash chromatography eluting with MeOH—CH$_2$Cl$_2$ (1:30 then 1:15) to give the title compound (0.197 g, 97%) as a white foam. TLC(MeOH—CH$_2$Cl$_2$; 5:95) Rf=0.35.

Part C

(3S,2'RS)-3-[N-(2'-(1-Naphthylamino)Propionyl) Leucinyl]Amino-4-Oxobutanoic Acid Semicarbazone To a solution of (3S,2'RS)-3-[N-(2'-(1-naphthylamino)-propionyl)-leucinyl]-amino-4-oxobutanoic acid tert-butyl ester semicarbazone (0.184 g, 0.34 mmol) in CH$_2$Cl$_2$(2.0 mL)-anisole(0.5 mL) at room temperature under nitrogen was added trifluoroacetic acid (2.5 mL). The resulting solution was stirred at room temperature for 6.5 hrs, evaporated to dryness and chased with CH$_2$Cl$_2$ and toluene-CH$_2$Cl$_2$ (1:1). The resulting solid was triturated with CH$_2$Cl$_2$—Et$_2$O to give the title compound (0.148 g, 90%) as a pale gray solid. TLC(EtOAc-pyridine-AcOH—H$_2$O; 60:20:5:10) two spots (diastereomers) Rf=0.36 and 0.39. TLC(AcOH—MeOH—CH$_2$Cl$_2$; 1:1:20) two spots (diastereomers) Rf=0.13 and 0.16.

Part D

(3S,2'RS)-3-[N-(2'-(1-Naphthylamino)Propionyl) Leucinyl]Amino-4-Oxobutanoic Acid A solution of (3S,2'RS)-3-[N-(2'-(1-naphthyloxy) propionyl)leucinyl]amino-4-oxobutanoic acid semicarbazone (0.138 g, 0.28 mmol) in 37% aqueous formaldehyde (0.5 mL)-acetic acid(0.5 mL)-methanol(1.5 mL) was stirred at room temperature under nitrogen for 5.5 hrs. The resulting solution was diluted with water (15 mL) and extracted with EtOAc. The extract was washed with water and saturated NaCl solution, dried over anhydrous Na$_2$SO$_4$ and evaporated to dryness. The residue was taken up in methanol (0.5 mL) and applied directly to a 3 mL Supelco™ LC-18 reverse phase extraction tube which had been pre-conditioned with water, and eluted successively with 10 mL each of water, 30% MeOH-water, 60% MeOH-water, 80% MeOH-water and 90% MeOH-water. The product-containing fractions (TLC) were combined, concentrated and the resulting aqueous mixture extracted with EtOAc. The extract was washed with saturated NaCl solution, dried over anhydrous Na$_2$SO$_4$ and evaporated to dryness. Trituration with EtOAc—Et$_2$O gave the title compound (0.098 g, 80%) as an off-white solid. TLC(EtOAc-pyridine-AcOH—H$_2$O; 60:20:5:10) Rf=0.50 (streaky spot).

EXAMPLE 10

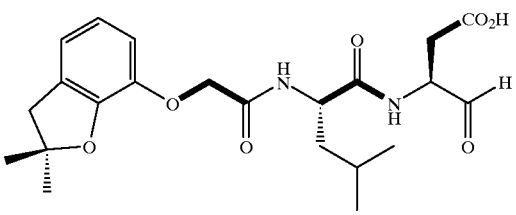

Part A

(3S)-3-[N-(9-Fluorenylmethoxycabonyl)Leucinyl] Amino-4-Oxobutanoic Acid tert-Butyl Ester Semicarbazonyl-4-[2'-(4-Ethyl-Phenoxyacetyl)] Aminomethylpolystrene Aminomethylpolystryene resin (10.0 g, 100–200 mesh, 0.71 meq/g) was placed in a 200 mL filter tube equipped with a vacuum stopcock and glass frit and washed successively with CH$_2$Cl$_2$(50 mL)dimethylformamide(50 mL), diisopropylethylamine(5 mL)dimethylformamide(30 mL), dimethylformamide (2×40 mL) and tetrahydrofuran (30 mL). The resin was suspended in tetrahydrofuran(20 mL)N-methylpyrolidinone(20 mL) with nitrogen agitation through the bottom of the frit and treated with diiospropylethylamine (1.9 mL, 10.9 mmol) and (3S)-3-(9-fluorenylmethoxycabonyl)amino-4-oxobutanoic acid tert-butyl ester semicarbazonyl-4-[2'-(4-ethyl-phenoxyacetic acid)] (2.24 g, 3.56 mmol). After all of the solid had dissolved (approx. 10 min), the mixture was treated with pyBOP [benzotriazolyloxy-tris(N-pyrolidinyl)phosphonium hexafluorophosphate, 2.78 g, 5.34 mmol) in one portion. After mixing by nitrogen agitation for 3 hrs, the supernatant was removed by suction and the resin washed succesively with tetrahydrofuran (2×50 mL), dimethylformamide (3×50 mL) and CH$_2$Cl$_2$ (2×50 mL). Unreacted amine groups were capped by treatment with a mixture of acetic anhydride(10 mL)/dimethylformamide(30 mL)/diisopropylethylamine (1.0 mL). After mixing by nitrogen agitation for 1 hr, the supernatant was removed by suction and the resin washed with dimethylformamide(4×50 mL).

The resin was treated with piperidine(10 mL)/dimethylformamide(40 mL) and mixed by nitrogen agitation for 45 min. The supernatant was removed by suction and the resin washed with dimethylformamide(4×50 mL) and tetrahydrofuran (50 mL).

The resin was suspended in tetrahydrofuran(20 mL)/N-methylpyrolidinone(20 mL), treated with N-(9-fluorenylmethoxycabonyl)leucine (2.52 g, 7.12 mmol), diisopropylethylamine (3.8 mL, 21.8 mmol) and pyBOP (5.56 g, 10.7 mmol) and mixed by nitrogen agitation for 2.5 hrs. The supernatant was removed by suction and the resin washed successively with dimethylformamide (3×40 mL) and CH$_2$Cl$_2$ (3×40 mL), methanol (2×40 mL) and Et$_2$O (2×40 mL). The resin was dried in vacuo to give the title product (12.98 g, quanitative). Based on the starting semicarbazone-acid, the resin loading was calculated as approximately 0.27 meq/g.

Part B

(3S)-3-[N-((2,3-Dihydro-2,2-Dimethyl-7-Benzofuranyloxy)Acetyl)Leucinyl]Amino-4-Oxobutanoic Acid An aliquot of the Part A resin (0.120 g, ca 0.032 mmol) was placed in a 6 mL Supelco™ fitration tube equipped with a 20 μm polyethylene frit, treated with piperidine-dimethylformamide (1.0 mL, 1:4 v/v) and mixed on an orbital shaker for 1 hr. The supernatant was removed by suction and the resin washed with dimethylformamide (4×1.0 mL) and CH$_2$Cl$_2$ (3×1.0 mL). The resin was treated with 0.5M iPr$_2$NEt in N-methylpyrolidinone (0.40 mL, 0.20 mmol), (2,3-dihydro-2,2-dimethyl-7-benzofuranyloxy) acetic acid (0.026 g, 0.12 mmol) and 0.25M pyBOP in N-methylpyrolidinone (0.40 mL, 0.10 mmol). The mixture was mixed on an orbital shaker under an nitrogen atmosphere for 16 hrs. The supernatant was removed by suction and the resin washed succesively with dimethylformamide (3×1.0 mL) and CH$_2$Cl$_2$ (3×1.0 mL), methanol (2×1.0 mL) and Et$_2$O (2×1.0 mL).

The resin was treated with 1.0 mL of CH$_2$Cl$_2$ and allowed to re-swell for 15 min. The solvent was removed by suction and the resin treated with trifluoroacetic acid-CH$_2$Cl$_2$-anisole (1.0 mL, 4:3:1 v/v/v). After mixing on an orbital shaker under nitrogen for 6 hrs, the supernatant was removed by suction and the resin washed with CH$_2$Cl$_2$ (4×1.0 mL). The resin was treated with 37% aqueous formaldehyde-acetic acid-tetrahydrofuran-trifluoroacetic acid (1.0 mL, 1:1:5:0.025 v/v/v/v) and mixed on an orbital shaker under nitrogen for 4 hrs. The supernatant was collected by suction, the resin washed with tetrahydrofuran (3×0.5 mL). The combined filtrates were blown down under nitrogen. The residue was taken up in methanol (0.5 mL), filtered and applied directly to a 3 mL Supelco™ LC-18 reverse phase extraction tube which had been pre-conditioned with water, and eluted successively with 3 mL each of 10% MeOH-water, 30% MeOH-water, 60% MeOH-water and 90% MeOH-water. The product-containing fractions (TLC) were combined and evaporated to dryness to give the title compound (0.0084 g, 60%) as a colorless glass. TLC(AcOH—MeOH—CH$_2$Cl$_2$; 1:1:20) Rf=0.29.

EXAMPLES 11–52

(Formula Ib)

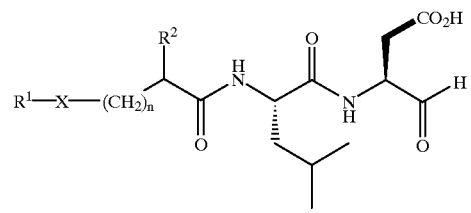

Following the general procedure set forth in Example 10, Part B; the compounds of Formula Ib (Examples 11 through 52) shown in Table 3 below are also prepared. IC$_{50}$'s were determined by the method set forth in Prepartion 3A:

TABLE 3

| Ex. No. | R$^1$ | X | n | R$^2$ | mICE I$_{50}$(μM) | CPP32 I$_{50}$(μM) | MCH2 I$_{50}$(μM) | MCH3 I$_{50}$(μM) | MCH5 I$_{50}$(μM) |
|---|---|---|---|---|---|---|---|---|---|
| 11 | 1-naphthyl | CH$_2$ | 0 | H | 1.86 | 1.59 | 4.19 | 8.78 | 12.2 |
| 12 | 1-naphthyl | O | 0 | H | 0.597 | 0.139 | 0.846 | 1.95 | 0.821 |
| 13 | 2-naphthyl | O | 0 | H | 2.57 | 0.944 | 18.6 | 8.87 | >10 |
| 14 | 1-naphthyl | O | 0 | CH$_3$ | 3.99 | 0.376 | 1.28 | 1.32 | 2.43 |
| 15 | 6-Br-1-naphthyl | O | 0 | CH$_3$ | 6.84 | 4.81 | 13.8 | 32.4 | 29.1 |
| 16 | 1-naphthyl | S | 0 | H | 2.75 | 0.195 | 1.43 | 1.74 | 7.42 |
| 17 | 2-naphthyl | S | 0 | H | 0.792 | 0.269 | 3.16 | 2.52 | 11.0 |
| 18 | 2-naphthyl | CH$_2$ | 1 | H | 1.80 | 2.76 | 14.5 | 18.2 | >50 |
| 19 | 1-naphthyl | C=O | 1 | H | 0.408 | 0.967 | 11.8 | 11.3 | 11.2 |
| 20 | 1-naphthyl | C=O | 1 | CH$_3$ | 4.55 | 9.88 | 24.9 | 29.8 | 3.25 |
| 21 | 2-naphthyl | C=O | 1 | H | 0.543 | 1.42 | 10.3 | 7.43 | 5.23 |
| 22 | 1-naphthyl | O | 1 | H | 0.686 | 0.059 | 0.305 | 1.37 | 9.81 |
| 23 | 2-naphthyl | O | 1 | H | 1.32 | 0.910 | 5.90 | 9.65 | 15.2 |
| 24 | 1-naphthyl | S | 1 | H | 0.563 | 0.412 | 2.72 | 3.60 | 16.3 |
| 25 | 2-naphthyl | S | 1 | H | 0.611 | 0.837 | 1.62 | 5.89 | 15.0 |
| 26 | 2-Me-1-naphthyl | O | 0 | H | 0.843 | 0.375 | 32.4 | 4.16 | 4.14 |
| 27 | 4-MeO-1-naphthyl | O | 0 | H | 0.831 | 0.263 | 22.6 | 4.08 | 1.45 |
| 28 | 4-Cl-1-naphthyl | O | 0 | H | 0.429 | 0.231 | 12.0 | 3.38 | 1.69 |
| 29 | 2,4-diCl-1-naphthyl | O | 0 | H | 0.141 | 0.357 | 21.4 | 3.61 | 3.04 |
| 30 | 1-isoquinolinyl | O | 0 | H | 44.2 | 1.57 | >50 | 34.7 | >50 |
| 31 | 4-quinolinyl | O | 0 | H | 35.3 | 0.232 | >50 | 4.57 | >50 |
| 32 | 5-quinolinyl | O | 0 | H | 5.25 | 0.412 | >50 | 3.85 | 4.02 |
| 33 | 5-isoquinolinyl | O | 0 | H | 5.14 | 0.407 | 42.7 | 3.48 | 3.64 |
| 34 | 8-quinolinyl | O | 0 | H | 13.7 | 0.147 | 12.5 | 1.51 | 2.24 |
| 35 | phenyl | CH$_2$ | 0 | H | >10 | 9.74 | ND | >10 | >10 |
| 36 | phenyl | O | 0 | CH$_3$ | 20.4 | 1.77 | >10 | 8.27 | >10 |
| 37 | phenyl | O | 1 | H | 9.42 | 0.419 | >50 | 6.04 | >10 |
| 38 | phenyl | O | 0 | H | >10 | 3.40 | >50 | >10 | >10 |
| 39 | 2-biphenyl | O | 0 | H | 0.636 | 0.095 | 0.717 | 2.02 | 1.71 |
| 40 | 3-biphenyl | O | 0 | H | 1.10 | 0.311 | 14.5 | 3.75 | 3.86 |
| 41 | 4-biphenyl | O | 0 | H | 1.90 | 0.763 | 20.5 | 12.0 | 7.53 |
| 42 | (2-benzyl)phenyl | O | 0 | H | 0.521 | 0.490 | 10.1 | 3.36 | 6.05 |
| 43 | (4-benzyl)phenyl | O | 0 | H | 1.80 | 0.346 | 18.9 | 4.41 | 4.72 |
| 44 | (4-phenoxy)phenyl | O | 0 | H | 2.21 | 0.545 | 21.2 | 6.82 | 9.28 |
| 45 | (2-benzyloxy)phenyl | O | 0 | H | 2.40 | 0.222 | 9.75 | 2.20 | 4.34 |
| 46 | (4-benzyloxy)phenyl | O | 0 | H | 2.51 | 0.570 | 33.4 | 7.25 | 8.60 |
| 47 | (2-cyclo-pentyl)-phenyl | O | 0 | H | 0.538 | 0.197 | 3.37 | 1.49 | 1.86 |
| 48 | (4-cyclo-pentyl)-phenyl | O | 0 | H | 2.20 | 0.319 | 51.2 | 5.23 | 5.90 |

TABLE 3-continued

| Ex. No. | R[1] | X | n | R[2] | mICE $I_{50}(\mu M)$ | CPP32 $I_{50}(\mu M)$ | MCH2 $I_{50}(\mu M)$ | MCH3 $I_{50}(\mu M)$ | MCH5 $I_{50}(\mu M)$ |
|---|---|---|---|---|---|---|---|---|---|
| 49 | [2-(1-adamantanyl)-4-Me]phenyl | O | 0 | H | 1.43 | 0.474 | 5.86 | 2.79 | 3.87 |
| 50 | 4-(1-adamantanyl)-phenyl | O | 0 | H | 1.83 | 0.528 | 32.5 | 8.24 | 4.35 |
| 51 | 5,6,7,8-tetrahydro-1-naphthyl | O | 0 | H | 1.81 | 0.324 | 11.8 | 2.74 | 1.75 |
| 52 | 5,6,7,8-tetrahydro-2-naphthyl | O | 0 | H | 2.57 | 0.162 | 28.6 | 2.31 | 4.95 |

EXAMPLE 53

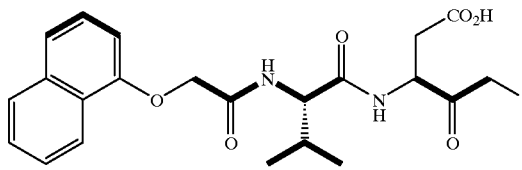

Part A

(3RS,4RS)-3-[(N-Benzyloxycarbonyl)Valinyl]Amino-5-Fluoro-4-Hydroxypentanoic Acid, tert-Butyl Ester To a solution of (N-benzyloxycarbonyl)valine (0.332 g, 1.32 mmol) in $CH_2Cl_2$(7.0 mL) at 0° C. (ice bath) under nitrogen was added hydroxybenzotriazole hydrate (0.219 g) followed by 1-ethyl-3-(3',3'-dimethyl-1'-aminopropyl)carbodiimide hydrochloride (0.317 g, 1.65 mmol). After stirring at 0° C. for 10 min, the mixture was treated with (3RS,4RS)-3-amino-5-fluoro-4-hydroxypentanoic acid, tert-butyl ester (0.228 g, 1.1 mmol, prepared as described in *Tetrahedron Letters* 1994,35, 9693–9696) and the reacton allowed to warm to room temperature. After stirring at room temperature for 24 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography eluting with EtOAc-hexane (1:1) to give the title compound (0.423 g, 87%) as colorless glass. TLC(MeOH—$CH_2Cl_2$; 5:95) Rf=0.17.

Part B

(3RS,4RS)-3-(Valinyl)Amino-5-Fluoro-4-Hydroxypentanoic Acid, tert-Butyl Ester To a solution of (3RS,4RS)-3-[(N-benzyloxycarbonyl)valinyl]amino-5-fluoro-4-hydroxypentanoic acid, tert-butyl ester (1.00 g, 2.30 mmol) in EtOH (130 mL) was added 10% Pd—C (0.120 g) and resulting mixture stirred under a hydrogen atmosphere (balloon) for 1 hr. The mixture was filtered through Celite washing the filter cake with $CH_2Cl_2$ and the combined filtrates evaporated to dryness. The residue was chased with $CH_2Cl_2$ to give the title product (0.707 g, quantitative) as a colorless oil. TLC(MeOH—$CH_2Cl_2$; 1;9) Rf=0.50.

Part C

(3RS,4RS)-3-[N-((1-Naphtyloxy)Acetyl)Valinyl]Amino-5-Fluoro-4-Hydroxypentanoic Acid, tert-Butyl Ester To a solution of (1-naphthyloxy)acetic acid (0.202 g, 1.0 mmol) in in dimethylformamide(4.0 mL) —$CH_2Cl_2$ (6.0 mL) at 0° C. (ice bath) under nitrogen was added hydroxybenzotriazole hydrate (0.168 g) followed by 1-ethyl-3-(3',3'-dimethyl-1'-aminopropyl)carbodiimide hydrochloride (0.249 g, 1.3 mmol). After stirring for 10 min, the mixture was treated with a solution of (3RS,4RS)-3-(valinyl)amino-5-fluoro-4-hydroxypentanoic acid, tert-butyl ester (0.319 g, 1.04 mmol) in $CH_2Cl_2$(8.0 mL). After stirring at 0° C. for 1 hr and at room temperature for 3 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography on silica gel eluting with EtOAc-hexane (3:2) to give the title compound (0.307 g, 63%) as a white solid. TLC(MeOH—$CH_2Cl_2$; 1:9) Rf=0.69.

Part D

(3RS)-3-[N-((1-Naphthyloxy)Acetyl)Valinyl]Amino-5-Fluoro-4-Oxopentanoic Acid, tert-Butyl Ester To a solution of (3RS,4RS)-3-[N-((1-naphthyloxy)acetyl)valinyl]amino-5-fluoro-4-hydroxypentanoic acid, tert-butyl ester (0.163 g, 0.315 mmol) and N-methylmorpholine N-oxide (0.144 g, 0.98 mmol) in $CH_2Cl_2$ (5.0 mL) at room temperature was added activated 4 Å molecular sieves. After stirring at room temperature for 20 min, the mixture was treated with tetra(n-propyl)ammonium perruthenate (0.011 g). After stirring at room temperature for 3.5 hrs, the mixture through Celite and evaporated to dryness. The residue was purified by flash chromatography on silica gel eluting with EtOAc-hexane (3:4) to give the title compound (0.124 g, 40%) as a pale yellow oil. TLC(MeOH—$CH_2Cl_2$; 1:9) Rf=0.71. $^1$H NMR (CDCl_3): δ8.27–8.23 (m, 1 H), 7.86–7.83 (m, 1 H), 7.59–7.51 (m, 3 H), 7.42–7.36 (m,1 H), 7.23–7.19 (m, 1H), 7.05–6.95 (m, 1H), 6.84 (d, 1H, J=7.7 Hz), 5.26–4.97 (m, 2 H), 4.93–4.89 (m, 1 H), 4.76 (s, 2 H), 4.45–4.35 (m, 1H), 3.05–2.76 (m, 2H), 1.42 (d, 9H, J=4.1 Hz), 1.02–0.87 (m, 6H).

Part E

(3RS)-3-[N-((1-Naphthyloxy)Acetyl)Valinyl]Amino-5-Fluoro-4-Oxopentanoic Acid To a solution of (3RS)-3-[N-((1-naphthyloxy)acetyl)valinyl]amino-5-fluoro-4-oxopentanoic acid, tert-butyl ester (0.113 g, 0.23 mmol) in $CH_2Cl_2$(2.0 mL)-anisole(0.5 mL) at room temperature under nitrogen was added trifluoroacetic acid (1.0 mL). The resulting clear solution was stirred at room temperature for 1 hr, evaporated to dryness and chased with toluene-$CH_2Cl_2$ (1:1). The residue was purified by flash chromatography on silica gel eluting with AcOH—MeOH—$CH_2Cl_2$ (0.5:2:100) to give the title compound (0.069 g, 69%) as a white solid. TLC(AcOH—MeOH—$CH_2Cl_2$; 1:1:20) Rf=0.38. MS(ES) for $C_{22}H_{25}FN_2O_6$ (MW 432.45): positive 433(M+NH); negative 431(M–H). $^1$H NMR (CD$_3$OD): δ8.32–8.29 (m, 1H), 7.82–7.79 (m, 1H), 7.49–7.46 (m, 3H), 7.38–7.32 (m, 1H), 6.88 (d, 1H, J=7.7 Hz), 4.78–4.73 (m, 2H), 4.55–4.26 (m, 2H), 2.82–2.76 (m, 2H), 2.16–2.03 (m, 1H), 0.94–0.85 (m, 6H).

EXAMPLES 54–56

Starting with (3RS,4RS)-3-(valinyl)amino-5-fluoro-4-hydroxypentanoic acid, tert-butyl ester (see Example 53, Part B) and following the methods described in Example 53, Parts C through E, the compounds shown below in Table 4 were also prepared:

TABLE 4

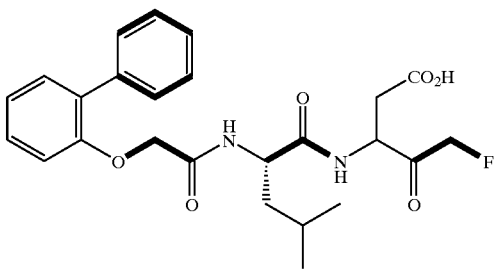

| Ex. | R$^1$ | X | n | R$^2$ | Formula | MW | MS(ES) pos. | MS(ES) neg. |
|---|---|---|---|---|---|---|---|---|
| 54 | 2-naphthyl | O | 0 | H | C$_{22}$H$_{25}$FN$_2$O$_6$ | 432.45 | 433(M + H) 455(M + Na) 471(M + K) | 431(M − H) 545(M + TFA) |
| 55 | 1-naphthyl | O | 1 | H | C$_{23}$H$_{27}$FN$_2$O$_6$ | 446.47 | 447(M + H) 489(M + Na) | 445(M − H) 559(M + TFA) |
| 56 | (2-Ph)Ph | O | 0 | H | C$_{24}$H$_{27}$FN$_2$O$_6$ | 458.49 | 481(M + Na) 497(M + K) | 457(M − H) 571(M + TFA) |

EXAMPLE 57

Part A

(3RS,4RS)-3-[(N-Benzyloxycarbonyl)Leucinyl] Amino-5-Fluoro-4-Hydroxypentanoic Acid, tert-Butyl Ester To a solution of (3RS,4RS)-3-amino-5-fluoro-4-hydroxypentanoic acid, tert-butyl ester (0.230 g, 1.1 mmol) in CH$_2$Cl$_2$ (2.0 mL) at room temperature under nitrogen was added (N-benzyloxycarbonyl)leucine, N-hydroxysuccinimde ester (0.402 g, 1.1 mmol). After stirring at room temperature for 16 hrs, the mixture was evaporated to dryness and the residue purified by flash chromatography on silica gel eluting with EtOAc-hexane (1:2) to give the title compound (0.332 g, 66%) as a colorless, viscous oil. TLC (EtOAc-hexane; 2:1) Rf=0.51.

Part B

(3RS,4RS)-3-(Leucinyl)Amino-5-Fluoro-4-Hydroxypentanoic Acid, tert-Butyl Ester, p-Toluenesulfonate Salt To a solution of (3RS,4RS)-3-[(N-benzyloxycarbonyl)leucinyl]amino-5-fluoro-4-hydroxypentanoic acid, tert-butyl ester (0.332 g, 0.734 mmol) in MeOH (100 mL) was added p-toluenesulsufonic acid hydrate (0.140 g, 0.737 mmol) and 10% Pd—C (0.033 g) and resulting mixture stirred under a hydrogen atmosphere (balloon) for 2 hrs. The mixture was filtered through Celite washing the filter cake with CH$_2$Cl$_2$ and the combined filtrates evaporated to dryness. The residue was chased with CH$_2$Cl$_2$ to give the title product (0.371 g) as a colorless foam.

Part C

(3RS)-3-[N-((2-Phenylphenoxy)Acetyl)Leucinyl] Amino-5-Fluoro-4-Oxopentanoic Acid Starting with (3RS,4RS)-3-(leucinyl)amino-5-fluoro-4-hydroxypentanoic acid, tert-butyl ester, p-toluenesulfonate salt and following the methods described in Example 53, Parts C through E utilizing (2-phenylphenoxy)acetic acid in place of (1-naphthyloxy)acetic acid in Part C, gave the title compound as a white solid. MS(ES) for C$_{25}$H$_{29}$FN$_2$O$_6$ (MW 472.51): positive 495(M+Na), 511(M+K); negative 471(M−H), 585(M+TFA).

EXAMPLE 58

Starting with (3RS,4RS)-3-(leucinyl)amino-5-fluoro-4-hydroxypentanoic acid, tert-butyl ester, p-toluenesulfonate salt and following the methods described in Example 53, Parts C through E utilizing 3-(1'-naphthyloxy)propionic acid

EXAMPLE 59

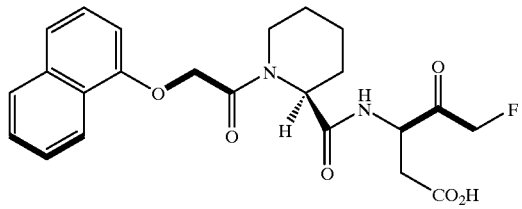

Following the general methods described in Example 53, Parts A through E, and utilizing N-(benzyloxycarbonyl)-homoproline in place of N-(benzyloxycarbonyl)valine in Part A, the title compound was also prepared. TLC(CH$_2$Cl$_2$/MeOH/AcOH, 20:1:1): Rf=0.50. $^1$H NMR (CD$_3$OD): δ8.34–8.31 (m, 1H), 7.82–7.79 (m, 1H), 7.49–7.34 (m, 4H), 6.91–6.89 (m, 1H), 5.20–3.93 (m, 6H), 3.06–2.50 (m, 2H), 2.36–2.14 (m, 2H), 1.80–1.22 (m, 6H). MS(ES) for C$_{23}$H$_{25}$FN$_2$O$_6$ (MW 444.46): positive 445(M+H); negative 443(M–H).

EXAMPLE 60

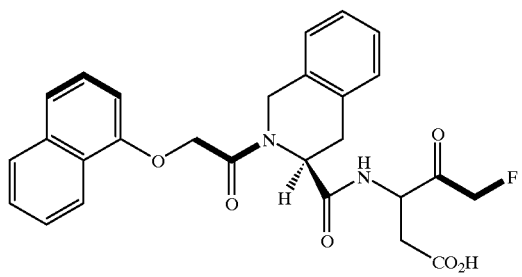

Following the general methods described in Example 53, Parts A through E, and utilizing (2S)-N-(benzyloxycarbonyl)-1,2,3,4-tetrahydroisoquinoline-2-carboxylic acid in place of N-(benzyloxycarbonyl)valine in Part A, the title compound was also prepared. MS(ES) for C$_{27}$H$_{25}$FN$_2$O$_6$ (MW 492.50): positive 493(M+H); negative 491 (M–H).

EXAMPLE 61

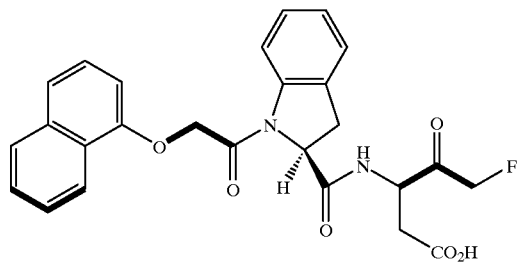

Part A (2S)-N-[(1-Naphthyloxy)Acetyl]Indoline-2'-Carboxylic Acid, Methyl Ester

To a solution of (1-naphthyloxy)acetic acid (1.119 g, 5.53 mmol) in ether (30 mL) at 0° C. was treated with phosphorus pentachloride (1.267 g, 6.08 mmol). After stirring at 0° C. for 20 min and at room temperature for 30 min, the mixture was evaporated to dyness and the residue chased with toluene (2×) to give a light-yellow oil. The crude acid chloride was taken up in toluene (10 mL) and added to a vigorously stirring mixture of methyl (S)-indoline-2-carboxylate hydrochloride (1.182 g, 5.53 mmol) in toluene (10 mL)/aqueous NaHCO$_3$ solution (2.1 g in 18 mL of H$_2$O) under N$_2$ at 0° C. The mixture was stirred for 30 min then partitioned between EtOAc and 5% KHSO$_4$. The organic phase was washed with 5% KHSO$_4$, sat'd NaHCO$_3$ (2×) and saturated NaCl solutions, dried (Na$_2$SO$_4$), and evaporated to dryness to give the title compound (1.986 g, 99%) as a white foam.

Part B (2S)-N-[(1-Naphthyloxy)Acetyl]Indoline-2-Carboxylic Acid

To a solution of (2S)-N-[(1-naphthoxy)acetyl]indoline-2-carboxylic acid methyl ester (1.0 g, 2.77 mmol) in tetrahydrofuran (3.3 mL) at 0° C. was added 1.0 N LiOH solution (3.3 mL, 3.3 mmol). After stirring at 0° C. for 2 hours the mixture was concentrated, diluted with water, acidified to pH 3, and extracted with EtOAc. The EtOAc extract was washed with saturated NaCl, dried (Na$_2$SO$_4$), and evaporated to give the title compound (0.918 g, 96%) as an off-white solid. $^1$H NMR (CD$_3$OD): δ8.36–8.33 (m, 1H), 8.15 (d, 1H, J=7.8 Hz), 7.81–7.78 (m, 1H), 7.49–7.18 (m, 7H), 7.10–7.04 (m, 1H), 6.92 (d, 1H, J=7.5 Hz), 5.32–4.94 (m, 5H), 3.69–3.34 (m, 2H).

Part C (2'S,3RS,4RS)-N-[((1-Naphthyloxy)Acetyl)Indoline-2'-Carbonyl]Amino-5-Fluoro-4-Hydroxypentanoic Acid t-Butyl Ester To a solution of (2S)-N-[(1-naphthyloxy)acetyl]-indoline-2-carboxylic acid (0.278 g, 0.8 mmol) in CH$_2$Cl$_2$ (2.0 mL)-dimethylformamide (0.5 mL) at 0° C. under nitrogen was added hydroxybenzotriazole hydrate (0.129 g) followed by 1-ethyl-3-(3',3'-dimethyl-1'-aminopropyl)carbodiimide hydrochloride (0.184 g, 0.96 mmol). After stirring at 0° C. for 10 min, a solution of (3RS,4RS)-3-amino-5-fluoro-4-hydroxypentanoic acid, tert-butyl ester (0.166 g, 0.8 mmol) in CH$_2$Cl$_2$ (3.0 mL) was added. After stirring at 0° C. for 1 hr and at room temperature for 3 hrs, the reaction mixture was partitioned between EtOAc and 5% KHSO$_4$. The organic phase was washed with 5% KHSO$_4$, saturated NaHCO$_3$ (2×) and saturated NaCl solutions, dried (Na$_2$SO$_4$), and evaporated to dryness to give the crude title compound (255 mg) as an off-white solid. TLC(CH$_2$Cl$_2$—MeOH, 9:1): Rf=0.60.

Part D (2'S,3RS)-N-[((1-Naphthyloxy)Acetyl)Indoline-2'-Carbonyl]Amino-5-Fluoro-4-Oxopentanoic Acid t-Butyl Ester To a solution of 2.0 M oxalyl chloride-CH$_2$Cl$_2$ (0.3 mL, 0.6 mmol) at −78° C. under nitrogen was added dimethyl-sulfoxide (0.09 mL, 1.2 mmol). After stirring at −78° C. for 10 min, a solution of (2'S,3RS,4RS)-N-[((1-naphthyloxy) acetyl)indoline-2'-carbonyl]amino-5-fluoro-4-hydroxypentanoic acid t-butyl ester (0.255 g, 0.48 mmol) in dry CH$_2$Cl$_2$ (3.0 mL) was added dropwise. After stirring at −78° C. for 15 min, triethylamine (0.27 mL, 2.5 mmol) was added dropwise, the mixture stirred for 10 min, then allowed to warm to room temperature. After an additional 1 hr, the mixture was partitioned between EtOAc and 5% KHSO$_4$. The organic phase was washed with 5% KHSO$_4$ and saturated NaCl solutions, dried (Na$_2$SO$_4$), and evaporated to a yellow oil. The crude product was purified by flash chromatography on silica gel eluting with EtOAc/hexane (1:2) to give the title compound (0.214 g, 83%) as a pale yellow solid. TLC(EtOAc/hexane, 1: 1): Rf=0.50.

Part E (2'S,3RS)-N-[((1-Naphthyloxy)Acetyl)Indoline-2'-Carbonyl]Amino-5-Fluoro-4-Oxopentanoic Acid To a solution of (2'S,3RS)-N-[((1-naphthyloxy)acetyl) indoline-2'-carbonyl]amino-5-fluoro-4-oxopentanoic acid t-butyl ester (0.107 g, 0.20 mmol) in anisole (0.2 mL)-CH$_2$Cl$_2$ (2.0 mL) at room temperature under nitrogen was added trifluoroacetic acid (1.0 mL). After stirring at room temperature for 1.5 hrs, the mixture was concentrated then chased with CH$_2$Cl$_2$ and toluene. The reside was triturated with ether-hexane to give the title ccompound (0.065 g, 68%) as an off-white solid. $^1$H NMR (CD$_3$OD): δ8.32–8.17 (m, 2H), 7.81–7.79 (m, 1H), 7.54–6.80 (m, 8H), 5.38–4.29 (m, 6H), 3.25–2.32 (m, 4H). MS(ES) for C$_{26}$H$_{23}$FN$_2$O$_6$ (MW 478.48): positive 479 (M+H); negative 477 (M−H).

EXAMPLE 62

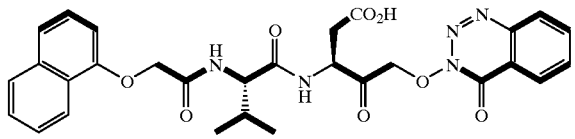

Part A

[(N-Benzyloxycarbonyl)Valinyl]Aspartic Acid, β-tert-Butyl, α-Methyl Ester

To a solution of (N-benzyloxycarbonyl)valine (2.10 g, 8.36 mmol) in CH$_2$Cl$_2$(20 mL) at 0° C. (ice bath) under nitrogen was added hydroxybenzotriazole hydrate (1.74 g) followed by 1-ethyl-3-(3',3'-dimethyl-1'-aminopropyl) carbodiimide hydrochloride (2.40 g, 12.5 mmol). After stirring at 0° C. for 10 min, the mixture was treated with aspartic acid, β-tert-butyl, α-methyl ester hydrochloride (2.00 g, 8.34 mmol) and N-methylmorpholine 1.1 mL, 10 mmol), and the reaction allowed to warm to room temperature. After stirring at room temperature for 2.5 hrs, the mixture was concentrated and the residue partitioned between EtOAc-water. The organic phase was washed with water, 5% KHSO$_4$, saturated NaHCO$_3$ and saturated NaCl solutions, dried over anhydrous Na$_2$SO$_4$ and evaporated to give the title compound (3.55 g, 97%) as a white solid after tituration with Et$_2$O-hexane. TLC(EtOAc-hexane; 1:1) Rf=0.48.

Part B

N-(Valinyl)Aspartic Acid, β-tert-Butyl, α-Methyl Ester

To a solution of [(N-benzyloxycarbonyl)valinyl]aspartic acid, β-tert-butyl, α-methyl ester (2.14 g, 4.90 mmol) in EtOH (200 mL) was added 10% Pd—C (0.21 g) and resulting mixture stirred under a hydrogen atmosphere (balloon) for 2 hrs. The mixture was filtered through Celite washing the filter cake with CH$_2$Cl$_2$ and the combined filtrates evaporated to dryness. The residue was chased with CH$_2$Cl$_2$ to give the title product (1.48 g, quantitative) as a viscous oil. The crude product was used immediately for the next step.

Part C

[N-((1-Naphthyloxy)Acetyl)Valinyl]Aspartic Acid, β-tert-Butyl, α-Methyl Ester

To a solution of (1-naphthyloxy)acetic acid (0.936 g, 4.90 mmol) in CH$_2$Cl$_2$(45 mL) at 0° C. (ice bath) under nitrogen was added hydroxybenzotriazole hydrate (0.851 g) followed by 1-ethyl-3-(3',3'-dimethyl-1'-aminopropyl)carbodiimide hydrochloride (1.33 g, 6.94 mmol). After stirring for 15 min, the mixture was treated with N-(valinyl)aspartic acid, β-tert-butyl, α-methyl ester (1.48 g, ca 4.90 mmol) and N-methylmorpholine (0.61 mL, 5.55 mmol). After stirring at 0° C. for 2 hrs and at room temperature for 16 hrs, the mixture was partitioned between EtOAc-water. The organic phase was washed with water, 5% KHSO$_4$, saturated NaHCO$_3$ and saturated NaCl solutions, dried over anhydrous Na$_2$SO$_4$ and evaporated to dryness. The residue was purified by flash chromatography on silica gel eluting with EtOAc-hexane (1:2) to give the title compound (1.89 g, 79%) as a viscous oil. TLC(EtOAc-hexane; 1:1) Rf=0.57.

Part D

[N-((1-Naphthyloxy)Acetyl)Valinyl]Aspartic Acid, β-tert-Butyl Ester

To a solution of [N-((1-naphthyloxy)acetyl)valinyl] aspartic acid, β-tert-butyl, α-methyl ester (1.88 g, 3.87 mmol) in dioxane (9.0 mL)-water (3.0 mL) was added 1.0 N LiOH solution (4.3 mL, 4.3 mmol). After stirring at room temperature for 1 hr, the mixture was acidified with 1.0 N HCl and extracted with EtOAc. The extract was washed with saturated NaCl solution, dried over anhydrous Na$_2$SO$_4$ and evaporated to give the title compound (1.82 g, quantitative) as a white solid. TLC(AcOH—MeOH—CH$_2$Cl$_2$; 1:1:20) Rf=0.65.

Part E (3S)-3-[N-((1-Naphthyloxy)Acetyl)Valinyl]Amino-5-Bromo-4-Oxopentanoic Acid tert-Butyl Ester To a solution of [N-((1-naphthyloxy)acetyl)valinyl] aspartic acid, βtert-butyl ester (3.96 g, 8.40 mmol) and N-methylmorpholine (1.48 mL, 13.5 mmol) in tetrahydrofuran (37 mL) at −10° C. (NaCl/ice bath) under nitrogen was added isobutyl chloroformate (1.63 mL, 12.6 mmol). After stirring at −10° C. for 0.5 hrs, the mixture was filtered into another ice-cooled flask and the filter cake washed with cold tetrahydrofuran (approx. 15 mL). The resulting mixed anhydride solution was treated at −10° C. with excess diazomethane/Et$_2$O solution (prepared from 3.09 g, 21 mmol of 1-methyl-3-nitro-1-nitrosoguanidine, 15 mL 40% KOH/28 mL Et$_2$O). After stirring at −10° C. for 30 min and at room temperature for 15 min, the mixture was cooled to 0° C. (ice bath) and treated with 48% aqueous HBr (19.0 mL, 170 mmol). Gas evolution was observed. After 15 min, the mixture was partitioned between EtOAc-saturated NaHCO$_3$, the organic phase washed with saturated NaCl solution, dried over anhydrous Na$_2$SO$_4$ and evaporated. Trituration of the residue with Et$_2$O gave the title compound (3.29 g, 71%) as a white solid. TLC(EtOAc-hexane; 1:1) Rf=0.51. $^1$H NMR (CDCl$_3$): δ8.26–8.22 (m, 1H), 7.86–7.83 (m, 1H), 7.59–7.51 (m, 3H), 7.41–7.36 (m, 1H), 7.27–7.20 (m, 2H), 6.83 (d, 1H, J=7.8 Hz), 5.00–4.95 (m, 1H), 4.76 (s, 2H), 4.48–4.43 (m, 1H), 4.12 (s, 2H), 2.95–2.74 (dd, 2H), 2.26–2.19 (m, 1H), 1.41 (s, 9H), 0.99 (d, 3H, J=6.9 Hz), 0.92 (d, 3H, J=6.9 Hz).

Part F (3S)-3-[N-((1-Naphthyloxy)Acetyl)Valinyl]Amino-5-(1',2',3'-Benzotriazin-4'(3H)-on-3'-yloxy)-4-Oxopentanoic Acid, tert-Butyl Ester To a solution of (3S)-3-[N-((1-naphthyloxy)acetyl) valinyl]amino-5-bromo-4-oxopentanoic acid tert-butyl ester (0.165 g, 0.30 mmol) and 3-hydroxy-1,2,3-benzotriazin-4 (3H)-one (0.059 g, 0.36 mmol) in dimethylformamide (2.0 mL) at room temperature under nitrogen was added potassium fluoride (0.061 g, 1.05 mmol). After stirring at room temperature for 5 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. Trituration of the residue with $Et_2O$-hexane gave the title compound (0.171 g, 90%) as pale yellow solid. TLC(MeOH—$CH_2Cl_2$; 1:9) Rf=0.40.

Part G

(3S)-3-[N-((1-Naphthyloxy)Acetyl)Valinyl]Amino-5-(1',2',3'-Benzotriazin-4'(3H)-on-3'-yloxy)-4-Oxopentanoic Acid To a solution of (3S)-3-[N-((1-naphthyloxy)acetyl) valinyl]amino-5-(1',2',3'-benzotriazin-4'(3H)-on-3'-yloxy)-4-oxopentanoic acid, tert-butyl ester (0.143 g, 0.23 mmol) in $CH_2Cl_2$(2.0 mL)-anisole(0.2 mL) at room temperature under nitrogen was added trifluoroacetic acid (1.0 mL). The resulting clear solution was stirred at room temperature for 2 hr, evaporated to dryness and chased with toluene-$CH_2Cl_2$ (1:1). The residue was triturated with $Et_2O$-hexane to give the title compound (0.099 g, 76%) as an off-white solid. $^1H$ NMR ($CD_3OD$): δ8.33–7.24 (m, 10H), 6.92–6.77 (m, 1H), 5.38–5.27 (m, 1H), 4.80–4.31 (m, 5H), 3.08–2.60 (m, 2H), 2.18–2.04 (m, 1H), 1.11–0.83 (m, 6H). MS(ES) for $C_{29}H_{29}N_5O_8$ (MW 575.58): positive 576(M+H); negative 574(M−H).

EXAMPLES 63–149

Starting with (3S)-3-[N-((1-naphthyloxy)acetyl)valinyl] amino-5-bromo-4-oxopentanoic acid tert-butyl ester (see Example 62, Part E) and following the methods described in Example 62, Parts F through G, the compounds shown below in Table 5 were also prepared:

TABLE 5

| Ex. | B | Formula | MW | MS(ES) pos. | MS(ES) neg. |
|---|---|---|---|---|---|
| 63 | $CH_2OCO(2,6$-diCl—Ph$)$ | $C_{29}H_{28}Cl_2N_2O_8$ | 603.45 | 603/605 (M + H) | 601/603 (M − H) |
| 64 | $CH_2OPh$ | $C_{28}H_{30}N_2O_7$ | 506.55 | 507(M + H) 529(M + Na) 545(M + K) | 505(M − H) |
| 65 | $CH_2O(2$-F—Ph$)$ | $C_{28}H_{29}FN_2O_7$ | 524.54 | 525(M + H) | 523(M − H) |
| 66 | $CH_2O(3$-F—Ph$)$ | $C_{28}H_{29}FN_2O_7$ | 524.54 | 525(M + H) | 523(M − H) |
| 67 | $CH_2O(4$-F—Ph$)$ | $C_{28}H_{29}FN_2O_7$ | 524.54 | 547(M + Na) | 523(M − H) |
| 68 | $CH_2O(2,3$-diF—Ph$)$ | $C_{28}H_{29}F_2N_2O_7$ | 542.54 | 543(M + H) 565(M + Na) | 541(M − H) 655(M + TFA) |
| 69 | $CH_2O(2,4$-diF—Ph$)$ | $C_{28}H_{29}F_2N_2O_7$ | 542.54 | 543(M + H) 565(M + Na) 581(M + K) | 541(M − H) |
| 70 | $CH_2O(2,5$-diF—Ph$)$ | $C_{28}H_{29}F_2N_2O_7$ | 542.54 | 543(M + H) 565(M + Na) 581(M + K) | 541(M − H) |
| 71 | $CH_2O(2,6$-diF—Ph$)$ | $C_{28}H_{29}F_2N_2O_7$ | 542.54 | 543(M + H) 565(M + Na) | 541(M − H) |
| 72 | $CH_2O(3,4$-diF—Ph$)$ | $C_{28}H_{29}F_2N_2O_7$ | 542.54 | 543(M + H) 581(M + K) | 541(M − H) |
| 73 | $CH_2O(3,5$-diF—Ph$)$ | $C_{28}H_{29}F_2N_2O_7$ | 542.54 | 543(M + H) 565(M + Na) 581(M + K) | 541(M − H) |
| 74 | $CH_2O(2,3,4$-triF—Ph$)$ | $C_{28}H_{27}F_3N_2O_7$ | 560.53 | 561(M + H) 583(M + Na) 599(M + K) | 559(M − H) |
| 75 | $CH_2O(2,3,5$-triF—Ph$)$ | $C_{28}H_{27}F_3N_2O_7$ | 560.53 | 561(M + H) 583(M + Na) 599(M + K) | 559(M − H) 673(M + TFA) |
| 76 | $CH_2O(2,3,6$-triF—Ph$)$ | $C_{28}H_{27}F_3N_2O_7$ | 560.53 | 561(M + H) 583(M + Na) 599(M + K) | 559(M − H) 673(M + TFA) |
| 77 | $CH_2O(2,4,5$-triF—Ph$)$ | $C_{28}H_{27}F_3N_2O_7$ | 560.53 | 561(M + H) 583(M + Na) 599(M + K) | 559(M − H) |
| 78 | $CH_2O(2,4,6$-triF—Ph$)$ | $C_{28}H_{27}F_3N_2O_7$ | 560.53 | 561(M + H) 583(M + Na) | 559(M − H) |
| 79 | $CH_2O(2,3,5,6$-tetra-Ph$)$ | $C_{28}H_{26}F_4N_2O_7$ | 578.52 | 579(M + H) 601(M + Na) 617(M + K) | 577(M − H) |

TABLE 5-continued

[Structure: 1-naphthyloxy-CH2-C(O)-NH-CH(iPr)-C(O)-NH-CH(CH2CO2H)-C(O)-B]

| Ex. | B | Formula | MW | MS(ES) pos. | MS(ES) neg. |
|---|---|---|---|---|---|
| 80 | CH$_2$O(2,3,4,5,6-pentaF—Ph) | C$_{28}$H$_{25}$F$_4$N$_2$O$_7$ | 596.51 | 619(M + Na) | 595(M − H) |
| 81 | CH$_2$O(2-CF$_3$—Ph) | C$_{29}$H$_{29}$F$_3$N$_2$O$_7$ | 574.55 | 597(M + Na) | 573(M − H) |
| 82 | CH$_2$O(3-CF$_3$—Ph) | C$_{29}$H$_{29}$F$_3$N$_2$O$_7$ | 574.55 | 597(M + Na) | 573(M − H) |
| 83 | CH$_2$O(4-CF$_3$—Ph) | C$_{29}$H$_{29}$F$_3$N$_2$O$_7$ | 574.55 | 597(M + Na) | 573(M − H) |
| 84 | CH$_2$O(3,5-diCF$_3$—Ph) | C$_{30}$H$_{28}$F$_6$N$_2$O$_7$ | 642.55 | 643(M + H) 665(M + Na) 681(M + K) | 641(M − H) |
| 85 | CH$_2$O(2-F,3-CF$_3$—Ph) | C$_{29}$H$_{28}$F$_4$N$_2$O$_7$ | 592.54 | 593(M + H) 615(M + Na) 631(M + K) | 591(M − H) |
| 86 | CH$_2$O(2,6-diCl—Ph) | C$_{28}$H$_{28}$Cl$_2$N$_2$O$_7$ | 575.44 | 575/577(M + H) | 573/575 (M − H) |
| 87 | CH$_2$O(2-NO$_2$—Ph) | C$_{28}$H$_{29}$N$_3$O$_9$ | 551.55 | 552(M + H) 574(M + Na) 590(M + K) | 550(M − H) |
| 88 | CH$_2$O(4-NO$_2$—Ph) | C$_{28}$H$_{29}$N$_3$O$_9$ | 551.55 | 552(M + H) 574(M + Na) | 550(M − H) |
| 89 | CH$_2$O(2-F,4-NO$_2$—Ph) | C$_{28}$H$_{28}$FN$_3$O$_9$ | 569.54 | 570(M + H) 592(M + Na) | 568(M − H) |
| 90 | CH$_2$O(4-CN—Ph) | C$_{29}$H$_{29}$N$_3$O$_7$ | 531.56 | 554(M + Na) | 530(M − H) |
| 91 | CH$_2$O(4-CF$_3$O—Ph) | C$_{29}$H$_{29}$F$_3$N$_2$O$_8$ | 590.55 | 591(M + H) | 589(M − H) 703(M + TFA) |
| 92 | CH$_2$O(4-H$_2$NCO—Ph) | C$_{29}$H$_{31}$N$_3$O$_8$ | 549.58 | 550(M + H) 572(M + Na) | 548(M − H) 662(M + TFA) |
| 93 | CH$_2$O(4-PhCO—Ph) | C$_{35}$H$_{34}$N$_2$O$_9$ | 610.66 | 611(M + H) 633(M + Na) | 609(M − H) |
| 94 | CH$_2$O(4-Ph—Ph) | C$_{34}$H$_{34}$N$_2$O$_7$ | 582.65 | 583(M + H) 605(M + Na) 621(M + K) | 581(M − H) 695(M + TFA) |
| 95 | CH$_2$O(4-C$_6$F$_5$-2,3,5,6-tetraF—Ph) | C$_{34}$H$_{25}$F$_9$N$_2$O$_7$ | 744.57 | 745(M + H) 767(M + Na) 783(M + K) | 743(M − H) |
| 96 | CH$_2$O(4-PhO—Ph) | C$_{34}$H$_{34}$N$_2$O$_8$ | 598.65 | 599(M + H) 621(M + Na) | 597(M − H) |
| 97 | CH$_2$O[4-(4'-CF$_3$—PhO)Ph] | C$_{35}$H$_{33}$F$_3$N$_2$O$_8$ | 666.65 | 667(M + H) 689(M + Na) | 665(M − H) |
| 98 | CH$_2$O(3-AcNH—Ph) | C$_{30}$H$_{33}$N$_3$O$_8$ | 563.61 | 564(M + H) 586(M + Na) | 562(M − H) |
| 99 | CH$_2$O(3,4-OCOS—Ph) | C$_{29}$H$_{28}$N$_2$O$_9$S | 580.61 | 581(M + H) 603(M + Na) 619(M + K) | 693(M + TFA) |
| 100 | CH$_2$O(2-pyridinyl) | C$_{27}$H$_{29}$N$_3$O$_7$ | 507.54 | 508(M + H) | 506(M − H) |
| 101 | CH$_2$O(4,5-diCl-3-pyridazinyl) | C$_{26}$H$_{26}$Cl$_2$N$_4$O$_7$ | 577.42 | 577/579(M + H) | 575/577 (M − H) 689/691 (M + TFA) |
| 102 | CH$_2$O(2-naphthyl) | C$_{32}$H$_{32}$N$_2$O$_7$ | 556.61 | 557(M + H) | 555(M − H) |
| 103 | CH$_2$OPOPh$_2$ | C$_{34}$H$_{35}$N$_2$O$_8$P | 630.63 | 631(M + H) 653(M + Na) | 629(M − H) |
| 104 | CH$_2$OPO(Me)Ph | C$_{29}$H$_{33}$N$_2$O$_8$P | 568.56 | 569(M + H) | 567(M − H) |
| 105 | CH$_2$OPOMe$_2$ | C$_{24}$H$_{31}$N$_2$O$_8$P | 506.49 | 529(M + Na) | 505(M − H) |
| 106 | CH$_2$OPO(n-hexyl)Ph | C$_{34}$H$_{43}$N$_2$O$_8$P | 638.28 | 639(M + H) 661(M + Na) 677(M + K) | 637(M − H) 751(M + TFA) |
| 107 | CH$_2$OPO(PhCH$_2$)Ph | C$_{35}$H$_{37}$N$_2$O$_8$P | 644.66 | 645(M + H) 667(M + Na) 683(M + K) | 643(M − H) 757(M + TFA) |
| 108 | CH$_2$OPO(Me)(4-F—Ph) | C$_{29}$H$_{32}$FN$_2$O$_8$P | 586.55 | 587(M + H) 609(M + Na) | 585(M − H) 699(M + TFA) |
| 109 | CH$_2$OPO(n-hexyl)(4-F—Ph) | C$_{34}$H$_{42}$FN$_2$O$_8$P | 656.69 | 679(M + Na) | 655(M − H) |
| 110 | CH$_2$OPO(Me)(1-naphthyl) | C$_{33}$H$_{35}$N$_2$O$_8$P | 618.62 | 619(M + H) 641(M + Na) | 731(M + TFA) |
| 111 | CH$_2$O(6-Me-2-pyron-4-yl) | C$_{28}$H$_{30}$N$_2$O$_9$ | 538.55 | 539(M + H) | |
| 112 | CH$_2$O(4-coumarinyl) | C$_{31}$H$_{30}$N$_2$O$_9$ | 574.59 | 575(M + H) 597(M + Na) | 537(M − H) 687(M + TFA) |

TABLE 5-continued

|     |     |     |     | MS(ES) | |
| --- | --- | --- | --- | --- | --- |
| Ex. | B | Formula | MW | pos. | neg. |
| 113 | CH$_2$O(2-Me-4-pyron-3-yl) | C$_{28}$H$_{30}$N$_2$O$_9$ | 538.55 | 539(M + H)<br>561(M + Na) | 537(M − H)<br>651(M + TFA) |
| 114 | CH$_2$O[1,2-diMe-4(1H)-pyridon-3-yl] | C$_{29}$H$_{33}$N$_3$O$_8$ | 551.59 | 552(M + H) | 550(M − H) |
| 115 | CH$_2$O(3-flavonyl) | C$_{37}$H$_{34}$N$_2$O$_9$ | 650.68 | 651(M + H) | 649(M − H) |
| 116 | CH$_2$O(4,6-diMe-2-pyrimidinyl) | C$_{28}$H$_{32}$N$_4$O$_7$ | 536.58 | 537(M + H) | 535(M − H) |
| 117 | CH$_2$O(4-CF$_3$-2-pyrimidinyl) | C$_{27}$H$_{27}$F$_3$N$_4$O$_7$ | 576.53 | 577(M + H) | 575(M − H) |
| 118 | CH$_2$S(4,6-diMe-2-pyrimidinyl) | C$_{28}$H$_{32}$N$_4$O$_6$S | 552.64 | 553(M + H)<br>575(M + Na) | 551(M − H)<br>665(M + TFA) |
| 119 | CH$_2$O(2,6-diMe-4-pyrimidinyl) | C$_{28}$H$_{32}$N$_4$O$_7$ | 536.58 | 537(M + H) | 535(M − H) |
| 120 | CH$_2$O(6-CF$_3$-4-pyrimidinyl) | C$_{27}$H$_{27}$F$_3$N$_4$O$_7$ | 576.53 | 577(M + H) | 575(M − H) |
| 121 | CH$_2$O(2-CF$_3$-4-pyrimidinyl) | C$_{27}$H$_{27}$F$_3$N$_4$O$_7$ | 576.53 | 577(M + H) | 575(M − H) |
| 122 | CH$_2$S(2-imidazolyl) | C$_{25}$H$_{28}$N$_4$O$_6$S | 512.58 | 513(M + H) | 511(M − H)<br>625(M + TFA) |
| 123 | CH$_2$S(1-Me-2-imidazolyl) | C$_{26}$H$_{30}$N$_4$O$_6$S | 526.61 | 527(M + H) | 525(M − H) |
| 124 | CH$_2$S(1H-1,2,4-triazol-3-yl) | C$_{24}$H$_{27}$N$_5$O$_6$S | 513.57 | 514(M + H) | 512(M − H) |
| 125 | CH$_2$S(4-Me-4H-1,2,4-triazol-3-yl) | C$_{25}$H$_{29}$N$_5$O$_6$S | 527.59 | 528(M + H) | 526(M − H)<br>640(M + TFA) |
| 126 | CH$_2$S(1-Me-5-tetrazolyl) | C$_{24}$H$_{28}$N$_6$O$_6$S | 528.58 | 529(M + H) | 527(M − H) |
| 127 | CH$_2$S(1-Ph-5-tetrazolyl) | C$_{29}$H$_{30}$N$_6$O$_6$S | 590.65 | 591(M + H) | 589(M − H) |
| 128 | CH$_2$S(5-Me-1,3,4-thiadiazol-2-yl) | C$_{25}$H$_{28}$N$_4$O$_6$S$_2$ | 544.64 | 545(M + H) | 543(M − H) |
| 129 | CH$_2$S(5-Ph-1,3,4-oxadiazol-2-yl) | C$_{30}$H$_{30}$N$_4$O$_7$S | 590.65 | 591(M + H)<br>613(M + Na) | 589(M − H)<br>703(M + TFA) |
| 130 | CH$_2$S(3-Ph-1,2,4-oxadiazol-5-yl) | C$_{30}$H$_{30}$N$_4$O$_7$S | 590.65 | 591(M + H) | 589(M − H) |
| 131 | CH$_2$S(4-Ph-2-thiazolyl) | C$_{31}$H$_{31}$N$_3$O$_6$S$_2$ | 605.72 | 606(M + H)<br>628(M + Na) | 604(M − H) |
| 132 | CH$_2$S(4,5-diPh-2-imidazolyl) | C$_{37}$H$_{36}$N$_4$O$_6$S | 664.77 | 665(M + H) | 663(M − H) |
| 133 | CH$_2$O(2-benzothiazolyl) | C$_{29}$H$_{29}$N$_3$O$_7$S | 563.62 | 564(M + H)<br>586(M + Na) | 562(M − H) |
| 134 | CH$_2$O(2-benzimidazolyl) | C$_{29}$H$_{30}$N$_4$O$_7$ | 546.58 | 547(M + H)<br>569(M + Na) | 545(M − H) |
| 135 | CH$_2$S(2-benzothiazolyl) | C$_{29}$H$_{29}$N$_3$O$_6$S$_2$ | 579.68 | 580(M + H) | 578(M − H) |
| 136 | CH$_2$S(2-benzimidazolyl) | C$_{29}$H$_{30}$N$_4$O$_6$S | 562.64 | 563(M + H) | 561(M − H)<br>675(M + TFA) |
| 137 | CH$_2$O(2-quinolinyl) | C$_{31}$H$_{31}$N$_3$O$_7$ | 557.60 | 558(M + H)<br>580(M + Na) | 556(M − H)<br>670(M + TFA) |
| 138 | CH$_2$O(3-isoquinolinyl) | C$_{31}$H$_{31}$N$_3$O$_7$ | 557.60 | 558(M + H) | 556(M − H) |
| 139 | CH$_2$O(1-isoquinolinyl) | C$_{31}$H$_{31}$N$_3$O$_7$ | 557.60 | 558(M + H)<br>580(M + Na) | 556(M − H)<br>670(M + TFA) |
| 140 | CH$_2$O(4-quinazolinyl) | C$_{31}$H$_{30}$N$_4$O$_7$ | 558.59 | 559(M + H) | 557(M − H) |
| 141 | CH$_2$O(8-quinolinyl) | C$_{31}$H$_{31}$N$_3$O$_7$ | 557.60 | 558(M + H) | 556(M − H)<br>670(M + TFA) |
| 142 | CH$_2$O(3-Me-4-CO$_2$Et-isoxazol-5-yl) | C$_{29}$H$_{33}$N$_3$O$_{10}$ | 583.59 | 584(M + H) | 582(M − H) |
| 143 | CH$_2$O(1-Ph-3-CF$_3$-pyrazol-5-yl) | C$_{32}$H$_{31}$F$_3$N$_4$O$_7$ | 640.61 | 641(M + H) | 639(M − H) |
| 144 | CH$_2$O(5-CO$_2$Me-isoxazol-3-yl) | C$_{27}$H$_{29}$N$_3$O$_{10}$ | 555.54 | 556(M + H)<br>578(M + Na) | 554(M − H) |
| 145 | CH$_2$O(5-iPr-isoxazol-3-yl) | C$_{28}$H$_{33}$N$_3$O$_8$ | 539.58 | 540(M + H) | 538(M − H) |
| 146 | CH$_2$O(3-benzoisoxazolyl) | C$_{29}$H$_{29}$N$_3$O$_8$ | 547.56 | 548(M + H) | 546(M − H) |
| 147 | CH$_2$O(1-Me-5-CF$_3$-pyrazol-3-yl) | C$_{27}$H$_{29}$F$_3$N$_4$O$_7$ | 578.54 | 579(M + H)<br>601(M + Na) | 577(M − H) |
| 148 | CH$_2$O(1-benzotriazolyl) | C$_{28}$H$_{29}$N$_5$O$_7$ | 547.57 | 548(M + H) | 660(M + TFA) |
| 149 | CH$_2$O(N-phthalimidyl) | C$_{30}$H$_{29}$N$_3$O$_9$ | 575.57 | 576(M + H) | 574(M + H)<br>688(M + TFA) |

EXAMPLES 150–154

Starting from N-(valinyl)aspartic acid, β-tert-butyl, α-methyl ester (see Example 62, Part B), following the general methods described in Example 62, Parts C through G and utilizing (2-phenylphenoxy)acetic acid in place of (1-naphthyloxy)acetic acid in Part C, and the appropriate acid or phenol in place of 3-hydroxy-1,2,3-benzotriazin-4 (3H)-one in Part F, the compounds shown below in Table 6 were also prepared

TABLE 6

|     |     |     |     | MS(ES) | |
| --- | --- | --- | --- | --- | --- |
| Ex. | B | Formula | MW | pos. | neg. |
| 150 | CH$_2$OCO(2,6-di-Cl—Ph) | C$_{31}$H$_{30}$Cl$_2$N$_2$O$_8$ | 629.49 | 629/631(M + H)<br>651/653(M + Na)<br>667/669(M + K) | 627/629(M − H)<br>741/743(M + TFA) |
| 151 | CH$_2$O(2,4,6-triF—Ph) | C$_{30}$H$_{29}$F$_3$N$_2$O$_7$ | 586.57 | 587(M + H)<br>609(M + Na)<br>625(M + K) | 585(M − H)<br>699(M + TFA) |
| 152 | CH$_2$O(2,3,5,6-tetraF—Ph) | C$_{30}$H$_{28}$F$_4$N$_2$O$_7$ | 604.56 | 605(M + H) | 603(M − H)<br>717(M + TFA) |
| 153 | CH$_2$OPOPh$_2$ | C$_{36}$H$_{37}$N$_2$O$_8$P | 656.67 | 679(M + Na)<br>695(M + K) | 655(M − H)<br>769(M + TFA) |
| 154 | CH$_2$OPO(Me)Ph | C$_{31}$H$_{35}$N$_2$O$_8$P | 594.60 | 617(M + Na)<br>633(M + K) | 593(M − H)<br>707(M + TFA) |

EXAMPLES 155–157

Starting from N-(valinyl)aspartic acid, β-tert-butyl, α-methyl ester (see Example 62, Part B), following the general methods described in Example 62, Parts C through G and utilizing (2-naphthyloxy)acetic acid in place of (1-naphthyloxy)acetic acid in Part C, and the appropriate acid or phenol in place of 3-hydroxy-1,2,3-benzotriazin-4(3H)-one in Part F, the compounds shown below in Table 7 were also prepared:

EXAMPLES 158–159

Starting from N-(valinyl)aspartic acid, β-tert-butyl, α-methyl ester (see Example 62, Part B), following the general methods described in Example 62, Parts C through G and utilizing 3-(1-naphthyloxy)propionic acid in place of (1-naphthyloxy)acetic acid in Part C, and the appropriate acid or phenol in place of 3-hydroxy-1,2,3-benzotriazin-4(3H)-one in Part F, the compounds shown below in Table 8 were also prepared:

TABLE 7

|     |     |     |     | MS(ES) | |
| --- | --- | --- | --- | --- | --- |
| Ex. | B | Formula | MW | pos. | neg. |
| 155 | CH$_2$OCO(2,6-di-Cl-Ph) | C$_{29}$H$_{28}$Cl$_2$N$_2$O$_8$ | 603.45 | 603/605(M + H)<br>625/627(M + Na) | 601/603(M − H)<br>715/717(M + TFA) |
| 156 | CH$_2$O(2,4,6-triF—Ph) | C$_{28}$H$_{27}$F$_3$N$_2$O$_7$ | 560.53 | 583(M + Na) | 559(M − H)<br>673(M + TFA) |
| 157 | CH$_2$O(2,3,5,6-tetraF—Ph) | C$_{28}$H$_{26}$F$_4$N$_2$O$_7$ | 578.52 | 601(M + Na) | 577(M − H)<br>891(M + TFA) |

TABLE 8

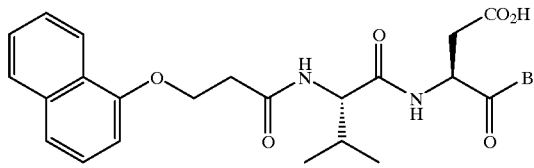

| Ex. | B | Formula | MW | MS(ES) pos. | neg. |
|---|---|---|---|---|---|
| 158 | CH$_2$OCO(2,6-di-Cl—Ph) | C$_{30}$H$_{30}$Cl$_2$N$_2$O$_8$ | 617.48 | 617/619(M + H) 639/641(M + Na) | 615/617(M − H) 729/731(M + TFA) |
| 159 | CH$_2$O(1-Ph-5-CF$_3$—pyrazol-3-yl) | C$_{33}$H$_{33}$F$_3$N$_4$O$_7$ | 654.64 | 677(M + Na) | 653(M − H) 767(M + TFA) |

EXAMPLE 160

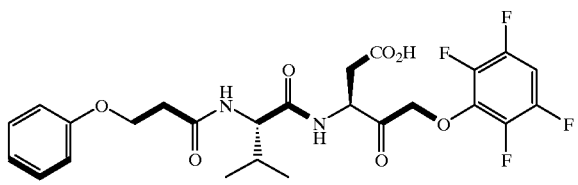

Starting from N-(valinyl)aspartic acid, β-tert-butyl, α-methyl ester (see Example 62, Part B), following the general methods described in Example 62, Parts C through G and utilizing 3-(phenoxy)propionic acid in place of (1-naphthyloxy)acetic acid in Part C, and 2,3,5,6-tetrafluorophenol in place of 3-hydroxy-1,2,3-benzotriazin-4(3H)-one in Part F, the title compound was also prepared. MS(ES) for C$_{25}$H$_{26}$F$_4$N$_2$O$_7$ (MW 542.48): positive 543(M+H), 565(M+Na), 581(M+K); negative 541(M−H).

EXAMPLE 161

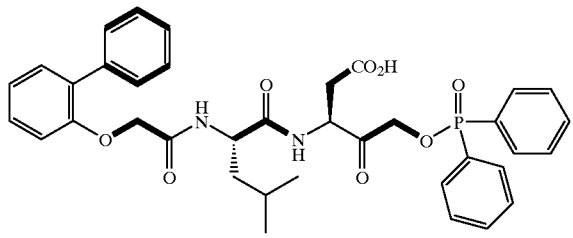

Part A

[(N-Benzyloxycarbonyl)Leucinyl]Aspartic Acid, β-tert-Butyl, α-Methyl Ester

To a solution of (N-benzyloxycarbonyl)leucine, N-hydroxysuccinimide ester (4.54 g, 12.5 mmol) and aspartic acid, β-tert-butyl, α-methyl ester hydrochloride (3.00 g, 12.5 mmol) in CH$_2$Cl$_2$ (20 mL) at room temperature under nitrogen was added N-methylmorpholine (1.65 mL, 15 mmol). After stirring at room temperature for 18 hrs, the mixture was partitioned between EtOAc-water. The organic phase was washed with 5% KHSO$_4$, saturated NaHCO$_3$ and saturated NaCl solutions, dried over anhydrous Na$_2$SO$_4$ and evaporated to give the title compound (5.56 g, 99%) as viscous oil. TLC(EtOAc-hexane; 1:1) Rf=0.48.

Part B (3S)-3-[N-((2-Phenoxyphenyl)Acetyl)Leucinyl]Amino-5-(Diphenylphosphinyloxy)-4-Oxopentanoic Acid Starting with [(N-benzyloxycarbonyl)leucinyl]aspartic acid, β-tert-butyl, α-methyl ester and following the methods described in Example 62, Parts B through G, utilizing (2-phenylphenoxy)acetic acid in place of (1-naphthyloxy)acetic acid in Part C, and the diphenylphosphinic acid in place of 3-hydroxy-1,2,3-benzotriazin-4(3H)-one in Part F, the title compound was also prepared. MS(ES) for C$_{37}$H$_{39}$N$_2$O$_8$P (MW 670.70): positive 671(M+H), 693(M+Na); negative 669(M−H), 783(M+TFA).

EXAMPLES 162–164

Starting with [(N-benzyloxycarbonyl)leucinyl]aspartic acid, β-tert-butyl, α-methyl ester (see Example 161, Part A) and following the methods described in Example 62, Parts B through G, utilizing (2-phenylphenoxy)acetic acid in place of (1-naphthyloxy)acetic acid in Part C, and the appropriate acid or phenol in place of 3-hydroxy-1,2,3-benzotriazin-4(3H)-one in Part F, the compounds shown in Table 9 were also prepared.

TABLE 9

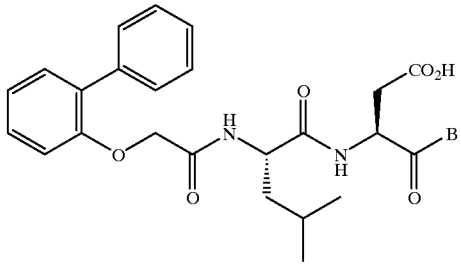

| Ex. | B | Formula | MW | MS(ES) pos. | MS(ES) neg. |
|---|---|---|---|---|---|
| 162 | CH$_2$OCO(2,6-di-Cl—Ph) | C$_{32}$H$_{32}$Cl$_2$N$_2$O$_8$ | 643.52 | 665/667(M + Na) | 641/643(M − H)<br>755/757(M + TFA) |
| 163 | CH$_2$O(2,4,6-triF—Ph) | C$_{31}$H$_{31}$F$_3$N$_2$O$_7$ | 600.60 | 623(M + Na) | 599(M − H)<br>713(M + TFA) |
| 164 | CH$_2$O(2,3,5,6-tetraF—Ph) | C$_{31}$H$_{30}$F$_4$N$_2$O$_7$ | 618.59 | 641(M + Na) | 731(M + TFA) |

EXAMPLE 165

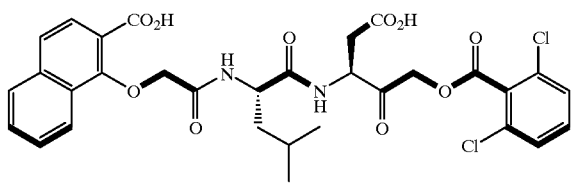

Part A (2-Carbo-tert-Butoxy-1-Naphthyloxy)Acetic Acid

To a suspension of 1-hydroxy-2-naphthoic acid (4.91 g, 26.1 mmol) in toluene (40 mL) at 80° C. (bath temp) under nitrogen was added dimethylformamide di-tert-butyl acetal (25.0 mL, 104.3 mmol) dropwise over 10 min. After stirring at 80° C. for an additional 30 min, the cooled mixture was diluted with Et$_2$O, washed successively with water, saturated NaHCO$_3$ and saturated NaCl solutions, dried over anhydrous Na$_2$SO$_4$ and concentrated. The crude product was combined with that of a smaller run starting with 0.196 g of 1-hydroxy-2-naphthoic acid (total: 5.106 g, 27 mmol) and purified by flash chromatography on silica gel eluting with EtOAc-hexane (5:95) to give 2-carbo-tert-butoxy-1-naphthol (5.52 g, 83%) as a colorless oil. TLC(EtOAc-hexane; 1:9) Rf=0.68.

To a solution of 2-carbo-tert-butoxy-1-naphthol (4.00 g, 16.4 mmol) in dimethylformamide (16 mL) at room temperature under nitrogen was added methyl bromoacetate (1.7 mL, 18 mmol) and potassium fluoride (2.85 g, 49 mmol). After stirring at room temperature for 16 hrs, TLC showed the reaction was still incomplete. Potassium carbonate (3.0 g, 21.7 mmol) and additional methyl bromoacetate (1.5 mL, 15.8 mmol) were added and the mixture heated to 60° C. (bath temp). After heating at 60° C. for 1 hr, the mixture was partitioned between EtOAc-water. The organic phase was washed with water (2×) and saturated NaCl solution, dried over anhydrous sodium sulfate and evaporated to an oil (6.17 g). TLC(EtOAc-hexane; 5:95) Rf=0.18.

The above crude product (6.17 g, ca 16.4 mmol) was taken up in dioxane (100 mL) and treated with 1.0 N LiOH solution (33 mL, 33 mmol). After stirring at room temperature for 1 hr, 100 mL of 1.0 N NaOH was added and the mixture washed with Et$_2$O. The aqueous phase was acidified (pH 2) with conc HCl and extracted with EtOAc. The EtOAc extract was washed with saturated NaCl solution, dried over anhydrous sodium sulfate and evaporated to give the title compound as a viscous oil (6.02 g). The crude product is used without further purification.

Part B (3S)-3-[N-((2'-Carboxy-1'-Naphthyloxy)Acetyl)-Leucinyl]Amino-5-(2',6'-Dichlorobenzoyloxy)-4-Oxopentanoic Acid Starting with [(N-benzyloxycarbonyl)leucinyl] aspartic acid, b-tert-butyl, a-methyl ester (see Example 161, Part A) and following the methods described in Example 62, Parts B through G, utilizing (2-carbo-tert-butoxy-1-naphthyloxy)acetic acid in place of (1-naphthyloxy)acetic acid in Part C, and 2,6-dichlorobenzoic acid in place of 3-hydroxy-1,2,3-benzotriazin-4(3H)-one in Part F, the title compound was prepared. MS(ES) for C$_{31}$H$_{30}$Cl$_2$N$_2$O$_{10}$ (MW 661.49): positive 661/663(M+H), 683/685(M+Na), 699/701(M+Na); negative 659/661(M−H).

EXAMPLES 166–167

Starting with [(N-benzyloxycarbonyl)leucinyl]aspartic acid, β-tert-butyl, α-methyl ester (see Example 161, Part A) and following the methods described in Example 62, Parts B through G, utilizing (2-carbo-tert-butoxy-1-naphthyloxy)acetic acid in place of (1-naphthyloxy)acetic acid in Part C, and the appropriate acid or phenol in place of 3-hydroxy-1,2,3-benzotriazin-4(3H)-one in Part F, the compounds shown in Table 10 were also prepared.

TABLE 10

| Ex. | B | Formula | MW | MS(ES) pos. | MS(ES) neg. |
|---|---|---|---|---|---|
| 166 | $CH_2OPOPh_2$ | $C_{36}H_{37}N_2O_{10}P$ | 688.67 | 689(M + H) | 687(M − H) |
| 167 | $CH_2O(2,3,5,6\text{-tetraF—Ph})$ | $C_{30}H_{28}F_4N_2O_9$ | 636.55 | 637(M + H) 659(M + Na) 675(M + K) | 635(M − H) |

EXAMPLE 168

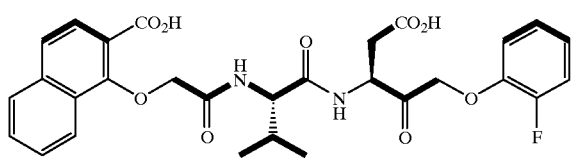

Part A

N-((2-Carbo-tert-Butoxy-1-Naphthyloxy)Acetyl) Valine Methyl Ester

To a solution of (2-carbo-tert-butoxy-1-naphthyloxy) acetic acid (1.20 g, 3.97 mmol, see Example 165, Part A) and valine methyl ester hydrochloride (0.932 g, 5.56 mmol) in N-methylpyrrolidone(7.5 mL)-$CH_2Cl_2$(7.5 mL) at room temperature under nitrogen was added O-(7-azabenzotriazol-1-yl)-N,N,N',N'-tetramethyluronium hexafluorophate (2.11 g, 5.56 mmol) and diisopropylethylamine (2.42 mL, 13.9 mmol). After stirring at room temperature for 3.5 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography on silica gel eluting with EtOAc-hexane (1:9 to 3:7) to give the title compound (1.40 g, 85%) as a colorless oil. TLC (EtOAc-hexane; 1:1) Rf=0.76.

Part B

N-[N'-((2-Carbo-tert-Butoxy-1-Naphthyloxy)Acetyl) Valinyl]Aspartic acid, β-tert-Butyl, α-Methyl Ester To a solution of N-((2-carbo-tert-butoxy-1-naphthyloxy) acetyl)valine methyl ester (1.39 g, 3.34 mmol) in dioxane (15 mL) at room temperature was added 1.0 N LiOH solution (5.0 mL, 5.0 mmol). After stirring at room temperature for 2 hrs, the mixture was acidified (pH 2) with conc HCl and extracted wit EtOAc. The EtOAc extract was washed with saturated NaCl solution, dried over anhydrous sodium sulfate and evaporated to give the mono-carboxylic acid as a gummy solid (1.50 g). The crude product is used without further purification.

To a solution of the above crude acid (1.50 g, ca 3.34 mmol) and aspartic acid, β-tert-butyl, α-methyl ester hydrochloride (0.800 g, 3.34 mmol) in N-methylpyrrolidone(7.5 mL)-$CH_2Cl_2$(7.5 mL) at room temperature under nitrogen was added O-(7-azabenzotriazol-1-yl)-N,N,N',N'-tetramethyluronium hexafluorophate (1.394 g, 3.67 mmol) and diisopropylethylamine (1.75 mL, 10 mmol). After stirring at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The residue was purified by flash chromatography on silica gel eluting with EtOAc-hexane (1:9 to 1:1) to give the title compound (1.25 g, 64%) as a white foam.

Part C

(3S)-3-[N-((2'-Carboxy-1'-Naphthyloxy)Acetyl)-Valinyl]Amino-5-(2'-Fluorophenoxy)-4-Oxopentanoic Acid Starting with N-[N'-((2-carbo-tert-butoxy-1-naphthyloxy) acetyl)valinyl]aspartic acid, β-tert-butyl, α-methyl ester and following the methods described in Example 62, Parts D through G, utilizing 2-fluorophenol in place of 3-hydroxy-1,2,3-benzotriazin-4(3H)-one in Part F, the title compound was prepared. MS(ES) for $C_{29}H_{29}FN_2O_9$ (MW 568.55): positive 591(M+Na); negative 567(M−H).

EXAMPLES 169–171

Starting with N-[N'-((2-carbo-tert-butoxy-1-naphthloxy) acetyl)valinyl]-aspartic acid, β-tert-butyl, α-methyl ester (see Example 168, Part B) and following the methods described in Example 62, Parts D through G, utilizing the appropiate acid or phenol in place of 3-hydroxy-1,2,3-benzotriazin-4(3H)-one in Part F, the compounds shown in Table 11 were also prepared.

TABLE 11

[Structure shown: naphthalene-O-CH2-C(O)-NH-CH(iPr)-C(O)-NH-CH(B)-CO2H with CO2H on naphthalene]

| Ex. | B | Formula | MW | MS(ES) pos. | MS(ES) neg. |
|---|---|---|---|---|---|
| 169 | CH$_2$O(2,3,5,6-tetraF—Ph) | C$_{29}$H$_{26}$F$_4$N$_2$O$_9$ | 622.53 | 645(M + Na) | 621(M − H) |
| 170 | CH$_2$OCO(2,6-diCl—Ph) | C$_{30}$H$_{28}$Cl$_2$N$_2$O$_{10}$ | 647.46 | 669/671 (M + Na) | 645/647 (M − H) |
| 171 | CH$_2$OPOPh$_2$ | C$_{35}$H$_{35}$N$_2$O$_{10}$P | 674.64 | 697(M + Na) | 673(M − H) |

EXAMPLE 172

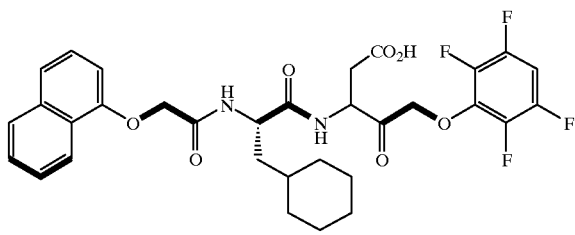

Part A

(3S)-3-(N-Benzyloxycarbonyl)Amino-5-Bromo-4-Oxopentanoic Acid tert-Butyl Ester

A solution of (N-benzyloxycarbonyl)aspartic acid, βtert-butyl ester (2.28 g, 7.06 mmol) and N-methylmorpholine (0.85 mL, 7.7 mmol) in tetrahydrofuran (40 mL) at −10° C. (NaCl/ice bath) under nitrogen was treated dropwise via syringe with isobutyl chloroformate (1.1 mL, 8.5 mmol). After stirring at −10° C. for 20 min, the mixture was filtered (sinctered glass) into a pre-cooled receiver (ice bath) washing the filter cake with additional tetrahydrofuran (approx. 10 mL). The combined filtrate was treated with excess diazomethane/Et$_2$O solution (prepared from 3.10 g, 21 mmol of 1-methyl-3-nitro-1-nitrosoguanidine, 20 mL 40% KOH/10 ml Et$_2$O) at 0° C. (ice bath) under nitrogen. After stirring at 0° C. for 15 min and at room temperature for 30 min, the reaction mixture was again cooled to 0° C. and treated with 48% HBr(2.0 mL, 12 mmol)/acetic acid(2.0 mL). After stirring at 0° C. for 15 mmn and at room temperature for 15 min, the mixture was partitioned between EtOAc-water. The organic phase was washed with water, saturated NaHCO$_3$, and saturated NaCl solutions dried over anhydrous Na$_2$SO$_4$ and evaporated to a dryness. Trituration with hexane gave the crude title compound (3.32 g) as a yellow oil. TLC(EtOAc-hexane; 1:1) Rf=0.60 (intermediate diazoketone Rf=0.52).

Part B

(3S,4RS)-3-(N-Benzyloxycarbonyl)Amino-5-(2',3',5',6'-Tetrafluorophenoxy)-4-Hydroxypentanoic Acid tert-Butyl Ester

To a solution of (3S)-3-(N-benzyloxycarbonyl)amino-5-bromo-4-oxopentanoic acid tert-butyl ester (0.857 g, 2.14 mmol) and 2,3,5,6-tetrafluorophenol (0.410 g, 2.45 mmol) in dimethylformamide (5.0 mL) at room temperature under nitrogen was added potassium fluoride (0.40 g, 6.9 mmol). After stirring at room temperature for 16 hrs, the mixture was diluted with EtOAc, washed with saturated NaHCO$_3$ and saturated NaCl solutions, dried over anhydrous Na$_2$SO$_4$ and evaporated to a to give the crude tetrafluorophenoxymethyl ketone (1.08 g, 98%) as a yellow, viscous oil. TLC (EtOAc-hexane; 1:1) Rf=0.57.

To a solution of the above crude ketone (1.08 g, ca 2.14 mmol) in ethanol (10 mL) at 0° C. under nitrogen was added sodium borohydride (0.057 g, 1.5 mmol). After stirring at 0° C. for 1 hr, the excess reducing agent was discharged by treatment with acetone (1.0 mL), the mixture concentrated and the residue partitioned between EtOAc-half saturated NH$_4$Cl solution. The organic phase was washed with saturated NaHCO$_3$ and saturated NaCl solutions, dried over anhydrous Na$_2$SO$_4$ and evaporated to a dryness. The residue was purified by flash chromatography on silica gel eluting with EtOAc-hexane (1:3) to give the title compound (1.012 g, 94%) as a colorless oil. TLC(EtOAc-hexane; 1:1) Rf=0.48.

Part C

(3S,4RS)-3-[(N-9-Fluorenylmethoxycarbonyl) Cyclohexylalaninyl]Amino-5-(2',3',5',6'-Tetrafluorophenoxy)-4-Hydroxypentanoic Acid tert-Butyl Ester

To a solution of (3S,4RS)-3-(N-benzyloxycarbonyl) amino-5-(2',3',5',6'-tetrafluorophenoxy)-4-hydroxypentanoic acid tert-butyl ester (1.012 g, 2.08 mmol) in MeOH (25 mL) was added 10% Pd-C (0.30 g) and resulting mixture stirred under a hydrogen atmosphere (balloon) for 4 hrs. The mixture was filtered through Celite washing the filter cake with CH$_2$Cl$_2$ and the combined filtrates evaporated to give the crude amine (0.682 g, 93%) as a viscous oil. TLC(MeOH—CH$_2$Cl$_2$; 5:95) Rf=0.21.

To a solution of (N-9-fluorenylmethoxycarbonyl) cyclohexylalanine (0.763 g, 1.94 mmol) in CH$_2$Cl$_2$(10 mL) at 0° C. (ice bath) under nitrogen was added hydroxybenzotriazole hydrate (0.282 g) followed by 1-ethyl-3-(3',3'-dimethyl-1'-aminopropyl)carbodiimide hydrochloride (0.447 g, 2.33 mmol). After stirring at 0° C. for 10 min, the mixture was treated with the above crude amine (0.682 g, ca 1.93 mmol) and the reacton allowed to warm to room temperature. After stirring at room temperature for 3 hrs, the mixture was partitioned between EtOAc-water. The organic phase was washed with water, 5% KHSO$_4$, saturated NaHCO$_3$ and saturated NaCl solutions, dried over anhydrous $Na_2SO_4$ and evaporated to dryness. The residue was purified by flash chromatography eluting with EtOAc-hexane (1:2) to give the title compound (1.028 g, 73%) as yellow foam. TLC (EtOAc-hexane; 1:2) Rf=0.20.

Part D

(3S,4RS)-3-[Cyclohexylalaninyl]Amino-5-(2',3',5',6'-Tetrafluorophenoxy)-4-Hydroxypentanoic Acid tert-Butyl Ester A mixture of (3S,4RS)-3-[(N-9-fluorenylmethoxycarbonyl)cyclohexylalaninyl]amino-5-(2',3',5',6'-tetrafluorophenoxy)-4-hydroxypentanoic acid tert-butyl ester (1.028 g, 1.4 mmol) and 10% piperidine/dimethylformamide (3.0 mL) was stirred at room temperature under nitrogen for 2 hrs. The mixture was diluted with $CH_2Cl_2$, washed with water and saturated $NaHCO_3$ solution, dried over anhydrous anhydrous $Na_2SO_4$ and evaporated to dryness. The residue was purified by flash chromatography eluting with isopropanol-$CH_2Cl_2$ (7:93) to give the title compound (0.561 g, 78%) as a white solid. TLC(MeOH—$CH_2Cl_2$; 5:95) Rf=0.43.

Part E

(3S,4RS)-3-[N-((1'-Naphthyloxy)Acetyl)Cyclohexylalaninyl]-Amino-5-(2',3',5',6'-Tetrafluorophenoxy)-4-Hydroxypentanoic Acid tert-Butyl Ester To a solution of (1-naphthyloxy)acetic acid (0.041 g, 0.20 mmol) and (3S,4RS)-3-[cyclohexylalaninyl]amino-5-(2',3',5',6'-tetrafluorophenoxy)4-hydroxypentanoic acid tert-butyl ester (0.092 g, 0.18 mmol) in $CH_2Cl_2$(5.0 mL) at 0° C. (ice bath) under nitrogen was added hydroxybenzotriazole hydrate (0.050 g) followed by 1-ethyl-3-(3',3'-dimethyl-1'-aminopropyl)carbodiimide hydrochloride (0.042 g, 0.22 mmol). After stirring at 0° C. for 10 min and at room temperature for 18 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to give the crude title compound (0.139 g) as white foam. TLC(EtOAc-hexane; 1:2) Rf=0.25.

Part F

(3RS)-3-[N-((1'-Naphthyloxy)Acetyl)Cyclohexylalaninyl]-Amino-5-(2',3',5',6'-Tetrafluorophenoxy)-4-Oxoxypentanoic Acid tert-Butyl Ester To a solution of crude (3S,4RS)-3-[N-((1'-naphthyloxy)-acetyl)-cyclohexylalaninyl]amino-5-(2',3',5',6'-tetrafluorophenoxy)-4-hydroxypentanoic acid tert-butyl ester (0.139 g, ca 0.18 mmol) in $CH_2Cl_2$ (5 mL) at room temperature under nitrogen was added Dess-Martin Periodinane (0.099 g, 0.23 mmol). After stirring at room temperature for 1.5 hrs, the mixture was diluted with EtOAc, washed with 1.0 M $Na_2S_2O_3$, saturated $NaHCO_3$ and saturated NaCl solutions, dried over anhydrous $Na_2SO_4$ and evaporated to a dryness. The residue was purified by flash chromatography on silica gel eluting with EtOAc-$CH_2Cl_2$-hexane (1:1:2) to give the title compound (0.086 g, 69% overall) as a colorless glass. TLC(EtOAc-hexane; 1:2) two spots (diastereomers) Rf=0.33 and 0.38. Note: racemization of the center alpha to the ketone has apparently occurred at some point in the synthesis.

Part G

(3RS)-3-[N-((1'-Naphthyloxy)Acetyl)Cyclohexylalaninyl]-Amino-5-(2',3',5'6'-Tetrafluorophenoxy)-4-Oxoxypentanoic Acid To a solution of (3RS)-3-[N-((1'-naphthyloxy)-acetyl)-cyclohexylalaninyl]-amino-5-(2',3',5',6'-tetrafluorophenoxy)-4-oxopentanoic acid, tert-butyl ester (0.086 g, 0.125 mmol) in $CH_2Cl_2$(2.0 mL) at room temperature under nitrogen was added trifluoroacetic acid (1.0 mL). The resulting clear solution was stirred at room temperature for 1 hr, evaporated to dryness and chased with toluene-$CH_2Cl_2$ (1:1) to give the title compound (0.066 g, 83%) as an off-white solid. MS(ES) for $C_{32}H_{32}F_4N_2O_7$ (MW 632.61): positive 633(M+H), 655(M+Na); negative 631 (M–H), 745(M+TFA).

EXAMPLES 173–175

Starting with (3S,4RS)-3-[cyclohexylalaninyl]amino-5-(2',3',5',6'-tetrafluorophenoxy)-4-hydroxypentanoic acid tert-butyl ester (see Example 172, Part D) and following the methods described in Example 172, Parts E through G, the compounds shown below in Table 12 were also prepared:

TABLE 12

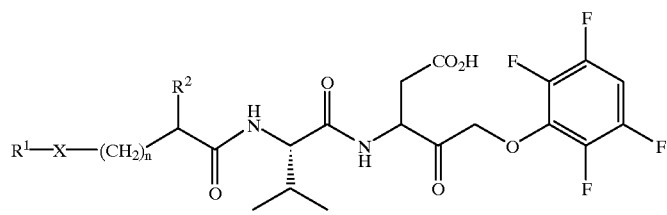

| | | | | | | | MS(ES) | |
|---|---|---|---|---|---|---|---|---|
| Ex. | $R^1$ | X | n | $R^2$ | Formula | MW | pos. | neg. |
| 173 | 2-naphthyl | O | 0 | H | $C_{32}H_{32}F_4N_2O_7$ | 632.61 | 633(M + H) 655(M + Na) 671(M + K) | 631(M – H) 745(M + TFA) |
| 174 | 1-naphthyl | O | 1 | H | $C_{33}H_{34}F_4N_2O_7$ | 646.63 | 647(M + H) 669(M + Na) 685(M + K) | 645(M – H) 759(M + TFA) |
| 175 | (2-Ph)Ph | O | 0 | H | $C_{34}H_{34}F_4N_2O_7$ | 658.65 | 659(M + H) 681(M + Na) 697(M + K) | 657(M – H) 771(M + TFA) |

EXAMPLE 176–177

Starting from (N-benzyloxycarbonyl)alanine and following the general methods described in Example 62, Parts A through G, utilizing either (2-phenylphenoxy)acetic acid or (2-naphthyloxy)acetic acid in place of (1-naphthyloxy) acetic acid in Part C, and 2,3,5,6-tetrafluorophenol in place of 3-hydroxy-1,2,3-benzotriazin-4(3H)-one in Part F, the compounds shown below in Table 13 were also prepared.

TABLE 13

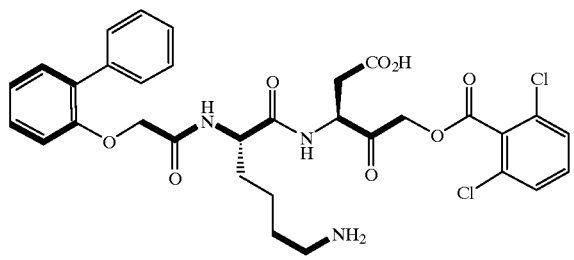

| Ex. | $R^1$ | X | n | $R^2$ | Formula | MW | MS(ES) pos. | MS(ES) neg. |
|---|---|---|---|---|---|---|---|---|
| 176 | 2-naphthyl | O | 0 | H | $C_{26}H_{22}F_4N_2O_7$ | 550.46 | 551(M + H) 573(M + Na) | 549(M − H) 663(M + TFA) |
| 177 | (2-Ph)Ph | O | 0 | H | $C_{21}H_{24}F_4N_2O_7$ | 576.50 | 577(M + H) 599(M + Na) | 575(M − H) 689(M + TFA) |

EXAMPLE 178

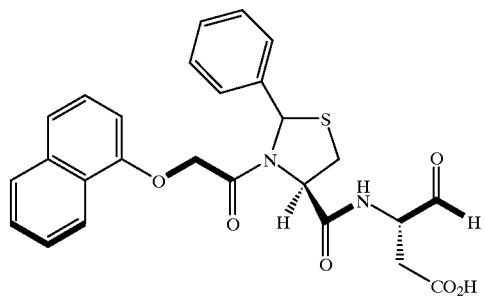

Starting from (N-α-benzyloxycarbonyl-N-ε-t-butoxycarbonyl)lysine and following the general methods described in Example 62, Parts A through G, utilizing (2-phenylphenoxy)acetic acid in place of (1-naphthyloxy) acetic acid in Part C, and 2,6-dichlorobenzoic acid in place of 3-hydroxy-1,2,3-benzotriazin-4(3H)-one in Part F, the title compound was also prepared. MS(ES) for $C_{32}H_{33}Cl_2N_3O_8$ (MW 658.53): positive 658/660(M+H); negative 770/772(M+TFA).

EXAMPLE 179

Part A (2RS,4R)-2-Phenylthiazolidine-4-Carboxylic Acid, Methyl Ester

To a suspension of L-cysteine methyl ester hydrochloride (1.717 g, 10 mmol) in tetrahydrofuran (5.0 mL) at room temperature under nitrogen was added benzaldehyde (1.02 mL, 10 mmol) followed by triethylamine (4.2 mL, 30 mmol). After stirring at room temperature for 3.5 hrs, the resulting mixture was filtered through a pad of silica gel eluting with EtOAc. Evaporation of the filtrate gave the title compound (1.95 g, 88%) as a colorless oil. TLC(EtOAc-hexane; 1:5) Rf=0.22.

Part B (2RS,4R)-3-((1-Naphthyloxy)Acetyl)-2-Phenylthiazolidine-4-Carboxylic Acid, Methyl Ester To a solution of (1-naphthyloxy)acetic acid (3.033 g, 15 mmol) and pyridine (1.46 mL, 18 mmol) in $C_2Cl_2$ (50 mL) at room temperature under nitrogen was added cyanuric fluoride (1.52 mL, 18 mmol). After stirring at room temperature for 3 hrs, the mixture was filtered through sinctered glass and the filtrate evaporated to a viscous oil. The residue was taken up in $CH_2Cl_2$ and diluted with $CH_2Cl_2$ to a total volume of 15.0 mL (ca 1.0 mmol/ml).

To a solution of (2RS,4R)-2-phenylthiazolidine-4-carboxylic Acid, methyl ester (1.953 g, 8.7 mmol) and 2,6-di-tert-butylpyridine (1.95 mL, 8.7 mmol) in $CH_2Cl_2$ (22 mL) at −30° C. (dry ice/acetonitrile bath) under nitrogen was added the above acid fluoride solution (9.0 mL, ca 9.0 mmol). After stirring at −30° C. for 6 hrs, the mixture was allowed to slowly warm to room temperature. After stirring at room temperature for 16 hrs, the mixture was concentrated and the residue partitioned between EtOAc-water. The EtOAc extract was washed with water, 5% $KHSO_4$, saturated $NaHCO_3$ and saturated NaCl solutions, dried over anhydrous $Na_2SO_4$ and eluting with EtOAc-hexane (1:3) to give the title compound (2.672 g, 75%) as a viscous oil.

Part C (2RS,4R)-3-((1-Naphthyloxy)Acetyl)-2-Phenylthiazolidine-4-Carboxylic Acid To a solution of (2RS,4R)-3-((1-naphthyloxy)acetyl)-2-phenylthiazolidine-4-carboxylic acid, methyl ester (2.50 g, 6.14 mmol) in dioxane(15 mL)-water(5.0 mL) at room temperature was added 1.0 N LiOH solution (6.75 mL, 6.75 mmol). After stirring at room temperature for 16 hrs, The mixture was partitioned between EtOAc-5% $KHSO_4$. The organic phase was washed with saturated NaCl solution, dried over anhydrous $Na_2SO_4$ and evaporated to give the title compound (2.42 g, 100%) as a viscous oil. TLC ($MeOH$—$CH_2Cl_2$; 1:9) Rf=0.38.

Part D

(3S,2'RS,4'R)-3-[3'-((1-Naphthyloxy)Acetyl)-2'-Phenylthiazolidine-4'-Carbonyl]Amino-4-Oxobutanoic Acid tert-Butyl Ester Semicarbazone To a solution of (2RS,4R)-3-((1-naphthyloxy)acetyl)-2-phenylthiazolidine-4-carboxylic acid (0.393 g, 1.00 mmol) in $CH_2Cl_2$(10 mL) at 0° C. (ice bath) under nitrogen was added hydroxybenzotriazole hydrate (0.161 g) followed by 1-ethyl-3-(3',3'-dimethyl-1'-aminopropyl)carbodiimide hydrochloride (0.288 g, 1.50 mmol). After stirring at 0° C. for 10 min, (3S)-amino-4-oxobutanoic acid tert-butyl ester semicarbazone, p-toluenesulfonate salt (0.402 g, 1.0 mmol) followed by N-methylmorpholine (0.12 mL, 1.0 mmol) was added. After stirring at 0° C. for 2 hrs and at room temperature for 18 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. The crude product was purified by flash chromatography eluting with EtOAc to give the title compound (0.242 g, 40%) as a colorless foam. TLC(EtOAc) Rf=0.48.

Part E

(3S,2'RS,4'R)-3-[3'-((1-Naphthyloxy)Acetyl)-2'-Phenylthiazolidine-4'-Carbonyl]Amino-4-Oxobutanoic Acid Semicarbazone To a solution (3S,2'RS,4'R)-3-[3'-((1-naphthyloxy)acetyl)-2'-phenylthiazolidine-4'-carbonyl]amino-4-oxobutanoic acid tert-butyl ester semicarbazone (0.240 g, 0.40 mmol) in $CH_2Cl_2$(2.6 mL)-anisole(0.1 mL) at room temperature under nitrogen was added trifluoroacetic acid (0.61 mL). The resulting solution was stirred at room temperature for 18 hrs, evaporated to dryness and chased with toluene-$CH_2Cl_2$ (1:1). The residue was triturated with $Et_2O$ to give the title compound (0.195 g, 89%) as an off-white solid. TLC(MeOH—$CH_2Cl_2$; 1:9) Rf=0.23.

Part F

(3S,2'RS,4'R)-3-[3'-((1-Naphthyloxy)Acetyl)-2'-Phenylthiazolidine-4'-Carbonyl]Amino-4-Oxobutanoic Acid A solution of (3S,2'RS,4'R)-3-[3'-((1-naphthyloxy)acetyl)-2'-phenylthiazolidine-4'-carbonyl]amino-4-oxobutanoic acid semicarbazone (0.195 g, 0.355 mmol) in 37% aqueous formaldehyde-acetic acid-methanol (1:1:3; v:v:v; 7.0 mL) was stirred at room temperature under nitrogen for 18 hrs. The resulting solution was concentrated on a rotovap, diluted with water, frozen and lyophilized. The residue was taken up in MeOH, filtered through Celite and evaporated to dryness. The residue was triturated with $Et_2O$ to give the title compound (0.090 g, 51%) as a white solid. TLC(MeOH—$CH_2Cl_2$; 1:9) Rf=0.60. MS(ES) for $C_{26}H_{24}N_2O_6S$ (MW 492.55): negative 491(M–H).

EXAMPLES 180–184

Following the general methods described in Example 179, Parts A through F, utilizing the appropiate aldehyde in place of benzaldehyde in Part A, the compounds shown in Table 14 were also prepared. In the case of Example 184, (4R)-thiazolidine-4-carboxylic acid, methyl ester was prepared by treatment of (4R)-thiazolidine-4-carboxylic acid (Sigma) with HCl(g) in MeOH.

TABLE 14

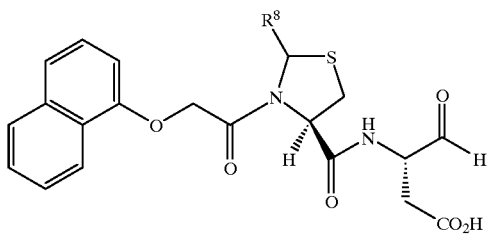

| Ex. | $R^8$ | Formula | MW | MS(ES) pos. | neg. |
|---|---|---|---|---|---|
| 180 | n-propyl | $C_{23}H_{26}N_2O_6S$ | 458.53 | — | 457(M – H) |
| 181 | n-hexyl | $C_{26}H_{32}N_2O_6S$ | 500.61 | 501(M + H) 539(M + Na) | 499(M – H) |
| 182 | iso-propyl | $C_{23}H_{26}N_2O_6S$ | 458.53 | 459(M + H) | 457(M – H) |
| 183 | cyclohexyl | $C_{26}H_{30}N_2O_6S$ | 498.59 | 499(M + H) | 497(M – H) |
| 184 | H | $C_{20}H_{20}N_2O_6S$ | 416.45 | — | 415(M – H) |

EXAMPLE 185

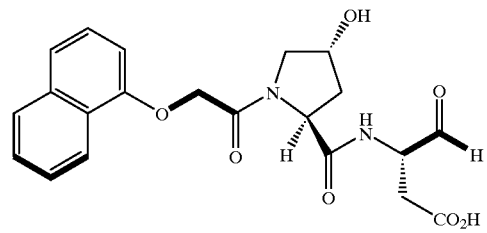

Part A

N-((1-Naphthyloxy)Acetyl)-4'(trans)-Hydroxyproline, Methyl Ester

To a solution of (1-naphthyloxy)acetic acid (1.87 g, 9.23 mmol) and 4(trans)-hydroxyproline, methyl ester (1.34 g, 9.23 mmol) in $CH_2Cl_2$(92 mL) at 0° C. (ice bath) under nitrogen was added hydroxybenzotriazole hydrate (1.48 g) followed by 1-ethyl-3-(3',3'-dimethyl-1'-aminopropyl) carbodiimide hydrochloride (2.65 g, 13.8 mmol). After stirring at 0° C. for 1 hr and at room temperature for 6 hrs, the mixture was concentrated and the residue partitioned between EtOAc-water. The organic phase was washed with water, 5% $KHSO_4$, saturated $NaHCO_3$ and saturated NaCl solutions, dried over anhydrous $Na_2SO_4$ and evaporated to give the title compound (2.59 g, 85%) as a colorless oil. TLC(MeOH—$CH_2Cl_2$; 1:9) Rf=0.48.

Part B

(3S)-3-[N-((1-Naphthyloxy)Acetyl)-4'(trans)-Hydroxyprolinyl]Amino-4-Oxobutanoic Acid Starting with N-((1-naphthyloxy)acetyl)-4'(trans)-hydroxyproline, methyl ester and following the general methods described in Example 179, Parts C through F, the title compound was also prepared. MS(ES) for $C_{21}H_{22}N_2O_7$ (MW 414.41): positive 415(M+H); negative 413(M–H).

EXAMPLE 186

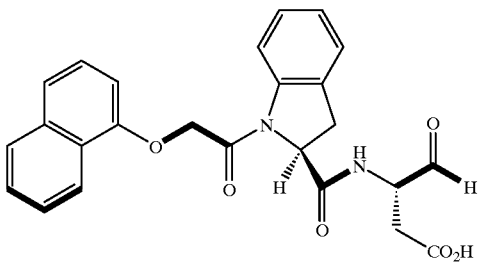

Starting with (2S)-N-[(1-naphthyloxy)acetyl]indoline-2-carboxylic acid (see Example 61, Part B) and following the general methods described in Example 179, Parts D through F, the title compound was also prepared. TLC(AcOH—MeOH—$CH_2Cl_2$; 1:1:20) Rf=0.43. MS(ES) for $C_{25}H_{22}N_2O_6$ (MW 446.46): positive 447(M+H); negative 445(M−H).

EXAMPLE 187

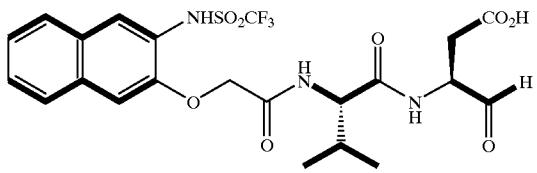

Part A (3-Trifluoromethylsulfonylamino-2-Naphthyloxy) Acetic Acid tert-Butyl Ester To a solution of 3-amino-2-naphthol (0.796 g, 5.0 mmol) in acetone (25 mL) at room temperature under nitrogen was added tert-butyl bromoacetate (0.89 mL, 5.0 mmol) and powdered anhydrous potassium carbonate (2.075 g, 15 mmol). After stirring at room temperature for 18 hrs, the mixture was partitioned between EtOAc-water. The organic phase was washed with water (2x) and saturated NaCl solution, dried over anhydrous sodium sulfate and evaporated to an oil (1.37 g). TLC(EtOAc-hexane; 1:3) Rf=0.36 (Rf of 3-amino-2-naphthol: 0.17).

To a solution of the crude product (1.37 g, ca 5.0 mmol) in $CH_2Cl_2$ (17 mL) at −78° C. under nitrogen was added triethylamine (0.84 mL, 6.0 mmol) followed by trifluoromethanesulfonic anhydride (1.00 mL, 6.0 mmol). After stirring at −78° C. for 30 min, the mixture was allowed to warm to room temperature. After stirring at room temperature for 1 hr, the mixture was partitioned between EtOAc-water. The organic phase was washed with 5% $KHSO_4$, saturated $NaHCO_3$ and saturated NaCl solutions, dried over anhydrous $Na_2SO_4$ and evaporated to dryness. Trituration of the residue with hexane gave the title compound (1.46 g, 72%) as a solid. TLC(EtOAc-hexane; 1:3) Rf=0.42.

Part B (3-Trifluoromethylsulfonylamino-2-Naphthyloxy) Acetic Acid

To a solution of (3-trifluoromethylsulfonylamino-2-naphthyloxy)acetic acid tert-butyl ester (1.46 g, 3.60 mmol) in $CH_2Cl_2$(37 mL)-anisole(0.1 mL)-water(0.57 mL) at room temperature under nitrogen was added trifluroacetic acid (5.7 mL). After stirring at room temperature for 16 hrs, the mixture was evaporated to dryness and chased with toluene-$CH_2Cl_2$ (1:1). The residue was triturated with $Et_2O$ to give the title compound (1.17 g, 92%) as a solid. TLC(MeOH—$CH_2C_2$; 1:9) Rf=0.04.

Part C (3S)-3-[N-((3'-Trifluoromethylsulfonylamino-2'-Naphthyloxy)Acetyl)Valinyl]Amino-4-Oxobutanoic Acid tert-Butyl Ester Semicarbazone To a solution of (3-trifluoromethylsulfonylamino-2-naphthyloxy)acetic acid (0.175 g, 0.5 mmol) in N-methylpyrrolidone(1.0 mL)-$CH_2Cl_2$(5.0 mL) at 0° C. (ice bath) under nitrogen was added hydroxybenzotriazole hydrate (0.092 g) followed by 1-ethyl-3-(3',3'-dimethyl-1'-aminopropyl)carbodiimide hydrochloride (0.144 g, 0.75 mmol). After stirring for 15 min, the mixture was treated with (3S)-N-(valinyl)amino-4-oxobutanoic acid tert-butyl ester semicarbazone (0.165 g, 0.5 mmol, prepared by a method analogous to that described for N-(leucinyl)amino-4-oxobutanoic acid tert-butyl ester semicarbazone, see Example 1, Part B and Example 2, Part A) and N-methylmorpholine (0.066 mL, 0.6 mmol). After stirring at 0° C. for 2 hrs and at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. Trituration of the residue with $Et_2O$-hexane gave the title compound (0.201 g, 61%) as a solid. TLC(MeOH—$CH_2Cl_2$; 1:9) Rf=0.38.

Part D (3S)-3-[N-((3'-Trfluoromethylsulfonylamino-2'-Naphthyloxy)Acetyl)Valinyl]Amino-4-Oxobutanoic Acid Semicarbazone A solution of (3S)-3-[N-((3'-trifluoromethylsulfonylamino-2'-naphthyloxy)acetyl)-valinyl]amino-4-oxobutanoic acid tert-butyl ester semicarbazone (0.201 g, 0.30 mmol) in 6.0N HCl/AcOH (3.0 mL) was stirred at room temperature under nitrogen for 1 hr. The resulting mixture was evaporated to dryness and chased with toluene. The residue was triturated with $Et_2O$ to give the title compound (0.146 g, 80%) as a solid. TLC(MeOH—$CH_2Cl_2$; 1:9) Rf=0.08.

Part E (3S)-3-[N-((3'-Trifluoromethylsulfonylamino-2'-Naphthyloxy)Acetyl)Valinyl]Amino-4-Oxobutanoic Acid A solution of (3S)-3-[N-((3'-trifluoromethylsulfonyl-amino-2'-naphthyloxy)acetyl)valinyl]amino-4-oxobutanoic acid semicarbazone (0.146 g, 0.24 mmol) in MeOH-acetic acid-37% aqueous formaldehyde (3.0 mL, 3:1:1, v:v:v), was stirred at room temperature under nitrogen for 16 hrs. The mixture was concentrated, diluted with water, frozen and lyophilized. The residue was taken up in methanol, filtered and evaporated to dryness. The residue was triturated with $Et_2O$ to give the title compound (0.103 g, 78%) as a solid. MS(ES) for $C_{22}H_{24}F_3N_3O_8S$ (MW 547.50): negative 546 (M−H).

EXAMPLE 188

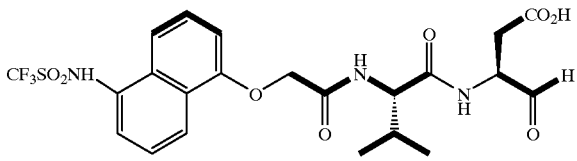

Part A

(5-Trifluoromethylsulfonylamino-1-Naphthyloxy) Acetic Acid

To a solution of 5-amino-1-naphthol (0.790 g, 5.0 mmol) in acetone (25 mL) at room temperature under nitrogen was added methyl bromoacetate (0.57 mL, 6.0 mmol) and powdered anhydrous potassium carbonate (2.075 g, 15 mmol). After stirring at room temperature for 18 hrs, the mixture was partitioned between EtOAc-water. The organic phase was washed with water (2×) and saturated NaCl solution, dried over anhydrous sodium sulfate and evaporated to an oil (1.16 g).

To a solution of the above crude product (1.16 g, ca 5.0 mmol) in $CH_2Cl_2$ (17 mL) at −78° C. under nitrogen was added triethylamine (0.84 mL, 6.0 mmol) followed by trifluoromethanesulfonic anhydride (1.00 mL, 6.0 mmol). After stirring at −78° C. for 30 min, the mixture was allowed to warm to room temperature. After stirring at room temperature for 1 hr, the mixture was partitioned between EtOAc-water. The organic phase was washed with 5% $KHSO_4$, saturated $NaHCO_3$ and saturated NaCl solutions, dried over anhydrous $NASO_4$ and evaporated to dryness to give the crude sulfonamide (1.82 g, 100%) as a solid.

The above crude product was taken up in dioxane-water (16.7 mL, 3:1, v:v) and treated with 1.0N LiOH solution (11 mL, 11 mmol). After stirring at room temperature for 16 hrs, the mixture was acidified with conc HCl, and extracted with anhydrous $Na_2SO_4$ and evaporated to dryness. The residue was triturated with $Et_2O$ to give the title compound (1.27 g, 73%) as a solid.

Part B

(3S)-3-[N-((5'-Trifluoromethylsulfonylamino-1'-Naphthyloxy)Acetyl)Valinyl]Amino-4-Oxobutanoic Acid tert-Butyl Ester Semicarbazone To a solution of (5-trifluoromethylsulfonylamino-1-naphthyloxy)acetic acid (0.175 g, 0.5 mmol) and (3S)-N-(valinyl)amino-4-oxobutanoic acid tert-butyl ester semicarbazone (0.165 g, 0.5 mmol) in N-methylpyrrolidone(2.5 mL)-$CH_2Cl_2$(2.5 mL) at 0° C. (ice bath) under nitrogen was added O-(7-azabenzotriazol-1-yl)-N,N,N',N'-tetramethyluronium hexafluorophate (0.165 g, 0.5 mmol) followed by diisopropylethylamine (0.17 mL, 0.98 mmol). After stirring at 0° C. for 1 hr and at room temperature for 16 hrs, the mixture was partitioned between EtOAc-water. The organic phase was washed with water, 5% $KHSO_4$, saturated $NaHCO_3$ and saturated NaCl solutions, dried over anhydrous $Na_2SO_4$ and evaporated to dryness. Trituration of the residue with $Et_2O$-hexane gave the title compound (0.067 g, 20%) as a solid. TLC(AcOH—MeOH—$CH_2Cl_2$; 1:1:20) Rf=0.29.

Part C

(3 S)-3-[N-((5'-Trfluoromethylsulfonylamino-1'-Naphthyloxy)Acetyl)Valinyl]Amino-4-Oxobutanoic Acid A solution of (3S)-3-[N-((5'-trifluoromethylsulfonyl-amino-1'-naphthyloxy)acetyl)-valinyl]amino-4-oxobutanoic acid tert-butyl ester semicarbazone (0.067 g, 0.10 mmol) in 6.0N HCl/AcOH (1.0 mL) was stirred at room temperature under nitrogen for 1 hr. The resulting mixture was evaporated to dryness and chased with toluene. TLC(AcOH—MeOH—$CH_2Cl_2$; 1:1:8) Rf=0.55.

A solution of the above crude product (ca 0.10 mmol) in MeOH-acetic acid-37% aqueous formaldehyde (3.3 mL, 3:1:1, v:v:v), was stirred at room temperature under nitrogen for 16 hrs. The mixture was concentrated, diluted with water, frozen and lyophilized. The residue was taken up in methanol, filtered and evaporated to dryness. The residue was triturated with $Et_2O$ to give the title compound (0.041 g, 75%) as a solid. TLC(AcOH—MeOH—$CH_2Cl_2$; 1:1:8) Rf=0.73. MS(ES) for $C_{22}H_{24}F_3N_3O_8S$ (MW 547.50): positive 570(M+Na); negative 546(M−H).

EXAMPLE 189

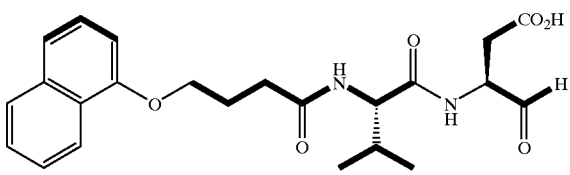

Part A

(3S)-3[N-(9-Fluorenylmethoxycabonyl)Valinyl] Amino-4-Oxobutanoic Acid (tert-Butyl) Ester Semicarbazonyl-4-[2'-(4-Ethyl-Phenoxyacetyl)] Aminomethylpolystrene Aminomethylpolystryene resin (10.0 g, 100–200 mesh, 0.71 meq/g) was placed in a 200 mL filter tube equipped with a vacuum stopcock and glass frit and washed successively with $CH_2Cl_2$(50 mL)/dimethylformamide(50 mL), diisopropylethylamine(5 mL)/dimethylformamide(30 mL), dimethylformamide (2×50 mL) and tetrahydrofuran (30 mL). The resin was suspended in tetrahydrofuran(20 mL)/ N-methylpyrolidinone(20 mL) with nitrogen agitation through the bottom of the frit and treated with diiospropylethylamine (1.9 mL, 10.9 mmol) and (3S)-3-(9-fluorenylmethoxycabonyl)amino-4-oxobutanoic acid (tert-butyl) ester semicarbazonyl-4-[2'-(4-ethyl-phenoxyacetic acid)] (2.24 g, 3.56 mmol). After all of the solid had dissolved (approx. 10 min), the mixture was treated with pyBOP [benzotriazolyloxy-tris(N-pyrolidinyl)phosphonium hexafluorophosphate, 2.78 g, 5.34 mmol) in one portion. After mixing by nitrogen agitation for 3 hrs, the supernatant was removed by suction and the resin washed succesively with tetrahydrofuran (2×50 mL), dimethylformamide (3×50 mL) and $CH_2Cl_2$ (2×50 mL). Unreacted amine groups were capped by treatment with a mixture of acetic anhydride(10 mL)/dimethylformamide(30 mL)/diisopropylethylamine (1.0 mL). After mixing by nitrogen agitation for 1 hr, the supernatant was removed by suction and the resin washed with dimethylformamide(4×50 mL).

The resin was treated with piperidine(10 mL)/ dimethylformamide(40 mL) and mixed by nitrogen agitation for 1 hr. The supernatant was removed by suction and the resin washed with dimethylformamide(4×50 mL) and tetrahydrofuran (50 and the resin washed with dimethylformamide(4×50 mL) and tetrahydrofuran (50

The resin was suspended in tetrahydrofuran(20 mL)/N-methylpyrolidinone(20 mL), treated with N-(9-fluorenylmethoxycabonyl)valine (3.63 g, 10.7 mmol), diisopropylethylamine (5.7 mL, 32.7 mmol) and pyBOP (8.34 g, 16.0 mmol) and mixed by nitrogen agitation for 2.5 hrs. The supernatant was removed by suction and the resin washed succesively with dimethylformamide (3×40 mL) and $CH_2Cl_2$ (3×40 mL), methanol (2×40 mL) and $Et_2O$ (2×40 mL). The resin was dried in vacuo to give the title product (12.69 g, quanitative). Based on the starting semicarbazone-acid, the resin loading was calculated as approximately 0.28 meq/g.

Part B (3S)-3-[N-(4-(1'-Naphthyloxy)Butyryl)Valinyl] Amino-4-Oxobutanoic Acid

An aliquot of the Part A resin (0.125 g, ca 0.035 mmol) was placed in a 6 mL Supelco™ fitration tube equipped with a 20 μm polyethylene frit, treated with piperidine-dimethylformamide (1.0 mL, 1:4 v/v) and mixed on an orbital shaker for 1 hr. The supernatant was removed by suction and the resin washed with dimethylformamide (4×1.0 mL) and $CH_2Cl_2$ (3×1.0 mL). The resin was treated with 0.5M $iPr_2NEt$ in N-methylpyrolidinone (0.40 mL, 0.20 mmol), 4-(1-naphthyloxy)butyric acid (0.0264 g, 0.115 mmol) and 0.25M O-(7-azabenzotriazol-1-yl)-N,N,N',N'-tetramethyluronium hexafluorophate in N-methylpyrolidinone (0.40 mL, 0.10 mmol). The mixture was mixed on an orbital shaker under an nitrogen atmosphere for 16 hrs. The supernatant was removed by suction and the resin washed succesively with dimethylformamide (3×1.0 mL) and $CH_2Cl_2$ (3×1.0 mL), methanol (2×1.0 mL) and $Et_2O$ (2×1.0 mL).

The resin was treated with 1.0 mL of $CH_2Cl_2$ and allowed to re-swell for 15 min. The solvent was removed by suction and the resin treated with trifluoroacetic acid-$CH_2Cl_2$-anisole (1.0 mL, 4:3:1 v/v/v). After mixing on an orbital shaker under nitrogen for 5.5 hrs, the supernatant was removed by suction and the resin washed with $CH_2Cl_2$ (4×1.0 mL). The resin was treated with 37% aqueous formaldehyde-acetic acid-tetrahydrofuran-trifluoroacetic acid (1.0 mL, 1:1:5:0.025 v/v/v/v) and mixed on an orbital shaker under nitrogen for 4.5 hrs. The supernatant was collected by suction, the resin washed with tetrahydrofuran (3×0.5 mL). The combined filtrates were blown down under nitrogen. The residue was taken up in methanol (0.5 mL), filtered and applied directly to a 3 mL Supelco™ LC-18 reverse phase extraction tube which had been pre-conditioned with water, and eluted successively with 3 mL each of 10% MeOH-water, 30% MeOH-water, 60% MeOH-water and 90% MeOH-water. The MeOH-water, 30% MeOH-water, 60% MeOH-water and 90% MeOH-water. The the title compound (0.0132 g, 88%) as a colorless glass. TLC(AcOH—MeOH—$CH_2Cl_2$; 1:1:20) Rf=0.22. MS(ES) for $C_{23}H_{28}N_2O_6$ (MW 428.48): positive 451(M+Na), 467 (M+K); negative 427(M−H).

EXAMPLES 190–194

Starting with (3S)-3-[N-(9-fluorenylmethoxycabonyl) valinyl]amino-4-oxobutanoic acid (tert-butyl) ester semicarbazonyl-4-[2'-(4-ethyl-phenoxyacetyl)] aminomethylpolystrene (see Example 189, Part A) and following the methods described in Example 189, Part B, the compounds shown below in Table 15 were also prepared:

TABLE 15

![structure: R¹—X—(CH₂)ₙ—CH(R²)—C(=O)—NH—CH(iPr)—C(=O)—NH—CH(CH₂CO₂H)—CHO]

| Ex. | R¹ | X | n | R² | Formula | MW | MS(SE) pos. | neg. |
|---|---|---|---|---|---|---|---|---|
| 190 | (2-t-Bu)Ph | O | 0 | H | $C_{21}H_{30}N_2O_6$ | 406.48 | 429(M + Na) 445(M + K) | 405(M − H) |
| 191 | (2-Ph)Ph | O | 0 | H | $C_{23}H_{26}N_2O_6$ | 426.47 | 449(M + Na) 465(M + K) | 425(M − H) |
| 192 | (2-Ph)Ph | O | 0 | $CH_3$ | $C_{24}H_{28}N_2O_6$ | 440.50 | 463(M + Na) | 439(M − H) |
| 193 | (2-Ph)Ph | O | 1 | H | $C_{24}H_{28}N_2O_6$ | 440.50 | 441(M + H) 463(M + Na) 479(M + K) | 439(M − H) 553(M + TFA) |
| 194 | 1-naphthyl | O | 1 | H | $C_{22}H_{26}N_2O_6$ | 414.46 | 415(M + H) 437(M + Na) 453(M + K) | 413(M − H) |

Although the invention has been described with reference to the examples provided above, it should be understood that various modifications can be without departing from the spirit of the invention. Accordingly, the invention is limited only by the claims.

We claim:

1. An isolated compound of the following formula:

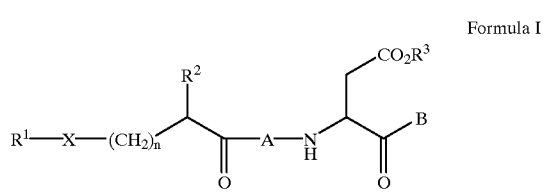

Formula I wherein:

n is 0, 1 or 2;

X is $CH_2$, C=O, O, S or NH;

A is a moiety of Formula IIa-i:

IIa, IIb, IIc, IId, IIe, IIf, IIg, IIh, IIi (chemical structures)

B is a hydrogen atom, a deuterium atom, $C_{1-10}$ straight chain branched alkyl, cycloalkyl, phenyl, substituted phenyl, naphthyl, substituted naphthyl, 2-benzoxazolyl, substituted 2-oxazolyl, $(CH_2)_m$ cycloalkyl, $(CH_2)_m$phenyl, $(CH_2)_m$(substituted phenyl), $(CH_2)_m$(1 or 2-naphthyl), $(CH_2)_m$heteroaryl, halomethyl, $CO_2R^{13}$, $CONR^{14}R^{15}$, $CH_2ZR^{16}$, $CH_2OCO(aryl)$, $CH_2OCO(heteroaryl)$, or $CH_2OPO(R^{17})R^{18}$, where Z is an oxygen or a sulfur atom, or B is a group of the Formula IIIa-c:

IIIa, IIIb, IIIc (chemical structures)

$R^1$ is phenyl, substituted phenyl, naphthyl, substituted naphthyl, heteroaryl, or substituted heteroaryl;

$R^2$ is hydrogen, alkyl, cycloalkyl, phenyl, substituted phenyl, $(CH_2)_m NH_2$, $(CH_2)_m NHCOR^{10}$, $(CH_2)_m N(C=NH)NH_2$, $(CH_2)_p CO_2 R^3$, $(CH_2)_p OR^{11}$, $(CH_2)_p SR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

$R^3$ is hydrogen, alkyl, cycloalkyl, (cycloalkyl)alkyl, phenylalkyl, or substituted phenylalkyl; and wherein $R^4$ is alkyl, cycloalkyl, phenyl, substituted phenyl, $(CH_2)_m NH_2$, $(CH_2)_m NHCOR^{10}$, $(CH_2)_m N(C=NH)NH_2$, $(CH_2)_p CO_2 R^3$, $(CH_2)_p OR^{11}$, $(CH_2)_p SR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$ heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl;

$R^{4a}$ is hydrogen, or methyl, or $R^4$ and $R^{4a}$ taken together are $-(CH_2)_d-$ where d is an interger from 2 to 6;

$R^5$ is phenyl, substituted phenyl, $(CH_2)_p$phenyl, $(CH_2)_p$(substituted phenyl), cycloalkyl, or benzofused cycloalkyl;

$R^6$ is hydrogen, alkyl, cycloalkyl, phenyl, substituted phenyl, $(CH_2)_m$cycloalkyl, $(CH_2)_m$phenyl, $(CH_2)_m$(substituted phenyl), or $(CH_2)_m$(1 or 2-naphthyl);

$R^7$ is hydrogen, fluorine, oxo, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{11}$, $SR^{12}$, or $NHCOR^{10}$;

$R^8$ is hydrogen, oxo, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^9$ is alkyl, cycloalkyl, $(CH_2)_m$cycloalkyl, $(CH_2)_m$phenyl, $(CH_2)_m$(substituted phenyl), $(CH_2)_m$(1 or 2-naphthyl), or $COR^{10}$;

$R^{10}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{13}$, or $NR^{14}R^{15}$;

$R^{11}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^{12}$ is alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl);

$R^{13}$ is alkyl, cycloalkyl, $(CH_2)_m$cycloalkyl, $(CH_2)_m$phenyl, $(CH_2)_m$(substituted phenyl), or $(CH_2)_m$(1 or 2-naphthyl);

$R^{14}$ is hydrogen, alkyl, cycloalkyl, phenyl, substituted phenyl, naphthyl, substituted naphthyl, $(CH_2)_m$cycloalkyl, $(CH_2)_m$phenyl, $(CH_2)_m$(substituted phenyl), or $(CH_2)_m$(1 or 2-naphthyl);

$R^{15}$ is hydrogen or alkyl; or $R^{14}$ and $R^{15}$ taken together form a five, six or seven membered carbocyclic or heterocyclic ring, such as morpholine or N-substituted piperazine;

$R^{16}$ is phenyl, substituted phenyl, naphthyl, substituted naphthyl, heteroaryl, $(CH_2)_m$phenyl, $(CH_2)_m$(substituted phenyl), $(CH_2)_m$(1 or 2-naphthyl), or $(CH_2)_m$heteroaryl;

$R^{17}$ and $R^{18}$ are independently alkyl, cycloalkyl, phenyl, substituted phenyl, naphthyl, or phenylalkyl, substituted phenylalkyl, or (cycloalkyl)alkyl;

$R^{19}$ and $R^{20}$ are independently hydrogen, alkyl, phenyl, substituted phenyl, $(CH_2)_m$phenyl, or $(CH_2)_m$(substituted phenyl), or $R^{19}$ and $R^{20}$ taken together are $-(CH=CH)_2-$;

$R^{21}$ is hydrogen, alkyl, phenyl, substituted phenyl, $(CH_2)_m$ phenyl, $(CH_2)_m$(substituted phenyl);

$R^{22}$, $R^{23}$ and $R^{24}$ are independently hydrogen or alkyl;

$Y^1$ is $CH_2$, $(CH_2)_2$, $(CH_2)_3$, or S;

$Y^2$ is O or $NR^{24}$;

$Y^3$ is $CH_2$, O, or $NR^{24}$;

a is 0 or 1 and b is 1 or 2, provided that when a is 1 then b is 1;

c is 1 or 2, provided that when c is 1 then a is 0 and b is 1;

m is 1,2,3 or 4; and p is 1 or 2;

or a salt thereof.

2. The compound of claim 1 where X is oxygen.

3. The compound of claim 1 where X is sulfur.

4. The compound of claim 1 where X is NH.

5. The compound of claim 1 where X is $CH_2$.

6. The compound of claim 1 where X is C=O.

7. The compound of claim 1 wherein A is

IIa

8. The compound of claim 1 wherein $R^4$ is lower alkyl, cycloalkyl, phenyl, substituted phenyl, $(CH_2)_n NH_2$, $(CH_2)_m OR^{10}$, $(CH_2)_m SR^{11}$, $(CH_2)_n$cycloalkyl, $(CH_2)_n$phenyl, $(CH_2)_n$(substituted phenyl), or $(CH_2)_n$(1 or 2-naphthyl); and $R^{4a}$ is hydrogen.

9. The compound of claim 1 wherein A is

IIb

10. The compound of claim 9 wherein $R^5$ is phenyl, substituted phenyl, $(CH_2)_m$phenyl, $(CH_2)_m$(substituted phenyl), cycloalkyl, or 2-indanyl.

11. The compound of claim 1 wherein A is

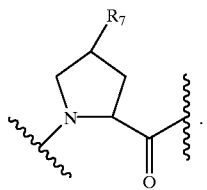

12. The compound of claim 11 wherein $R^7$ is hydrogen, fluorine, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, or $SR^{11}$.

13. The compound of claim 1 wherein A is

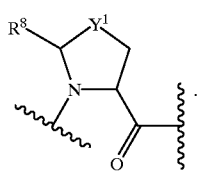

14. The compound of claim 13 wherein
$R^8$ is hydrogen, oxo, cycloalkyl, phenyl, substituted phenyl, or naphthyl; and
$Y^1$ is $CH_2$, $(CH_2)_2$, $(C_2)_3$, or S.

15. The compound of claim 1 wherein A is

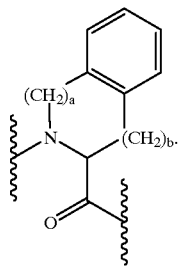

16. The compound of claim 15 wherein a is 0.

17. The compound of claim 1 wherein
B is hydrogen, 2-benzoxazolyl, substituted 2-oxazolyl, $CH_2ZR^{15}$, $CH_2OCO(aryl)$, or $CH_2OPO(R^{16})R^{17}$; and
Z is O or S.

18. The compound of claim 1 wherein B is

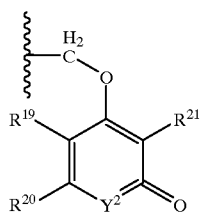

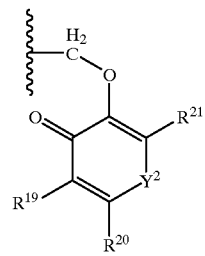

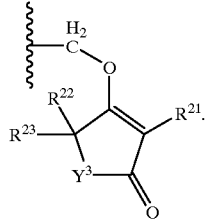

19. The compound of claim 18 wherein $R^{19}$ and $R^{20}$ are independently hydrogen, alkyl, or phenyl, or wherein $R^{19}$ and $R^{20}$ taken together are —(CH=CH)$_2$—.

20. The compound of claim 1 wherein
X is O or NH;
n is 0 or 1;
$R^1$ is substituted phenyl, naphthyl, or substituted naphthyl;
$R^2$ is hydrogen, lower alkyl, $(CH_2)_pCO_2R^3$, $(CH_2)_m$(substituted phenyl), $(CH_2)_m$(1- or 2-naphthyl), or $(CH_2)_m$tetrazolyl; and
$R^3$ is hydrogen or lower alkyl.

21. The compound of claim 20 wherein $R^1$ is 1-naphthyl.
22. The compound of claim 20 wherein $R^1$ is 2-naphthyl.
23. The compound of claim 20 wherein $R^1$ is substituted naphthyl.
24. The compound of claim 23 wherein substituted naphthyl is 2-carboxy-1-naphthyl.
25. The compound of claim 20 wherein $R^1$ is substituted phenyl.
26. The compound of claim 25 wherein substituted phenyl is 2-substituted phenyl.
27. The compound of claim 26 wherein 2-substituted phenyl is (2-phenyl)phenyl.
28. The compound of claim 20 wherein A is alanine, valine, leucine cyclohexylalanine, phenylgycine or t-butylglycine.
29. The compound of claim 28 wherein $R^1$ is 1-naphthyl.
30. The compound of claim 28 wherein $R^1$ is 2-naphthyl.
31. The compound of claim 28 wherein $R^1$ is substituted naphthyl.
32. The compound of claim 31 wherein substituted naphthyl is 2-carboxy-1-naphthyl.
33. The compound of claim 28 wherein $R^1$ is 2-substituted phenyl.
34. The compound of claim 33 wherein 2-substituted phenyl is (2-phenyl)phenyl.
35. The compound of claim 20 wherein $R^2$ is $(CH_2)_2CO_2R^3$ and n is 0.
36. A composition comprising a compound of claim 1 in combination with a carrier.

* * * * *